(12) United States Patent
Washko, Jr. et al.

(10) Patent No.: US 12,293,832 B2
(45) Date of Patent: May 6, 2025

(54) SYSTEM AND METHOD FOR PREDICTING THE RISK OF FUTURE LUNG CANCER

(71) Applicant: Johnson & Johnson Enterprise Innovation Inc., New Brunswick, NJ (US)

(72) Inventors: George R. Washko, Jr., West Roxbury, MA (US); Christopher Scott Stevenson, West Sussex (GB); Samuel Yoffe Ash, Newton, MA (US); Raul San Jose Estepar, Wellesley, MA (US); Matthew David Mailman, New Hope, PA (US)

(73) Assignee: Johnson & Johnson Enterprise Innovation Inc., New Brunswick, NJ (US)

( * ) Notice: Subject to any disclaimer, the term of this patent is extended or adjusted under 35 U.S.C. 154(b) by 368 days.

(21) Appl. No.: 17/863,978

(22) Filed: Jul. 13, 2022

(65) Prior Publication Data
US 2023/0027734 A1 Jan. 26, 2023

Related U.S. Application Data

(60) Provisional application No. 63/328,590, filed on Apr. 7, 2022, provisional application No. 63/222,712, filed on Jul. 16, 2021.

(51) Int. Cl.
*G16H 50/30* (2018.01)
*G06T 7/00* (2017.01)
(Continued)

(52) U.S. Cl.
CPC ........... *G16H 50/20* (2018.01); *G06T 7/0016* (2013.01); *G06V 10/44* (2022.01); *G06V 10/50* (2022.01);
(Continued)

(58) Field of Classification Search
CPC ........ G16H 50/20; G16H 50/30; G16H 30/40; G16H 50/50; G16H 50/70; G06T 7/0016;
(Continued)

(56) References Cited

U.S. PATENT DOCUMENTS 10,140,421 B1 * 11/2018 Bernard .................. G01T 1/247
10,470,734 B2 * 11/2019 Madabhushi ............ A61B 5/08
(Continued)

FOREIGN PATENT DOCUMENTS

JP 2009106335 A 5/2009
JP 2019153015 A 9/2019
(Continued)

OTHER PUBLICATIONS

International Search Report and Written Opinion for PCT Application No. PCT/IB2022/056474, dated Oct. 5, 2022, pp. 1-18.
(Continued)

*Primary Examiner* — Cindy Trandai
(74) *Attorney, Agent, or Firm* — Paradice & Li LLP

(57) ABSTRACT

Risk prediction models are trained and deployed to analyze images, such as computed tomography scans, for predicting risk of lung cancer (e.g., current or future risk of lung cancer) for one or more subjects. Individual risk prediction models are trained on nodule-specific and non-nodule specific features, including longitudinal nodule specific and longitudinal non-nodule specific features, such that each risk prediction model can predict risk of lung cancer across different time horizons. Such risk prediction models are useful for developing preventive therapies for lung cancer by enabling clinical trial enrichment.

20 Claims, 41 Drawing Sheets

(51) Int. Cl.
  *G06V 10/44* (2022.01)
  *G06V 10/50* (2022.01)
  *G06V 10/774* (2022.01)
  *G16H 50/20* (2018.01)

(52) U.S. Cl.
  CPC .......... *G06V 10/774* (2022.01); *G16H 50/30* (2018.01); *G06T 2207/10081* (2013.01); *G06T 2207/10116* (2013.01); *G06T 2207/20081* (2013.01); *G06T 2207/30064* (2013.01); *G06T 2207/30096* (2013.01); *G06V 2201/03* (2022.01)

(58) Field of Classification Search
  CPC . G06T 2207/10081; G06T 2207/10116; G06T 2207/20081; G06T 2207/30064; G06T 2207/30096; G06T 7/0012; G06T 2207/20084; G06V 10/44; G06V 10/50; G06V 10/774; G06V 2201/03; G06V 10/82; G06V 2201/031; A61B 6/5217; A61B 6/032; A61B 6/5211; A61B 6/03; A61B 6/5229; G06N 3/045
  See application file for complete search history.

(56) References Cited

U.S. PATENT DOCUMENTS

| | | | |
|---|---|---|---|
| 11,321,841 B2 | 5/2022 | Nakane et al. | |
| 11,430,121 B2* | 8/2022 | Chaganti | G06T 11/008 |
| 11,640,661 B2 | 5/2023 | Washko, Jr. et al. | |
| 11,869,187 B2 | 1/2024 | Washko, Jr. et al. | |
| 2003/0174873 A1 | 9/2003 | Giger et al. | |
| 2010/0272341 A1 | 10/2010 | Reeves et al. | |
| 2013/0004044 A1* | 1/2013 | Ross | G06T 7/0016 |
| | | | 382/128 |
| 2013/0343626 A1 | 12/2013 | Rico et al. | |
| 2015/0265251 A1* | 9/2015 | Cho | G06T 7/143 |
| | | | 600/437 |
| 2016/0203263 A1 | 7/2016 | Maier et al. | |
| 2017/0035381 A1 | 2/2017 | Madabhushi et al. | |
| 2018/0068083 A1 | 3/2018 | Cohen et al. | |
| 2018/0242905 A1 | 8/2018 | Madabhushi et al. | |
| 2018/0353149 A1 | 12/2018 | Madabhushi et al. | |
| 2018/0365829 A1 | 12/2018 | Madabhushi et al. | |
| 2019/0080450 A1* | 3/2019 | Arar | G06T 7/194 |
| 2019/0131016 A1 | 5/2019 | Cohen et al. | |
| 2019/0259154 A1 | 8/2019 | Madabhushi et al. | |
| 2019/0357870 A1* | 11/2019 | Madabhushi | G06V 10/764 |
| 2020/0005901 A1* | 1/2020 | Cohen | G06N 20/20 |
| 2020/0085382 A1* | 3/2020 | Taerum | G06T 7/0016 |
| 2020/0160980 A1 | 5/2020 | Lyman et al. | |
| 2020/0171024 A1* | 6/2020 | Schwartz | A61K 31/4412 |
| 2020/0211186 A1* | 7/2020 | Gong | A61B 5/0033 |
| 2020/0211710 A1 | 7/2020 | Do et al. | |
| 2020/0265276 A1* | 8/2020 | Xu | G06V 10/454 |
| 2020/0320692 A1 | 10/2020 | Fleming | |
| 2021/0110540 A1 | 4/2021 | Vaidya et al. | |
| 2021/0110928 A1 | 4/2021 | Vaidya et al. | |
| 2021/0118130 A1 | 4/2021 | Zhang et al. | |
| 2021/0169349 A1 | 6/2021 | Madabhushi et al. | |
| 2021/0217495 A1* | 7/2021 | Arnaout | G16B 20/40 |
| 2021/0225511 A1 | 7/2021 | Kiraly et al. | |
| 2021/0238694 A1* | 8/2021 | Gross | C12Q 1/6827 |
| 2021/0287795 A1* | 9/2021 | Declerck | G16H 30/20 |
| 2022/0028551 A1 | 1/2022 | Jordan et al. | |
| 2022/0122249 A1* | 4/2022 | Park | G16H 40/67 |
| 2022/0148169 A1 | 5/2022 | Mermel et al. | |
| 2022/0148727 A1* | 5/2022 | Arteta | G06N 3/04 |
| 2022/0215535 A1* | 7/2022 | Kong | G06V 10/44 |
| 2022/0240881 A1* | 8/2022 | Huang | G06T 7/0016 |
| 2022/0301714 A1 | 9/2022 | Kim | |
| 2022/0351000 A1* | 11/2022 | Middlebrooks | G16H 50/20 |
| 2023/0027734 A1 | 1/2023 | Washko, Jr. et al. | |
| 2023/0162359 A1* | 5/2023 | Choi | G16H 50/20 |
| | | | 382/128 |
| 2023/0274428 A1 | 8/2023 | Fujii et al. | |
| 2023/0290452 A1* | 9/2023 | Kast | G16H 50/20 |
| 2024/0202917 A1 | 6/2024 | Washko, Jr. et al. | |

FOREIGN PATENT DOCUMENTS

| | | |
|---|---|---|
| JP | 2019198376 A | 11/2019 |
| WO | 2015127355 A1 | 8/2015 |
| WO | 2017064600 A1 | 4/2017 |
| WO | 2018055987 A1 | 3/2018 |
| WO | 2019008798 A1 | 1/2019 |
| WO | 2019048418 A1 | 3/2019 |
| WO | 2021015913 A1 | 1/2021 |
| WO | 2021049729 A1 | 3/2021 |

OTHER PUBLICATIONS

International Preliminary Report on Patentability for PCT Application No. PCT/IB2022/056474, dated Jan. 25, 2024, pp. 1-16.

Kalpathy-Cramer et al., "Radiomics of Lung Nodules: A Multi-Institutional Study of Robustness and Agreement of Quantitative Imaging Features," Tomography.org, vol. 2, No. 4, Dec. 2016, pp. 430-437.

Lambin et al., "Radiomics: Extracting More Information from Medical Images Using Advanced Feature Analysis," Eur J Cancer. Mar. 2012; 48(4): pp. 441-446.

Van Griethuysen et al., "Computational Radiomics System to Decode the Radiographic Phenotype," Cancer Res. Nov. 1, 2017; 77(21): e104-e107.

Ardila et al., "End-lo-End Lung Cancer Screening with Three-Dimensional Deep Learning on Low-Dose Chest Computed Tomography," Nature Medicine, vol. 25, Jun. 2019, pp. 954-961.

Baldwin et al., "External Validation of a Convolutional Neural Network Artificial Intelligence Tool to Predict Malginancy Pulmonary Nodules," Thorax 2020; 0:1-7.

Zheng et al., "Developing Global Image Feature Analysis Models to Predict Cancer Risk and Prognosis", Visual Computing for Industry, Biomedicine, and Art (2019) 2: 17; pp. 1-14 (Year: 2019).

Cherezov et al., "Delta Radiomic Features Improve Prediction for Lung Cancer Incidence: A Nested Case-Control Analysis of the National Lung Screening Trial", Cancer Medicine, Published by john Wiley & Sons Ltd. Cancer Medicine. 2018;7:6340-6356.

Dilger et al., "Improved Pulmonary Nodule Classification Utilizing Lung Parenchyma Texture Features," In Medical Imaging 2015: Computer-Aided Diagnosis, vol. 9414, pp. 700-709, SPIE (Mar. 2015).

Gould et al., "Evaluation of Individuals with Pulmonary Nodules: When is it Lung Cancer?—Diagnosis and Management of Lung Cancer, 3rd Edition: American College of Chest Physicians Evidence-Based Clinical Practice Guidelines," CHEST, vol. 143, No. 5, May 1, 2013, pp. e93s-e120s.

Huang et al., "Prediction of Lung Cancer Risk at Follow-Up Screening with Low-Dose CT: A Training and Validation Study of a Deep Learning Method," The Lancet, Digital Health, vol. 1, Nov. 2019, e353-e362.

International Search Report and Written Opinion mailed Apr. 7, 2021, PCT Application No. PCT/US2021/013571, 14 pages.

Jia et al., "Computer-Aided Diagnosis of Pulmonary Nodules on CT Scan Images," 2018 10th International Conference on Modelling, Identification and Control, ICMIC, Jul. 2-4, 2018, pp. 1-6.

Jirapatnakul et al., "Characterization of Solid Pulmonary Nodules using Three-Dimensional Features," In Medical Imaging 2007: Computer-Aided Diagnosis, vol. 6514, pp. 1054-1061, SPIE, (Mar. 2007).

Paul et al., "Predicting Malignant Nodules by Fusing Deep Features with Classical Radiomics Features", Journal of Medical Imaging 5(1), 011021 (Jan.-Mar. 2018), pp. 1-12 (Year: 2018).

Notice of Allowance from U.S. Appl. No. 17/150,063, dated Dec. 12, 2022, 8 pages.

(56) References Cited

OTHER PUBLICATIONS

Uthoff et al., "Machine Learning Approach for Distinguishing Malignant and Benign Lung Nodules Utilizing Standarized Perinodular Parenchymal Features from CT," Med. Phys., AIP, Melville, NY, vol. 46, No. 7, pp. 3207-3216.
Non-Final Office Action from U.S. Appl. No. 17/150,063, dated Aug. 18, 2022, 19 pages.
Non-Final Office Action from U.S. Appl. No. 18/529,511, dated Sep. 10, 2024, 9 pages.
Non-Final Office Action from U.S. Appl. No. 18/181,764, dated May 25, 2023, 21 pages.
Notice of Allowance, from U.S. Appl. No. 18/181,764, dated Aug. 29, 2023, 7 pages.
Decision to Grant from Japan Patent Application No. 2022-543684, dated Jan. 21, 2025, 4 pages.

* cited by examiner

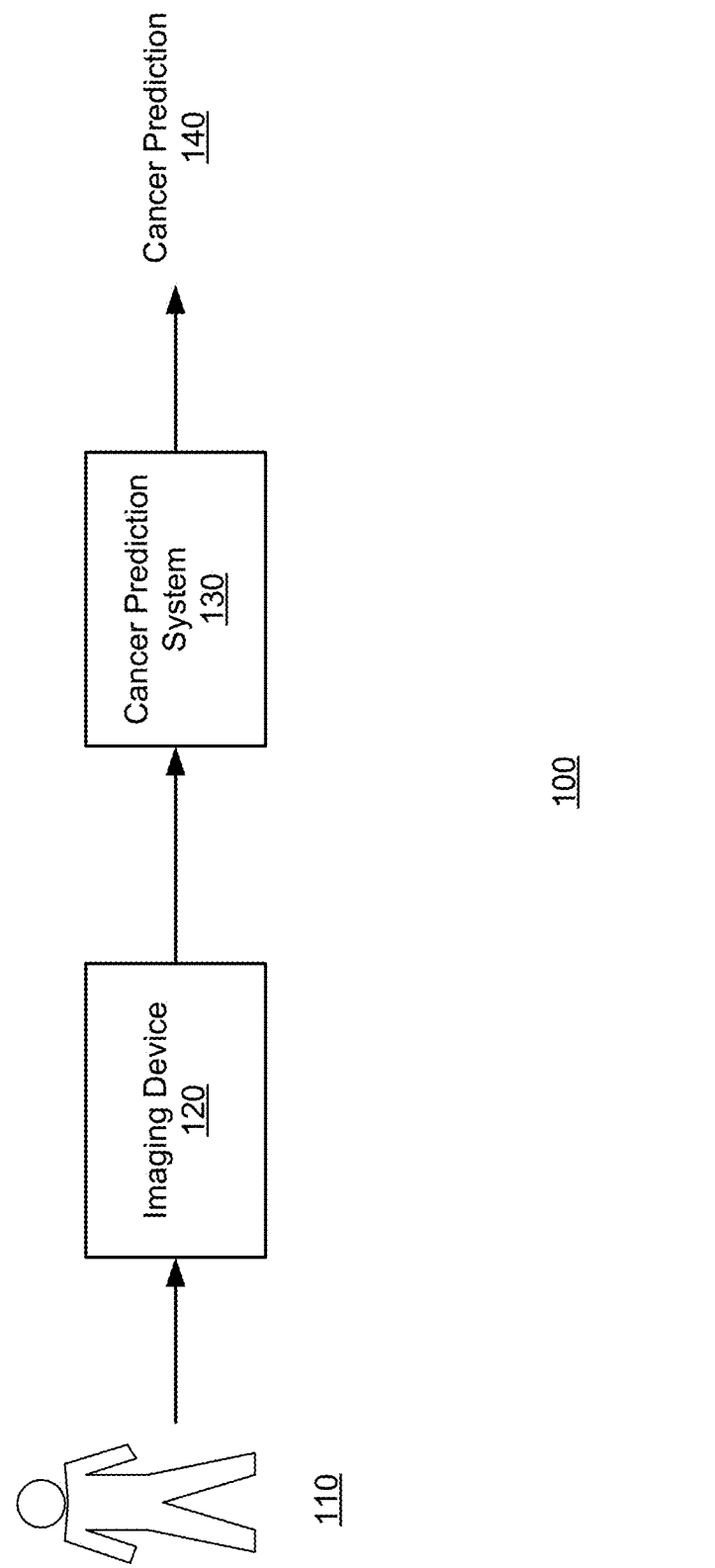

| Time Point | Time Horizon (years from time point) | Training/Testing | True Positives | True Negatives | False Positives | False Negatives | Sensitivity | Specificity | Positive Predictive Value | Negative Predictive Value | Predicted Positive Rate (Screen Percentage) after Exclusion Step | Incidence Rate without Enrollment after Exclusion Step | Predicted Positive Rate (Screen Percentage) of Entire (Testing/Training) Cohort | Incidence Rate without Enrollment of Entire (Testing/Training) Cohort | Odds Ratio | Optimal Cutpoint |
|---|---|---|---|---|---|---|---|---|---|---|---|---|---|---|---|---|
| t0 | | | | | | | | | | | | | | | | |
| t0 | 3 Years | Training Set | 93 | 6165 | 826 | 131 | 0.3679 | 0.8821 | 0.1771 | 0.9792 | 0.1042 | 0.0335 | 0.0858 | 0.0281 | 6.2437 | 0.0505 |
| t0 | 3 Years | Testing Set | 77 | 6149 | 658 | 141 | 0.3532 | 0.9033 | 0.1048 | 0.9776 | 0.1048 | 0.0311 | 0.0838 | 0.0287 | 5.0958 | 0.0506 |
| t1 | | | | | | | | | | | | | | | | |
| t1 | 3 Years | Training Set | 86 | 6283 | 635 | 98 | 0.4672 | 0.9086 | 0.0841 | 0.9845 | 0.1046 | 0.0235 | 0.0813 | 0.0204 | 6.5687 | 0.0495 |
| t1 | 3 Years | Testing Set | 66 | 6322 | 542 | 122 | 0.3511 | 0.9078 | 0.0862 | 0.9811 | 0.0880 | 0.0263 | 0.0885 | 0.0262 | 5.3273 | 0.0495 |
| t2 | | | | | | | | | | | | | | | | |
| t2 | 3 Years | Training Set | 63 | 6293 | 662 | 76 | 0.4460 | 0.9046 | 0.0869 | 0.9878 | 0.1022 | 0.0199 | 0.0869 | 0.0197 | 7.8788 | 0.0404 |
| t2 | 3 Years | Testing Set | 64 | 6346 | 593 | 95 | 0.3934 | 0.9146 | 0.0035 | 0.9853 | 0.0943 | 0.0220 | 0.0869 | 0.0209 | 6.6830 | 0.0404 |
| t1:t1 Random Sample from t0, t1, t2 (labelled t3) | | | | | | | | | | | | | | | | |
| t3 | 3 Years | Training Set | 99 | 6210 | 688 | 107 | 0.3706 | 0.9003 | 0.0869 | 0.9835 | 0.1063 | 0.0241 | 0.0964 | 0.0229 | 6.3145 | 0.0373 |
| t3 | 3 Years | Testing Set | 72 | 6190 | 741 | 111 | 0.3934 | 0.8970 | 0.0880 | 0.9824 | 0.1106 | 0.0268 | 0.0988 | 0.0257 | 6.4499 | 0.0373 |
| t2:t1:1 Random Sample from t0, t1, t2 (labelled t4) | | | | | | | | | | | | | | | | |
| t4 | 3 Years | Training Set | 91 | 6258 | 933 | 111 | 0.4719 | 0.8989 | 0.1134 | 0.9826 | 0.1036 | 0.0571 | 0.0890 | 0.0259 | 7.2861 | 0.0464 |
| t4 | 3 Years | Testing Set | 89 | 6215 | 680 | 114 | 0.4434 | 0.9072 | 0.1096 | 0.9868 | 0.1030 | 0.0275 | 0.0927 | 0.0273 | 6.7746 | 0.0464 |
| t1:1.2 Random Sample from t0, t1, t2 (labelled t5) | | | | | | | | | | | | | | | | |
| t5 | 3 Years | Training Set | 88 | 6209 | 636 | 98 | 0.4402 | 0.9093 | 0.0863 | 0.9848 | 0.1041 | 0.0236 | 0.0866 | 0.0234 | 6.2691 | 0.0430 |
| t5 | 3 Years | Testing Set | 68 | 6221 | 656 | 108 | 0.3840 | 0.9087 | 0.0844 | 0.9832 | 0.1056 | 0.0247 | 0.0866 | 0.0246 | 5.9551 | 0.0430 |

FIG. 7A

Demographics at timepoint t3

|  | Subgroup | Cancer Predicted | No Cancer Predicted |
|---|---|---|---|
| n |  | 416 | 3201 |
| Lung RADS (%) | 1 | 45 (10.8) | 561 (17.5) |
|  | 2 | 212 (51.0) | 2217 (69.3) |
|  | 3 | 29 (7.0) | 214 (6.7) |
|  | 4a | 86 (20.7) | 147 (4.6) |
|  | 4b | 44 (10.6) | 62 (1.9) |
| Age (mean (SD)) |  | 62.4 (5.0) | 61.8 (5.1) |
| Gender (%) | Female | 132 (31.7) | 1320 (41.2) |
|  | Male | 284 (68.3) | 1881 (58.8) |
| Smoking Status (%) | Current Smoker | 194 (46.6) | 1555 (48.6) |
|  | Former Smoker | 222 (53.4) | 1646 (51.4) |
| Pack Years (mean (SD)) |  | 60.5 (25.7) | 56.6 (23.8) |
| Cancer Diagnosed (%) | Cancer | 45 (10.8) | 93 (2.9) |
|  | No Cancer | 371 (89.2) | 3108 (97.1) |
| Cancer Stage (%) | N/A | 371 (89.2) | 3108 (97.1) |
|  | Stage IA | 19 (4.6) | 52 (1.6) |
|  | Stage IB | 6 (1.4) | 10 (0.3) |
|  | Stage IIA | 4 (1.0) | 7 (0.2) |
|  | Stage IIB | 3 (0.7) | 0 (0.0) |
|  | Stage IIIA | 3 (0.7) | 6 (0.2) |
|  | Stage IIIB | 1 (0.2) | 2 (0.1) |
|  | Stage IV | 7 (1.7) | 11 (0.3) |
|  | Unknown/Other | 2 (0.5) | 5 (0.2) |
| Cancer Cell Type (%) | Adenocarcinoma | 22 (5.3) | 54 (1.7) |
|  | N/A | 371 (89.2) | 3108 (97.1) |
|  | Neuroendocrine tumor | 4 (1.0) | 3 (0.1) |
|  | Non-small cell carcinoma, NOS | 4 (1.0) | 8 (0.2) |
|  | Other | 1 (0.2) | 1 (0.0) |
|  | Small cell carcinoma | 4 (1.0) | 6 (0.2) |
|  | Squamous cell carcinoma | 10 (2.4) | 21 (0.7) |

FIG. 7B

| Variable |
|---|
| application of wavelet filter high-low-low neighboring gray tone difference matrix coarseness - boundary volume |
| application of gaussian filter (sigma=1mm) 3d gray level run length matrix gray level non uniformity - interior volume |
| application of wavelet filter low-low-high gray level run length matrix gray level non uniformity - interior volume |
| application of wavelet filter high-low-high gray level size zone matrix zone entropy - interior volume |
| original (no filter) gray level size zone matrix gray level non uniformity - interior volume |
| application of wavelet filter hhl gray level size zone matrix gray level non uniformity - edge volume |
| original (no filter) gray level dependence matrix gray level non uniformity - interior volume |
| application of wavelet filter low-high-high gray level size zone matrix gray level non uniformity - interior volume |
| application of wavelet filter hhl gray level size zone matrix gray level non uniformity - interior volume |
| application of wavelet filter high-low-low gray level dependence matrix small dependence low gray level emphasis - interior volume |

Note:
Time point = t3, Time horizon = 3 (days if 69, months if 6, years if 1 or 3) from last imaging

FIG. 7E

| Variable |
|---|
| upper lower third low attenuation area ratio |
| subcutaneous fat sagittal cross sectional area |
| subcutaneous fat coronal cross sectional area |
| pectoralis major lean hounsfield units mode change |
| centrilobular emphysema mass |
| centrilobular emphysema perc15 |
| centrilobular emphysema volume |
| pectoralis major lean hounsfield units standard deviation change |
| normal parenchyma low attenuation area change |
| pectoralis major hounsfield units mode change |

Note:
Time point = t3, Time horizon = 3 (days if 69, months if 6, years if 1 or 3) from last imaging

Demographics at timepoint t3

| | Subgroup | Cancer Predicted | No Cancer Predicted |
|---|---|---|---|
| n | | 759 | 6328 |
| Lung RADS (%) | 1 | 87 (11.5) | 2893 (45.7) |
| | 2 | 425 (56.0) | 3033 (47.9) |
| | 3 | 76 (10.0) | 198 (3.1) |
| | 4a | 111 (14.6) | 148 (2.3) |
| | 4b | 60 (7.9) | 56 (0.9) |
| Age (mean (SD)) | | 62.5 (5.2) | 61.5 (5.0) |
| Gender (%) | Female | 255 (33.6) | 2596 (41.0) |
| | Male | 504 (66.4) | 3732 (59.0) |
| Smoking Status (%) | Current Smoker | 358 (47.2) | 2994 (47.3) |
| | Former Smoker | 401 (52.8) | 3334 (52.7) |
| Pack Years (mean (SD)) | | 60.6 (26.4) | 55.4 (23.1) |
| Cancer Diagnosed (%) | Cancer | 72 (9.5) | 111 (1.8) |
| | No Cancer | 687 (90.5) | 6217 (98.2) |
| Cancer Stage (%) | N/A | 687 (90.5) | 6217 (98.2) |
| | Stage IA | 32 (4.2) | 49 (0.8) |
| | Stage IB | 9 (1.2) | 7 (0.1) |
| | Stage IIA | 8 (1.1) | 5 (0.1) |
| | Stage IIB | 3 (0.4) | 1 (0.0) |
| | Stage IIIA | 5 (0.7) | 12 (0.2) |
| | Stage IIIB | 2 (0.3) | 6 (0.1) |
| | Stage IV | 8 (1.1) | 26 (0.4) |
| | Unknown/Other | 5 (0.7) | 5 (0.1) |
| Cancer Cell Type (%) | Adenocarcinoma | 42 (5.5) | 51 (0.8) |
| | N/A | 687 (90.5) | 6217 (98.2) |
| | Neuroendocrine tumor | 5 (0.7) | 6 (0.1) |
| | Non-small cell carcinoma, NOS | 5 (0.7) | 9 (0.1) |
| | Other | 1 (0.1) | 2 (0.0) |
| | Small cell carcinoma | 5 (0.7) | 15 (0.2) |
| | Squamous cell carcinoma | 14 (1.8) | 27 (0.4) |
| | Unknown | 0 (0.0) | 1 (0.0) |

FIG. 9B

| Variable | |
|---|---|
| | application of wavelet filter high-low-low neighboring gray tone difference matrix coarseness - edge volume of |
| | application of wavelet filter high-low-low gray level dependence matrix small dependence low gray level emphasis - interior volume of |
| | application of wavelet filter low-high-low neighboring gray tone difference matrix coarseness - edge volume of |
| | application of wavelet filter hhl gray level size zone matrix gray level non uniformity normalized - interior volume of |
| | application of wavelet filter low-low-high gray level run length matrix gray level non uniformity - edge volume of |
| | application of gaussian filter (sigma=1mm) 3d neighboring gray tone difference matrix coarseness - edge volume of |
| | original (no filter) gray level dependence matrix small dependence low gray level emphasis - interior volume of |
| | application of wavelet filter hhl gray level dependence matrix gray level non uniformity - boundary volume of |
| | application of wavelet filter low-low-high gray tone difference matrix coarseness - edge volume of |
| | application of wavelet filter low-low-low gray level run length matrix gray level non uniformity - interior volume of |

| Note: | |
|---|---|
| | Time point = t3, Time horizon = 3 (days if 69, months if 6, years if 1 or 3) from last imaging |

FIG. 9E

T1 Demographics – Lung-Rads 1-3 Only

Demographics at timepoint t1 for 3 (days if 69, months if 6, years if 1, 3 or 5)

| | Subgroup | Cancer Predicted | No Cancer Predicted |
|---|---|---|---|
| n | | 250 | 2004 |
| Lung RADS (%) | 1 | 32 (12.8) | 424 (21.2) |
| | 2 | 215 (86.0) | 1556 (77.6) |
| | 3 | 3 (1.2) | 24 (1.2) |
| Age (mean (SD)) | | 62.0 (6.2) | 61.7 (6.0) |
| Gender (%) | Female | 97 (38.8) | 787 (39.3) |
| | Male | 153 (61.2) | 1217 (60.7) |
| Smoking Status (%) | Current Smoker | 118 (47.2) | 987 (49.3) |
| | Former Smoker | 132 (52.8) | 1017 (50.7) |
| Pack Years (mean (SD)) | | 58.0 (23.5) | 56.4 (23.4) |
| Cancer Diagnosed (%) | Cancer | 34 (13.6) | 46 (2.3) |
| | No Cancer | 216 (86.4) | 1958 (97.7) |
| Cancer Stage (%) | N/A | 216 (86.4) | 1958 (97.7) |
| | Stage IA | 17 (6.8) | 27 (1.3) |
| | Stage IB | 4 (1.6) | 3 (0.1) |
| | Stage IIA | 6 (2.4) | 4 (0.2) |
| | Stage IIIA | 3 (1.2) | 4 (0.2) |
| | Stage IIIB | 2 (0.8) | 1 (0.0) |
| | Stage IV | 2 (0.8) | 6 (0.3) |
| | Unknown/Other | 0 (0.0) | 1 (0.0) |
| Cancer Cell Type (%) | Adenocarcinoma | 20 (8.0) | 23 (1.1) |
| | N/A | 216 (86.4) | 1958 (97.7) |
| | Neuroendocrine tumor | 3 (1.2) | 1 (0.0) |
| | Non-small cell carcinoma, NOS | 2 (0.8) | 5 (0.2) |
| | Other | 1 (0.4) | 0 (0.0) |
| | Small cell carcinoma | 2 (0.8) | 3 (0.1) |
| | Squamous cell carcinoma | 6 (2.4) | 14 (0.7) |

FIG. 10A

| Variable |
|---|
| original (no filter) gray level size zone matrix gray level non uniformity - edge volume change |
| application of wavelet filter high-low-low gray level run length matrix gray level non uniformity - boundary volume change |
| original (no filter) shape least axis length - boundary volume change |
| application of wavelet filter high-high-high gray level dependence matrix gray level non uniformity - interior volume change |
| original (no filter) shape sphericity - boundary volume change |
| application of wavelet filter low-low-low gray level run length matrix run length matrix run length entropy - edge volume change |
| application of wavelet filter high-low-low gray level dependence matrix gray level non uniformity - interior volume change |
| application of wavelet filter low-high-low gray level size zone matrix gray level non uniformity - interior volume change |
| original (no filter) shape major axis length - edge volume change |
| application of wavelet filter high-low-low gray level run length matrix gray level non uniformity - interior volume change |

Note:
Time point = t1, Time horizon = 3 (days if 69, months if 6, years if 1 or 3) from last imaging

FIG. 10D

| Variable |
|---|
| centrilobular emphysema las905 |
| centrilobular emphysema low attenuation area |
| whole lung volume |
| centrilobular emphysema las910 |
| wildcard volume |
| centrilobular emphysema perc15 |
| centrilobular emphysema las875 |
| centrilobular emphysema las925 |
| centrilobular emphysema hounsfield units mean |
| centrilobular emphysema las856 |

Note:
Time point = 11, Time horizon = 3 (days if 69, months if 6, years if 1 or 3) from last imaging

FIG. 10E

Demographics at timepoint t2 for 3 (days if 59, months if 6; years if 1, 3 or 5)

| | Subgroup | Cancer Predicted | No Cancer Predicted |
|---|---|---|---|
| n | | 621 | 6264 |
| Lung RADS (%) | 1 | 89 (14.3) | 2705 (43.2) |
| | 2 | 521 (83.9) | 3513 (56.1) |
| | 3 | 11 (1.8) | 46 (0.7) |
| Age (mean (SD)) | | 63.1 (6.1) | 61.3 (6.0) |
| Gender (%) | Female | 169 (27.2) | 2604 (41.6) |
| | Male | 452 (72.8) | 3660 (58.4) |
| Smoking Status (%) | Current Smoker | 268 (43.2) | 2955 (47.2) |
| | Former Smoker | 353 (56.8) | 3309 (52.8) |
| Pack Years (mean (SD)) | | 61.6 (26.1) | 55.2 (23.2) |
| Cancer Diagnosed (%) | Cancer | 39 (6.3) | 83 (1.3) |
| | No Cancer | 582 (93.7) | 6181 (98.7) |
| Cancer Stage (%) | N/A | 582 (93.7) | 6181 (98.7) |
| | Stage IA | 13 (2.1) | 24 (0.4) |
| | Stage IB | 3 (0.5) | 3 (0.0) |
| | Stage IIA | 4 (0.6) | 1 (0.0) |
| | Stage IIB | 4 (0.6) | 2 (0.0) |
| | Stage IIIA | 4 (0.6) | 14 (0.2) |
| | Stage IIIB | 0 (0.0) | 5 (0.1) |
| | Stage IV | 7 (1.1) | 31 (0.5) |
| | Unknown/Other | 4 (0.6) | 3 (0.0) |
| Cancer Cell Type (%) | Adenocarcinoma | 12 (1.9) | 28 (0.4) |
| | N/A | 582 (93.7) | 6181 (98.7) |
| | Neuroendocrine tumor | 1 (0.2) | 4 (0.1) |
| | Non-small cell carcinoma, NOS | 7 (1.1) | 5 (0.1) |
| | Other | 0 (0.0) | 3 (0.0) |
| | Small cell carcinoma | 5 (0.8) | 21 (0.3) |
| | Squamous cell carcinoma | 13 (2.1) | 22 (0.4) |
| | Unknown | 1 (0.2) | 0 (0.0) |

FIG. 11A

| Variable |
|---|
| application of wavelet filter low-high-low gray level run length matrix low gray level run emphasis - interior volume |
| application of wavelet filter high-high-high gray level run length matrix gray level non uniformity - edge volume |
| application of wavelet filter low-low-low gray level size zone matrix gray level non uniformity - interior volume |
| application of wavelet filter low-high-low gray level run length matrix short run low gray level emphasis - interior volume |
| application of wavelet filter high-high-high gray level run length matrix run entropy - edge volume |
| original (no filter) shape mesh volume - boundary volume |
| application of wavelet filter high-high-high gray level run length matrix gray level non uniformity - boundary volume |
| application of wavelet filter low-high-low gray level dependence matrix low gray level emphasis - interior volume |
| original (no filter) shape maximum 2d diameter column - boundary volume |
| application of wavelet filter low-low-high gray level run length matrix gray level non uniformity - edge volume |

Note:
Time point = t2, Time horizon = 3 (days if 69, months if 6, years if 1 or 3) from last imaging

FIG. 11D

| Variable |
|---|
| centrilobular emphysema volume |
| centrilobular emphysema - percentage of lung |
| upper lower third low attenuation area ratio |
| normal parenchyma - percentage of lung |
| wildcard high attenuation area 250 change |
| whole lung high attenuation area 250 change |
| subcutaneous fat hounsfield units skewness change |
| subcutaneous fat lean hounsfield units mean change |
| normal parenchyma hounsfield units standard deviation 500 |
| centrilobular emphysema mass |

Note:
Time point = t2. Time horizon = 3 (days if 69, months if 6, years if 1 or 3) from last imaging

FIG. 11E

Demographics at timepoint t0 for 3 (days if 69, months if 6; years if 1, 3 or 5)

| | Subgroup | Cancer Predicted | No Cancer Predicted |
|---|---|---|---|
| n | | 595 | 5972 |
| Lung RADS (%) | 1 | 316 (53.1) | 2935 (49.1) |
| | 2 | 215 (36.1) | 2485 (41.6) |
| | 3 | 64 (10.8) | 552 (9.2) |
| Age (mean (SD)) | | 63.1 (5.3) | 61.4 (5.0) |
| Gender (%) | Female | 165 (27.7) | 2504 (41.9) |
| | Male | 430 (72.3) | 3468 (58.1) |
| Smoking Status (%) | Current Smoker | 283 (47.6) | 2833 (47.4) |
| | Former Smoker | 312 (52.4) | 3139 (52.6) |
| Pack Years (mean (SD)) | | 61.2 (25.3) | 55.4 (23.4) |
| Cancer Diagnosed (%) | Cancer | 32 (5.4) | 138 (2.3) |
| | No Cancer | 563 (94.6) | 5834 (97.7) |
| Cancer Stage (%) | N/A | 563 (94.6) | 5834 (97.7) |
| | Stage IA | 18 (3.0) | 62 (1.0) |
| | Stage IB | 0 (0.0) | 13 (0.2) |
| | Stage IIA | 3 (0.5) | 11 (0.2) |
| | Stage IIIA | 2 (0.3) | 13 (0.2) |
| | Stage IIIB | 2 (0.3) | 5 (0.1) |
| | Stage IV | 6 (1.0) | 27 (0.5) |
| | Unknown/Other | 1 (0.2) | 7 (0.1) |
| Cancer Cell Type (%) | Adenocarcinoma | 9 (1.5) | 76 (1.3) |
| | N/A | 563 (94.6) | 5834 (97.7) |
| | Neuroendocrine tumor | 2 (0.3) | 5 (0.1) |
| | Non-small cell carcinoma, NOS | 4 (0.7) | 12 (0.2) |
| | Other | 0 (0.0) | 3 (0.1) |
| | Small cell carcinoma | 6 (1.0) | 19 (0.3) |
| | Squamous cell carcinoma | 11 (1.8) | 22 (0.4) |
| | Unknown | 0 (0.0) | 1 (0.0) |

FIG. 12A

| Variable |
|---|
| application of gaussian filter (sigma=1mm) 3d neighboring gray tone difference matrix coarseness - boundary volume |
| application of wavelet filter HH gray level size zone matrix zone entropy - interior volume |
| application of wavelet filter low-high-high gray level dependence matrix gray level non uniformity - boundary volume |
| original (no filter) shape maximum3d diameter - interior volume |
| application of wavelet filter high-low-low gray level run length matrix low gray level run emphasis - interior volume |
| application of wavelet filter high-low-low gray level dependence matrix dependence entropy - interior volume |
| original (no filter) shape maximum2d diameter row - boundary volume |
| application of wavelet filter HH gray level size zone matrix gray level non uniformity - edge volume |
| application of wavelet filter high-low-low gray level size zone matrix gray level non uniformity - edge volume |
| application of wavelet filter low-high-high neighboring gray tone difference matrix coarseness - edge volume |

Note

Time point = 10, Time horizon = 3 (days if 69, months if 6, years if 1 or 3) from last imaging

FIG. 12D

| Variable |
|---|
| subcutaneous fat coronal cross sectional area |
| centrilobular emphysema high attenuation area 800 |
| centrilobular emphysema high attenuation area 700 |
| subcutaneous fat sagittal cross sectional area |
| centrilobular emphysema perc10 |
| centrilobular emphysema low attenuation area |
| emphysematous - percentage of lung |
| centrilobular emphysema perc15 |
| upper lower third low attenuation area ratio |
| centrilobular emphysema hounsfield units mean500 |

Note:
Time point = 0, Time horizon = 3 (days if 69, months if 6, years if 1 or 3) from last imaging

FIG. 12E

|  | Subgroup | Cancer Predicted | No Cancer Predicted |
| --- | --- | --- | --- |
| n |  | 174 | 3850 |
| Lung RADS (%) | 2 | 49 (28.2) | 2767 (71.9) |
|  | 3 | 44 (25.3) | 617 (16.0) |
|  | 4a | 52 (29.9) | 345 (9.0) |
|  | 4b | 29 (16.7) | 121 (3.1) |
| Age (mean (SD)) |  | 63.9 (5.2) | 61.8 (5.1) |
| Gender (%) | Female | 64 (36.8) | 1630 (42.3) |
|  | Male | 110 (63.2) | 2220 (57.7) |
| Smoking Status (%) | Current Smoker | 93 (53.4) | 1861 (48.3) |
|  | Former Smoker | 81 (46.6) | 1989 (51.7) |
| Pack Years (mean (SD)) |  | 63.5 (25.8) | 56.4 (23.9) |
| Cancer Diagnosed (%) | Cancer | 25 (14.4) | 71 (1.8) |
|  | No Cancer | 149 (85.6) | 3779 (98.2) |
| Cancer Stage (%) | Stage IA | 13 (52.0) | 32 (45.1) |
|  | Stage IB | 4 (16.0) | 3 (4.2) |
|  | Stage IIA | 3 (12.0) | 5 (7.0) |
|  | Stage IIB | 1 (4.0) | 0 (0.0) |
|  | Stage IIIA | 3 (12.0) | 13 (18.3) |
|  | Stage IIIB | 0 (0.0) | 3 (4.2) |
|  | Stage IV | 1 (4.0) | 13 (18.3) |
|  | Unknown/Other | 0 (0.0) | 2 (2.8) |
| Cancer Cell Type (%) | Adenocarcinoma | 16 (64.0) | 42 (59.2) |
|  | Neuroendocrine tumor | 1 (4.0) | 5 (7.0) |
|  | Non-small cell carcinoma, NOS | 3 (12.0) | 6 (8.5) |
|  | Other | 0 (0.0) | 2 (2.8) |
|  | Small cell carcinoma | 0 (0.0) | 4 (5.6) |
|  | Squamous cell carcinoma | 5 (20.0) | 12 (16.9) |

FIG. 13B

| | Estimate | Confidence Interval | |
|---|---|---|---|
| | | Lower Bound | Upper Bound |
| Apparent Prevalence | 0.043 | 0.037 | 0.050 |
| True Prevalence | 0.024 | 0.019 | 0.029 |
| Sensitivity | 0.250 | 0.176 | 0.360 |
| Specificity | 0.962 | 0.956 | 0.966 |
| Diagnostic Accuracy | 0.945 | 0.938 | 0.952 |
| Diagnostic Odds Ratio | 8.930 | 5.502 | 14.495 |
| Number Needed to Screen | 4.495 | 3.051 | 7.589 |
| Youden's Index | 0.222 | 0.132 | 0.320 |
| Positive Predictive Value | 0.144 | 0.095 | 0.205 |
| Negative Predictive Value | 0.982 | 0.977 | 0.986 |
| Likelihood Ratio of Positive Test | 6.605 | 4.702 | 9.280 |
| Likelihood Ratio of Negative Test | 0.780 | 0.665 | 0.866 |
| Proportion Ruled Out | 0.957 | 0.950 | 0.963 |
| Proportion Ruled In | 0.043 | 0.037 | 0.050 |
| False Positives | 0.038 | 0.032 | 0.044 |
| False Negatives | 0.740 | 0.640 | 0.824 |

FIG. 13C

SYSTEM AND METHOD FOR PREDICTING THE RISK OF FUTURE LUNG CANCER

CROSS-REFERENCE TO RELATED APPLICATIONS

This application claims the benefit of and priority to U.S. Provisional Patent Application No. 63/222,712 filed Jul. 16, 2021 and U.S. Provisional Patent Application No. 63/328,590 filed Apr. 7, 2022, the entire disclosure of each of which is hereby incorporated by reference in its entirety for all purposes.

BACKGROUND

Lung cancer most commonly begins with the development of a lung nodule. A nodule may be cancerous or may be a benign overgrowth of tissue that subsequently undergoes malignant transformation. Over the past decade, extensive work by the medical community has shown that in certain patient populations, annual lung cancer screening using computed tomography of the chest (chest CT) results in the earlier identification of lung nodules and decreases mortality related to lung cancer. While the radiologic community has made great strides in creating clinical scoring systems that identify high risk lung nodules, true prevention of lung cancer has been limited by inability to identify patients at highest risk for the disease.

For example, the Lung CT screening, Reporting and Data System (Lung-RADS) scoring system currently utilized by radiologists is based upon the size of the nodule, the rate of growth of the nodule and the appearance of the nodule. Generally, the larger the nodule, the more rapid its growth or the more irregular it is in appearance, the more likely it is to be cancer. This system is well suited to identifying which patients that may benefit from immediate intervention such as lung biopsy or surgery. However, it does not determine the longer-term risk of for future malignancy. Thus, additional tools are needed to identify patients at highest risk for developing lung cancer in the future.

SUMMARY

Embodiments disclosed herein involve implementing risk predictions models to analyze images (e.g., CT scans) for predicting risk of lung cancer (e.g., existing or prevalent risk of cancer or future risk of developing cancer). Risk prediction models analyze features extracted from images, such as nodule specific features and non-nodule specific features. In various embodiments, inclusion of non-nodule specific features in the risk prediction model has the benefit of enabling the risk prediction models to generate future risk of cancer predictions for subjects that do not yet have a lung nodule. As one example, by analyzing nodule specific features and/or non-nodule specific features, examples of which include lung parenchyma features and/or body composition features, risk prediction models can be implemented for the early detection of lung cancer prior to the development of a lung nodule. As another example, by analyzing nodule specific features and/or non-nodule specific features, examples of which include lung parenchyma features and/or body composition features, risk prediction models can be implemented for discriminating nodules (e.g., benign v. malignant nodules or healthy v. cancerous nodules). In various embodiments, risk prediction models analyze longitudinal features extracted from images, such as longitudinal nodule specific features and longitudinal non-nodule specific features. Longitudinal features are derived from two or more images captured from different time points and therefore, refer to changes in features across the different time points. Thus, risk prediction models can be implemented for monitoring patients over time periods for early detection of the development of cancer.

Disclosed herein is a method for predicting one or more risks of lung cancer for a subject, the method comprising: obtaining one or more images captured from the subject; extracting features from the one or more obtained images, the extracted features comprising at least non-nodule specific features, wherein the non-nodule specific features comprise one or more of a lung parenchyma feature, a body composition feature, a longitudinal lung parenchyma feature, or a longitudinal body composition feature; and predicting one or more risks of lung cancer for the subject by applying one or more trained risk prediction models to analyze the extracted features from the one or more obtained images. In various embodiments, the non-nodule features comprise the longitudinal lung parenchyma feature and the longitudinal body composition feature.

In various embodiments, the non-nodule features comprise each of the lung parenchyma feature, the body composition feature, the longitudinal lung parenchyma feature, and the longitudinal body composition feature. In various embodiments, the lung parenchyma feature comprise one or more of densitometric measures of the lung parenchyma or local histogram measures of the lung parenchyma. In various embodiments, the longitudinal lung parenchyma feature comprise one or more of a change in densitometric measures of the lung parenchyma or a change in local histogram measures of the lung parenchyma. In various embodiments, the densitometric measures of the lung parenchyma comprise one or more of: percentage of low attenuation area of the lung, percentage of high attenuation area of the lung, and ratio of low attenuation or high attenuation area in an upper lung zone in comparison to a lower lung zone. In various embodiments, the local histogram measures of the lung parenchyma comprise one or more percentage(s) of lung occupied by any of normal tissue, centrilobular emphysema, centrilobular nodule, ground glass, honeycombing, linear scar, nodular, reticular, subpleural line, other emphysema, or cyst. In various embodiments, the body composition feature comprises one or more of pectoralis cross-sectional area, pectoralis lean cross-sectional area, or sub-cutaneous fat cross-sectional area.

In various embodiments, the longitudinal body composition feature comprises one or more of a change in pectoralis cross-sectional area, a change in pectoralis lean cross-sectional area, or a change in sub-cutaneous fat cross-sectional area. In various embodiments, the one or more risks of lung cancer comprise a risk of existing or prevalent cancer. In various embodiments, the one or more risks of lung cancer comprise a future risk of developing cancer. In various embodiments, the extracted features further comprise nodule specific features. In various embodiments, the nodule specific features comprise longitudinal nodule specific features. In various embodiments, the nodule specific features comprise one or more of nodule specific attenuation, nodule margin description, nodule size, nodule shape, nodule texture, nodule diameter, Lung-RADS score, or radiomic features. In various embodiments, the longitudinal nodule specific features comprise one or more of a change in nodule specific attenuation, a change in nodule margin description, a change in nodule size, a change in nodule shape, a change in nodule texture, a change in nodule diameter, a change in Lung-RADS score, or a change in radiomic features. In various embodiments, radiomic features comprise one or more of first order statistics, 3D shape based features, 2D shape based features, gray level co-occurrence matrix, gray level run length matrix, gray level size zone matrix, neighboring gray tone difference matrix, and gray level dependence matrix.

In various embodiments, the nodule specific features are extracted from a radiologist report. In various embodiments, the nodule specific features are computationally extracted by implementing an image analysis algorithm. In various embodiments, predicting the one or more risks of lung cancer for the subject comprises applying a risk prediction model that comprises: a first submodel configured to analyze the non-nodule specific features; and a second submodel configured to analyze the nodule specific features.

In various embodiments, the risk prediction model further comprises a third submodel configured to analyze predicted outputs of the first submodel and the second submodel to predict a risk of lung cancer for the subject. In various embodiments, predicting the one or more risks of lung cancer for the subject comprises applying a 5 year risk prediction model to predict whether the subject is likely to develop lung cancer within 5 years. In various embodiments, predicting the one or more risks of lung cancer for the subject comprises applying a 3 year risk prediction model to predict whether the subject is likely to develop lung cancer within 3 years. In various embodiments, two or more of the top 10 important features of the first submodel of the risk prediction model are longitudinal lung parenchyma features or longitudinal body composition features. In various embodiments, three or more of the top 10 important features of the first submodel of the risk prediction model are longitudinal lung parenchyma features or longitudinal body composition features. In various embodiments, four or more of the top 10 important features of the first submodel of the risk prediction model are longitudinal lung parenchyma features or longitudinal body composition features. In various embodiments, two or more of the top 10 important features of the first submodel of the risk prediction model are lung parenchyma features or body composition features. In various embodiments, three or more of the top 10 important features of the first submodel of the risk prediction model are lung parenchyma features or body composition features. In various embodiments, four or more of the top 10 important features of the first submodel of the risk prediction model are lung parenchyma features or body composition features.

In various embodiments, the 3 year risk prediction model exhibits an area under the curve (AUC) value of at least 0.70. In various embodiments, the 3 year risk prediction model exhibits an odds ratio of at least 5.0. In various embodiments, predicting the one or more risks of lung cancer for the subject comprises applying a 1 year risk prediction model to predict whether the subject is likely to develop lung cancer within 1 year. In various embodiments, determining that the subject is a candidate comprises obtaining a classification of the subject in one of Lung-RADS 1, Lung-RADS 2, Lung-RADS 3, Lung-RADS 4A, or Lung-RADS 4B.

In various embodiments, predicting the one or more risks of lung cancer for the subject comprises applying a risk prediction model that is configured to analyze together the nodule specific features and non-nodule specific features. In various embodiments, predicting the one or more risks of lung cancer for the subject comprises applying multiple risk prediction models to predict whether the subject is likely to develop lung cancer within N different time periods. In various embodiments, at least one of the N different time periods is any one of 0 months, 1 month, 2 months, 3 months, 4 months, 5 months, 6 months, 7 months, 8 months, 9 months, 10 months, 11 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. In various embodiments, N is 1, 2, 3, 4, 5, 6, 7, 8, 9, 10, 11, 12, 13, 14, 15, 16, 17, 18, 19, or 20 different time periods. In various embodiments, one of the one or more risk prediction models is trained to predict the risk of lung cancer using training images captured from a training cohort of training individuals classified in any of Lung-RADS 1, Lung-RADS 1-2, Lung-RADS 1-3, Lung-RADS 1-4A, or Lung-RADS 1-4B. In various embodiments, one of the one or more risk prediction models is trained to predict the risk of lung cancer using training images captured from a training cohort of training individuals classified in Lung-RADS 1-3. In various embodiments, a majority of training individuals in the training cohort are previously classified in Lung-RADS 1.

In various embodiments, the one or more images are computed tomography (CT) images or X-ray images. In various embodiments, the one or more images comprises are thoracic CT images or chest X-ray images. In various embodiments, the one or more images comprise at least a first image captured from the subject at a first timepoint and at least a second image captured from the subject at a second timepoint. In various embodiments, the risk prediction model is trained using training images of the National Lung Screening Trial (NLST).

In various embodiments, methods disclosed herein further comprise: prior to predicting one or more risks of lung cancer for the subject: obtaining nodule-specific features corresponding to the subject; determining that the subject is a candidate for risk prediction based on the nodule-specific features. In various embodiments, determining that the subject is a candidate comprises determining that the subject does not have lung cancer or is at low-risk of developing lung cancer. In various embodiments, determining that the subject is at low-risk of developing lung cancer comprises determining that the subject does not have a nodule based on the nodule-specific features. In various embodiments, the lung cancer is either non-small cell lung cancer or small cell lung cancer. In various embodiments, the lung cancer is either adenocarcinoma or squamous cell carcinoma.

In various embodiments, methods disclosed herein further comprise selecting a clinical response for the subject based on the predicted risk of lung cancer. In various embodiments, selecting a clinical response for the subject comprises selecting an intervention for treating the subject. In various embodiments, selecting an intervention comprises selecting a therapeutic for administration to the subject. In various embodiments, the selected therapeutic is prophylactically administered to the subject to delay or prevent the development of the lung cancer. In various embodiments, the clinical response comprises providing counseling to the subject to modify behavior of the subject. In various embodiments, the clinical response comprises increasing a frequency of follow up for the subject. In various embodiments, the clinical response comprises performing or scheduling to be performed an additional risk prediction test to confirm the predicted risk of lung cancer. In various embodiments, one or more of the trained risk prediction models are one of a random forest model or gradient boosted model.

Additionally disclosed herein is a non-transitory computer readable medium for predicting one or more risks of lung cancer for a subject, the non-transitory computer readable medium comprising instructions that, when executed by a processor, cause the processor to: obtain one or more images captured from the subject; extract features from the one or more obtained images, the extracted features comprising at least non-nodule specific features, wherein the non-nodule specific features comprise one or more of a lung parenchyma feature, a body composition feature, a longitudinal lung parenchyma feature, or a longitudinal body composition feature; and predict one or more risks of lung cancer for the subject by applying one or more trained risk prediction models to analyze the extracted features from the one or more obtained images.

In various embodiments, the non-nodule features comprise the longitudinal lung parenchyma feature and the longitudinal body composition feature. In various embodiments, the non-nodule features comprise each of the lung parenchyma feature, the body composition feature, the longitudinal lung parenchyma feature, and the longitudinal body composition feature. In various embodiments, the lung parenchyma feature comprise one or more of densitometric measures of the lung parenchyma or local histogram measures of the lung parenchyma. In various embodiments, the longitudinal lung parenchyma feature comprise one or more of a change in densitometric measures of the lung parenchyma or a change in local histogram measures of the lung parenchyma. In various embodiments, the densitometric measures of the lung parenchyma comprise one or more of: percentage of low attenuation area of the lung, percentage of high attenuation area of the lung, and ratio of low attenuation or high attenuation area in an upper lung zone in comparison to a lower lung zone. In various embodiments, the local histogram measures of the lung parenchyma comprise one or more percentage(s) of lung occupied by any of normal tissue, centrilobular emphysema, centrilobular nodule, ground glass, honeycombing, linear scar, nodular, reticular, subpleural line, other emphysema, or cyst. In various embodiments, the body composition feature comprises one or more of pectoralis cross-sectional area, pectoralis lean cross-sectional area, or sub-cutaneous fat cross-sectional area. In various embodiments, the longitudinal body composition feature comprises one or more of a change in pectoralis cross-sectional area, a change in pectoralis lean cross-sectional area, or a change in sub-cutaneous fat cross-sectional area.

In various embodiments, the one or more risks of lung cancer comprise a risk of existing or prevalent cancer. In various embodiments, the one or more risks of lung cancer comprise a future risk of developing cancer. In various embodiments, the extracted features further comprise nodule specific features. In various embodiments, the nodule specific features comprise longitudinal nodule specific features. In various embodiments, the nodule specific features comprise one or more of nodule specific attenuation, nodule margin description, nodule size, nodule shape, nodule texture, nodule diameter, Lung-RADS score, or radiomic features. In various embodiments, the longitudinal nodule specific features comprise one or more of a change in nodule specific attenuation, a change in nodule margin description, a change in nodule size, a change in nodule shape, a change in nodule texture, a change in nodule diameter, a change in Lung-RADS score, or a change in radiomic features. In various embodiments, radiomic features comprise one or more of first order statistics, 3D shape based features, 2D shape based features, gray level co-occurrence matrix, gray level run length matrix, gray level size zone matrix, neighboring gray tone difference matrix, and gray level dependence matrix. In various embodiments, the nodule specific features are extracted from a radiologist report. In various embodiments, the nodule specific features are computationally extracted by implementing an image analysis algorithm.

In various embodiments, the instructions that cause the processor to predict the one or more risks of lung cancer for the subject further comprises instructions that, when executed by the processor, cause the processor to apply a risk prediction model that comprises: a first submodel configured to analyze the non-nodule specific features; and a second submodel configured to analyze the nodule specific features. In various embodiments, the risk prediction model further comprises a third submodel configured to analyze predicted outputs of the first submodel and the second submodel to predict a risk of lung cancer for the subject. In various embodiments, the instructions that cause the processor to predict the one or more risks of lung cancer for the subject comprises instructions that, when executed by the processor, cause the processor to apply a 5 year risk prediction model to predict whether the subject is likely to develop lung cancer within 5 years. In various embodiments, the instructions that cause the processor to predict the one or more risks of lung cancer for the subject comprises instructions that, when executed by the processor, cause the processor to apply a 3 year risk prediction model to predict whether the subject is likely to develop lung cancer within 3 years. In various embodiments, two or more of the top 10 important features of the first submodel of the risk prediction model are longitudinal lung parenchyma features or longitudinal body composition features. In various embodiments, three or more of the top 10 important features of the first submodel of the risk prediction model are longitudinal lung parenchyma features or longitudinal body composition features. In various embodiments, four or more of the top 10 important features of the first submodel of the risk prediction model are longitudinal lung parenchyma features or longitudinal body composition features. In various embodiments, two or more of the top 10 important features of the first submodel of the risk prediction model are lung parenchyma features or body composition features. In various embodiments, three or more of the top 10 important features of the first submodel of the risk prediction model are lung parenchyma features or body composition features. In various embodiments, four or more of the top 10 important features of the first submodel of the risk prediction model are lung parenchyma features or body composition features.

In various embodiments, the 3 year risk prediction model exhibits an area under the curve (AUC) value of at least 0.70. In various embodiments, the 3 year risk prediction model exhibits an odds ratio of at least 5.0. In various embodiments, the instructions that cause the processor to predict the one or more risks of lung cancer for the subject comprises instructions that, when executed by the processor, cause the processor to apply a 1 year risk prediction model to predict whether the subject is likely to develop lung cancer within 1 year. In various embodiments, the instructions that cause the processor to determine that the subject is a candidate further comprises instructions that, when executed by the processor, cause the processor to obtain a classification of the subject in one of Lung-RADS 1, Lung-RADS 2, Lung-RADS 3, Lung-RADS 4A, or Lung-RADS 4B. In various embodiments, the instructions that cause the processor to predict the one or more risks of lung cancer for the subject further comprises instructions that, when executed by the processor, cause the processor to apply a risk prediction model that is configured to analyze together the nodule specific features and non-nodule specific features.

In various embodiments, predicting the one or more risks of lung cancer for the subject comprises applying multiple risk prediction models to predict whether the subject is likely to develop lung cancer within N different time periods. In various embodiments, at least one of the N different time periods is any one of 0 months, 1 month, 2 months, 3 months, 4 months, 5 months, 6 months, 7 months, 8 months, 9 months, 10 months, 11 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. In various embodiments, N is 1, 2, 3, 4, 5, 6, 7, 8, 9, 10, 11, 12, 13, 14, 15, 16, 17, 18, 19, or 20 different time periods. In various embodiments, one of the one or more risk prediction models is trained to predict the risk of lung cancer using training images captured from a training cohort of training individuals classified in any of Lung-RADS 1, Lung-RADS 1-2, Lung-RADS 1-3, Lung-RADS 1-4A, or Lung-RADS 1-4B. In various embodiments, one of the one or more risk prediction models is trained to predict the risk of lung cancer using training images captured from a training cohort of training individuals classified in Lung-RADS 1-3. In various embodiments, a majority of training individuals in the training cohort are previously classified in Lung-RADS 1.

In various embodiments, the one or more images are computed tomography (CT) images or X-ray images. In various embodiments, the one or more images comprises are thoracic CT images or chest X-ray images. In various embodiments, the one or more images comprise at least a first image captured from the subject at a first timepoint and at least a second image captured from the subject at a second timepoint. In various embodiments, the risk prediction model is trained using training images of the National Lung Screening Trial (NLST). In various embodiments, the non-transitory computer readable medium further comprises instructions that, when executed by a processor, cause the processor to: prior to predicting one or more risks of lung cancer for the subject: obtain nodule-specific features corresponding to the subject; determine that the subject is a candidate for risk prediction based on the nodule-specific features. In various embodiments, the instructions that cause the processor to determine that the subject is a candidate further comprises instructions that, when executed by the processor, cause the processor to determine that the subject does not have lung cancer or is at low-risk of developing lung cancer. In various embodiments, the instructions that cause the processor to determine that the subject is at low-risk of developing lung cancer further comprises instructions that, when executed by the processor, cause the processor to determine that the subject does not have a nodule based on the nodule-specific features.

In various embodiments, the lung cancer is either non-small cell lung cancer or small cell lung cancer. In various embodiments, the lung cancer is either adenocarcinoma or squamous cell carcinoma. In various embodiments, the non-transitory computer readable medium further comprises instructions that, when executed by a processor, cause the processor to: select a clinical response for the subject based on the predicted risk of lung cancer. In various embodiments, the instructions that cause the processor to select a clinical response for the subject further comprises instructions that, when executed by the processor, cause the processor to select an intervention for treating the subject. In various embodiments, the instructions that cause the processor to select an intervention further comprises instructions that, when executed by the processor, cause the processor to select a therapeutic for administration to the subject. In various embodiments, the selected therapeutic is prophylactically administered to the subject to delay or prevent the development of the lung cancer.

In various embodiments, the clinical response comprises providing counseling to the subject to modify behavior of the subject. In various embodiments, the clinical response comprises increasing a frequency of follow up for the subject. In various embodiments, the clinical response comprises performing or scheduling to be performed an additional risk prediction test to confirm the predicted risk of lung cancer. In various embodiments, one or more of the trained risk prediction models are one of a random forest model or gradient boosted model.

Additionally disclosed herein is a method for predicting one or more risks of lung cancer for a subject, the method comprising: obtaining one or more images captured from the subject; extracting features from the one or more obtained images, the extracted features comprising at least nodule specific features; and predicting one or more risks of lung cancer for the subject by applying one or more trained risk prediction models to analyze the extracted features from the one or more obtained images. In various embodiments, the nodule specific features comprise longitudinal nodule specific features. In various embodiments, the nodule specific features comprise one or more of nodule specific attenuation, nodule margin description, nodule size, nodule shape, nodule texture, nodule diameter, Lung-RADS score, or radiomic features. In various embodiments, the longitudinal nodule specific features comprise one or more of a change in nodule specific attenuation, a change in nodule margin description, a change in nodule size, a change in nodule shape, a change in nodule texture, a change in nodule diameter, a change in Lung-RADS score, or a change in radiomic features. In various embodiments, radiomic features comprise one or more of first order statistics, 3D shape based features, 2D shape based features, gray level co-occurrence matrix, gray level run length matrix, gray level size zone matrix, neighboring gray tone difference matrix, and gray level dependence matrix. In various embodiments, the nodule specific features are extracted from a radiologist report. In various embodiments, the nodule specific features are computationally extracted by implementing an image analysis algorithm. In various embodiments, the one or more images captured from the subject comprise one or more nodules suspected of being cancerous. In various embodiments, predicting one or more risks of lung cancer for the subject comprises: for each of the one or more nodules, classifying the nodule as cancerous or non-cancerous by applying the one or more trained risk predictions models to analyze features extracted from the nodule; and determining presence or absence of existing cancer in the subject based on the one or more nodules classified as cancerous or non-cancerous. In various embodiments, determining presence or absence of existing cancer in the subject based on the one or more nodules classified as cancerous or non-cancerous comprises: responsive to at least one nodule being classified as cancerous, determining that the subject has a presence of existing cancer. In various embodiments, determining presence or absence of existing cancer in the subject based on the one or more nodules classified as cancerous or non-cancerous comprises: responsive to at least two, at least three, at least four, or at least five nodules being classified as cancerous, determining that the subject has a presence of existing cancer. In various embodiments, determining presence or absence of existing cancer in the subject based on the one or more nodules classified as cancerous or non-cancerous comprises: responsive to zero nodules being classified as cancerous, determining that the subject has an absence of existing cancer.

Additionally disclosed herein is a non-transitory computer readable medium for predicting one or more risks of lung cancer for a subject, the non-transitory computer readable medium comprising instructions that, when executed by a processor, cause the processor to: obtain one or more images captured from the subject; extract features from the one or more obtained images, the extracted features comprising at least nodule specific features; and predict one or more risks of lung cancer for the subject by applying one or more trained risk prediction models to analyze the extracted features from the one or more obtained images. In various embodiments, the nodule specific features comprise longitudinal nodule specific features. In various embodiments, the nodule specific features comprise one or more of nodule specific attenuation, nodule margin description, nodule size, nodule shape, nodule texture, nodule diameter, Lung-RADS score, or radiomic features. In various embodiments, the longitudinal nodule specific features comprise one or more of a change in nodule specific attenuation, a change in nodule margin description, a change in nodule size, a change in nodule shape, a change in nodule texture, a change in nodule diameter, a change in Lung-RADS score, or a change in radiomic features. In various embodiments, radiomic features comprise one or more of first order statistics, 3D shape based features, 2D shape based features, gray level co-occurrence matrix, gray level run length matrix, gray level size zone matrix, neighboring gray tone difference matrix, and gray level dependence matrix. In various embodiments, the nodule specific features are extracted from a radiologist report. In various embodiments, the nodule specific features are computationally extracted by implementing an image analysis algorithm. In various embodiments, the one or more images captured from the subject comprise one or more nodules suspected of being cancerous. In various embodiments, the instructions that cause the processor to predicting one or more risks of lung cancer for the subject further comprises instructions that, when executed by the processor, cause the processor to: for each of the one or more nodules, classify the nodule as cancerous or non-cancerous by applying the one or more trained risk predictions models to analyze features extracted from the nodule; and determine presence or absence of existing cancer in the subject based on the one or more nodules classified as cancerous or non-cancerous. In various embodiments, the instructions that cause the processor to determine presence or absence of existing cancer in the subject based on the one or more nodules classified as cancerous or non-cancerous further comprises instructions that, when executed by the processor, cause the processor to: responsive to at least one nodule being classified as cancerous, determine that the subject has a presence of existing cancer. In various embodiments, the instructions that cause the processor to determine presence or absence of existing cancer in the subject based on the one or more nodules classified as cancerous or non-cancerous further comprises instructions that, when executed by the processor, cause the processor to: responsive to at least two, at least three, at least four, or at least five nodules being classified as cancerous, determine that the subject has a presence of existing cancer. In various embodiments, the instructions that cause the processor to determine presence or absence of existing cancer in the subject based on the one or more nodules classified as cancerous or non-cancerous further comprises instructions that, when executed by the processor, cause the processor to: responsive to zero nodules being classified as cancerous, determine that the subject has an absence of existing cancer.

BRIEF DESCRIPTION OF THE DRAWINGS

These and other features, aspects, and advantages of the present invention will become better understood with regard to the following description and accompanying drawings. It is noted that wherever practicable similar or like reference numbers may be used in the figures and may indicate similar or like functionality. For example, a letter after a reference numeral, such as "features 215A," indicates that the text refers specifically to the element having that particular reference numeral. A reference numeral in the text without a following letter, such as "features 215," refers to any or all of the elements in the figures bearing that reference numeral (e.g. "features 215" in the text refers to reference numerals "features 215A" and/or "features 215B" in the figures).

FIG. 1A depicts a system environment overview for determining a cancer prediction for a subject, in accordance with an embodiment.

FIG. 7A depicts characteristics of the risk prediction model across patient cohorts of various different time points (e.g., t0, t1, t2, or combinations thereof), in accordance with the embodiment shown in FIG. 3A.

FIG. 7B shows the patient demographics used for training and testing a risk prediction model, in accordance with the embodiment shown in FIG. 3A.

FIG. 7E depicts the top 10 nodule features of the nodule model component of the risk prediction model, in accordance with the embodiment shown in FIG. 3A.

FIG. 7F depicts the top 10 non-nodule features of the non-nodule model component of the risk prediction model, in accordance with the embodiment shown in FIG. 3A.

FIG. 9A depicts characteristics of the risk prediction model across patient cohorts of various different time points (e.g., t0, t1, t2, or combinations thereof), in accordance with the embodiment shown in FIG. 3B.

FIG. 9B shows the patient demographics used for training and testing a risk prediction model, in accordance with the embodiment shown in FIG. 3B.

FIG. 9E depicts the top 10 features (e.g., nodule and non-nodule features) of the risk prediction model, in accordance with the embodiment shown in FIG. 3B.

FIG. 10A shows the patient demographics used for training and testing a risk prediction model using Lung-RADS 1-3 patients at a t1 timepoint, in accordance with the embodiment shown in FIG. 3A.

FIG. 10D depicts the top 10 nodule features of the nodule model component of the risk prediction model trained using Lung-RADS 1-3 patients at a t1 timepoint.

FIG. 10E depicts the top 10 non-nodule features of the non-nodule model component of the risk prediction model trained using Lung-RADS 1-3 patients at a t1 timepoint.

FIG. 11A shows the patient demographics used for training and testing a risk prediction model using Lung-RADS 1-3 patients at a t2 timepoint, in accordance with the embodiment shown in FIG. 3A.

FIG. 11D depicts the top 10 nodule features of the nodule model component of the risk prediction model trained using Lung-RADS 1-3 patients at a t2 timepoint.

FIG. 11E depicts the top 10 non-nodule features of the non-nodule model component of the risk prediction model trained using Lung-RADS 1-3 patients at a t2 timepoint.

FIG. 12A shows the patient demographics used for training and testing a single-timepoint risk prediction model using Lung-RADS 1-3 patients at a t0 timepoint, in accordance with the embodiment shown in FIG. 3A.

FIG. 12D depicts the top 10 nodule features of the nodule model component of the single timepoint risk prediction model trained using Lung-RADS 1-3 patients at a t0 timepoint.

FIG. 12E depicts the top 10 non-nodule features of the non-nodule model component of the single timepoint risk prediction model trained using Lung-RADS 1-3 patients at a t0 timepoint.

FIG. 13B shows the patient demographics used for training and testing a risk prediction model using Lung-RADS 2-4B patients for predicting prevalent or existing cancer.

FIG. 13C shows the resulting predictions of a risk prediction model using Lung-RADS 2-4B patients for predicting prevalent or existing cancer.

DETAILED DESCRIPTION

I. Definitions

Figure 1B:
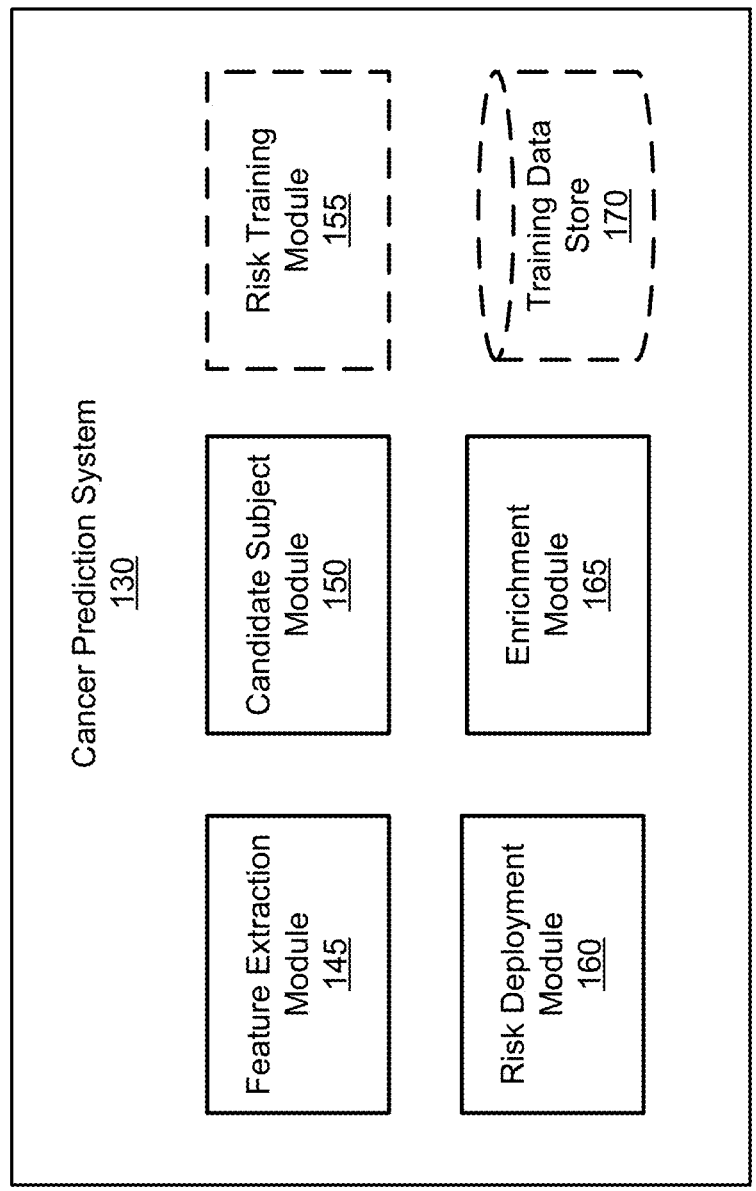
FIG. 1B depicts a block diagram of the cancer prediction system, in accordance with an embodiment.

Terms used in the claims and specification are defined as set forth below unless otherwise specified.

The terms "subject" or "patient" are used interchangeably and encompass a cell, tissue, or organism, human or non-human, whether in vivo, ex vivo, or in vitro, male or female.

The term "mammal" encompasses both humans and non-humans and includes but is not limited to humans, non-human primates, canines, felines, murines, bovines, equines, and porcines.

The term "sample" or "test sample" can include a single cell or multiple cells or fragments of cells or an aliquot of body fluid, such as a blood sample, taken from a subject, by means including venipuncture, excretion, ejaculation, massage, biopsy, needle aspirate, lavage sample, scraping, surgical incision, or intervention or other means known in the art. Examples of an aliquot of body fluid include amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In various embodiments, a sample can be a biopsy of a tissue, such as a lung tumor or a lung nodule.

The term "obtaining one or more images" encompasses obtaining one or more images captured from a subject or obtaining one or more images captured from a sample obtained from a subject. Obtaining one or more images can encompass performing steps of capturing the one or more images from the subject or from a sample obtained from the subject. The phrase can also encompass receiving one or more images, e.g., from a third party that has performed the steps of capturing the one or more images from the subject or from a sample obtained from the subject. The one or more images can be obtained by one of skill in the art via a variety of known ways including stored on a storage memory. In various embodiments, "obtaining one or more images"

refers to obtaining one or more images that are each captured from a subject at a single timepoint (e.g., a single patient visit). In various embodiments, "obtaining one or more images" refers to obtaining one or more images that are captured from a subject at different timepoints (e.g., across different patient visits).

The term "training image" refers to an image (e.g., CT image or X-ray image) captured from an individual that is used to train a risk prediction model, e.g., a lung cancer risk prediction model such as a model described herein. In various embodiments, a training image is a computed tomography (CT) image from a cohort that is built from routine clinical care of patients (e.g., from patients that were routinely screened). In various embodiments, a training image is a computed tomography (CT) image from a cohort built from research investigations (e.g., federally/industry sponsored research investigations). In various embodiments, a training image is a computed tomography (CT) image from the National Lung Cancer Screening Trial (NLST) cohort. In various embodiments, a training image is a computed tomography (CT) image included in a custom dataset. For example, the training image can be captured from a training individual. The term "training individual" refers to an individual from whom a training image is captured or otherwise obtained for use in training a risk prediction model.

The term "nodule specific features" or "nodule-specific features" refers to features of a lung nodule, the edge of the lung nodule, and the boundary/peri-nodule area, examples of which include nodule specific attenuation, nodule margin description (e.g., up to 5 mm, up to 10 mm, up to 15 mm, or up to 20 mm in the tissue parenchyma surrounding the lung nodule), nodule size, nodule shape, nodule texture (e.g., smooth, spiculated, etc.), nodule diameter, and Lung-RADS score. In various embodiments, nodule-specific features are computationally extracted from images (e.g., by implementing an image analysis algorithm). For example, nodule specific features can be radiomic features that are extracted using an image processing algorithm, such as PyRadiomics. Example radiomic features can include first order statistics, 3D shape based features, 2D shape based features, gray level co-occurrence matrix, gray level run length matrix, gray level size zone matrix, neighboring gray tone difference matrix, and gray level dependence matrix. In various embodiments, radiomic features are extracted from an image that has been transformed by applying a filter, such as a wavelet filter or a gaussian filter. Thus, any of first order statistics, 3D shape based features, 2D shape based features, gray level co-occurrence matrix, gray level run length matrix, gray level size zone matrix, neighboring gray tone difference matrix, and gray level dependence matrix can be extracted from a wavelet transformed image or a gaussian transformed image. The term "nodule specific features" further refers to longitudinal features of any of the aforementioned features of a lung nodule. For example, longitudinal features of a lung nodule can be a change in a feature of a lung nodule between two or more timepoints. For example, given a first timepoint t0 and a second timepoint t1, a longitudinal feature of a lung nodule can be a change in a feature of lung nodule between timepoint t0 and timepoint t1. In particular embodiments, longitudinal features of a lung nodule include a change in nodule specific attenuation, change in nodule margin description, change in nodule size, change in nodule shape, change in nodule texture (e.g., smooth, spiculated, etc.), change in nodule diameter, change in Lung-RADS score, and change in radiomic features. Such longitudinal nodule specific features can provide insight as to the changes (e.g., non-linear changes) of the nodule over time. In various embodiments, the time between a first timepoint (e.g., t0) and a second timepoint (e.g., t1) can be at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 24 months, at least 30 months, at least 36 months, at least 42 months, at least 48 months, at least 54 months, at least 60 months, at least 66 months, at least 72 months, at least 78 months, at least 84 months, at least 90 months, at least 96 months, at least 102 months, at least 108 months, at least 114 months, or at least 120 months. In various embodiments, the time between a first timepoint (e.g., t0) and a second timepoint (e.g., t1) can be between 1 month and 12 months, between 2 months and 10 months, between 3 months and 8 months, or between 4 months and 6 months. In various embodiments, the time between a first timepoint (e.g., t0) and a second timepoint (e.g., t1) can be between 12 months and 120 months, between 20 months and 100 months, between 30 months and 80 months, or between 40 months and 60 months.

In various embodiments, there may be additional timepoints (e.g., t3, t4, and so on) beyond a first timepoint and a second timepoint, during which the nodule specific features are determined from a subject. Thus, longitudinal features of a lung nodule can be determined from any two timepoints (e.g., first timepoint and third timepoint, second timepoint and third timepoint, and so on). In various embodiments, the time between any two timepoints is different. For example, the time between a first timepoint and a second timepoint may differ from the time between a second timepoint and an additional timepoint. Such a scenario may occur, for example, if the subject shows up on an irregular basis for imaging, monitoring, and/or detection of cancer (e.g., on a monthly basis for a first period of time, followed by a yearly basis for a second period of time), and/or if the nodule specific features are determined at an irregularly-spaced subset of timepoints within an available set of timepoints. In various embodiments, the time between any two timepoints may be the same. For example, the time between a first timepoint and a second timepoint may be the same as the time between a second timepoint and an additional timepoint. In various embodiments, the time between any two timepoints may be 1 week, 2 weeks, 3 weeks, 4 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, or 10 years. Such a scenario may occur, for example, if the subject shows up on a consistent or regular basis (e.g., on a weekly basis, on a monthly basis, on a yearly basis, etc. for imaging, monitoring, and/or detection of cancer), and/or if the nodule specific features are determined at a regularly-spaced subset of timepoints within an available set of timepoints.

In various embodiments, nodule-specific features are extracted from a report prepared by a trained professional (e.g., a radiologist) who analyzes images of a subject, such as CT scans of the subject. Such nodule-specific features are referred to as "subjective nodule specific features."

The term "non-nodule specific features" refers to any of lung parenchyma features or body composition features. Non-nodule specific features can include features from a subject that are not nodules. Non-nodule specific features can include features from a subject that are not associated with nodules. Lung parenchyma features can include densitometric measures of the lung parenchyma which may include, for example, the percentage of the lung occupied by (i) low attenuation area (LAA), which is defined as the area/volume having an attenuation less than −950 Hounsfield Units (HU) and (ii) high attenuation area (HAA), which is defined as the area/volume of lung having attenuation between −600 HU and −250 HU, and the ratio between LAA in the upper lung zone to that in the lower lung zone (Ratio LAA). Lung parenchyma features can further include measures of interstitial changes in the lung parenchyma such as local histogram measures of the lung parenchyma, the percentage of lung occupied by, for example, normal tissue, centrilobular emphysema, centrilobular nodule, ground glass, honeycombing, linear scar, nodular, reticular, subpleural line, other emphysema and/or cyst. Body composition features include, for example, pectoralis major cross-sectional area, pectoralis minor cross-sectional area, pectoralis major lean cross-sectional area, pectoralis minor lean cross-sectional area, aggregate cross-sectional area of the left or right pectoralis major or minor muscles, and subcutaneous fat cross-sectional area.

The term "non-nodule specific features" further refers to longitudinal features of any of the aforementioned lung parenchyma features or aforementioned body composition features. For example, longitudinal features of the lung parenchyma can be a change in features of the lung parenchyma between two or more timepoints. Additionally, longitudinal features of the body composition can be a change in features of the body composition between two or more timepoints. For example, given a first timepoint t0 and a second timepoint t1, a longitudinal feature of the lung parenchyma or body composition can be a change in a feature of the lung parenchyma or body composition between timepoint t0 and timepoint t1. In particular embodiments, longitudinal features of the lung parenchyma include a change in the percentage of the lung occupied by (i) low attenuation area (LAA), which is defined as the area/volume having an attenuation less than −950 Hounsfield Units (HU) or a change in percentage of the lung occupied by (ii) high attenuation area (HAA), which is defined as the area/volume of lung having attenuation between −600 HU and −250 HU, or a change in the ratio between LAA in the upper lung zone to that in the lower lung zone (Ratio LAA). Longitudinal features of the lung parenchyma can further include changes in measures of interstitial changes in the lung parenchyma such as a change in local histogram measures of the lung parenchyma or a change in the percentage of lung occupied by, for example, normal tissue, centrilobular emphysema, centrilobular nodule, ground glass, honeycombing, linear scar, nodular, reticular, subpleural line, other emphysema and/or cyst. In particular embodiments, longitudinal features of the body composition include a change in pectoralis major cross-sectional area, change in pectoralis minor cross-sectional area, change in pectoralis major lean cross-sectional area, change in pectoralis minor lean cross-sectional area, change in aggregate cross-sectional area of the left or right pectoralis major or minor muscles, and change in subcutaneous fat cross-sectional area. Such longitudinal non-nodule specific features can provide insight as to the changes (e.g., non-linear changes) of the lung parenchyma and/or body composition over time, which can be informative for predicting cancer disease activity. In various embodiments, the time between a first timepoint (e.g., t0) and a second timepoint (e.g., t1) can be at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 24 months, at least 30 months, at least 36 months, at least 42 months, at least 48 months, at least 54 months, at least 60 months, at least 66 months, at least 72 months, at least 78 months, at least 84 months, at least 90 months, at least 96 months, at least 102 months, at least 108 months, at least 114 months, or at least 120 months. In various embodiments, the time between a first timepoint (e.g., t0) and a second timepoint (e.g., t1) can be between 1 month and 12 months, between 2 months and 10 months, between 3 months and 8 months, or between 4 months and 6 months. In various embodiments, the time between a first timepoint (e.g., t0) and a second timepoint (e.g., t1) can be between 12 months and 120 months, between 20 months and 100 months, between 30 months and 80 months, or between 40 months and 60 months.

In various embodiments, there may be additional timepoints (e.g., t3, t4, and so on) beyond a first timepoint and a second timepoint, during which the non-nodule specific features are determined from a subject. Thus, longitudinal features of the lung parenchyma and/or body composition can be determined from any two timepoints (e.g., first timepoint and third timepoint, second timepoint and third timepoint, and so on). In various embodiments, the time between any two timepoints is different. For example, the time between a first timepoint and a second timepoint may differ from the time between a second timepoint and an additional timepoint. Such a scenario may occur, for example, if the subject shows up on an irregular basis for imaging, monitoring, and/or detection of cancer (e.g., on a monthly basis for a first period of time, followed by a yearly basis for a second period of time), and/or if the non-nodule specific features are determined at an irregularly-spaced subset of timepoints within an available set of timepoints. In various embodiments, the time between any two timepoints may be the same. For example, the time between a first timepoint and a second timepoint may be the same as the time between a second timepoint and an additional timepoint. In various embodiments, the time between any two timepoints may be 1 week, 2 weeks, 3 weeks, 4 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, or 10 years. Such a scenario may occur, for example, if the subject shows up on a consistent or regular basis (e.g., on a weekly basis, on a monthly basis, on a yearly basis, etc. for imaging, monitoring, and/or detection of cancer), and/or if the non-nodule specific features are determined at a regularly-spaced subset of timepoints within an available set of timepoints.

In various embodiments, "non-nodule specific features" are computationally extracted from images, such as images captured from a subject. In various embodiments, non-nodule features that are computationally extracted from features can be used to construct a report, such as a radiologist report that includes the non-nodule features. In various embodiments, "non-nodule specific features" do not include a duration of emphysema or a duration of cardiovascular disease.

The phrase "Lung-RADS X-Y" is meant to include individuals classified as Lung-RADS X, Lung-RADS Y, and any value in between numerical variables "X" and "Y." For example, Lung-RADS 1-3 is indicative of individuals classified as Lung-RADS 1, Lung-RADS 2, and Lung-RADS 3.

The phrase "Lung-RADS X-Y prediction model" refers to a risk prediction model that is trained using training images captured from training individuals that are classified in any one of Lung-RADS X-Y.

The phrase "M year prediction model" refers to a risk prediction model that is trained to predict a risk of cancer within a "M" time period. In various embodiments, "M" is any of 0 months, 1 month, 2 months, 3 months, 4 months, 5 months, 6 months, 7 months, 8 months, 9 months, 10 months, 11 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. In various embodiments, the M year prediction model is trained to predict risk of existing or prevalent cancer (e.g., M is any of 0 months, 1 month, 2 months, 3 months, 4 months, 5 months, or 6 months). In various embodiments, the M year prediction model is trained to predict future risk of developing cancer (e.g., M is greater than 6 months). In various embodiments, "M" is measured from the time of acquisition of one or more images from a subject. Therefore, a 1 year prediction model refers to a risk prediction model that is trained to predict a future risk of cancer within 1 year from the time of acquisition of one or more images from a subject.

The phrases "existing cancer" and "prevalent cancer" are used interchangeably and generally refer to detection of a presence or absence of cancer in a subject. In various embodiments, the phrases "existing cancer" and "prevalent cancer" refers to the determination that a subject has presence of cancer within less than 6 months (e.g., 6 months, 5 months, 4 months, 3 months, 2 months, 1 month or 0 months) from time of acquisition of one or more images from a subject. In various embodiments, the phrases "existing cancer" and "prevalent cancer" refers to the determination that a subject has presence of cancer within less than 6 months (e.g., 6 months, 5 months, 4 months, 3 months, 2 months, 1 month or 0 months) from detection of a cancerous nodule. As disclosed herein, risk prediction models can be implemented to predict whether a subject likely has existing or prevalent cancer based on radiomic features, such as nodule specific radiomic features, that are informative for discriminating cancerous and non-cancerous nodules.

The phrase "M year, Lung-RADS X-Y prediction model" refers to a risk prediction model that 1) is trained using training images captured from training individuals that are classified in any one of Lung-RADS X-Y and 2) is trained to predict a future risk of cancer within "M" years.

The phrase "future risk of cancer" refers to a risk that subject will develop cancer within a given period of time, e.g., 1 year or 3 years from a baseline time point. In various embodiments, the future risk of cancer refers to a likelihood that a subject will develop cancer within a given period of time from a baseline time point. In various embodiments, the future risk of cancer refers to a likelihood that a subject will develop cancer within 1 year. In various embodiments, the future risk of cancer refers to a likelihood that a subject will develop cancer within 3 years. In various embodiments, the future risk of cancer refers to a likelihood that a subject will develop cancer within 5 years. In various embodiments, the future risk of cancer refers to a likelihood that a subject will develop cancer or be diagnosed with cancer within at least 6 months, within at least 1 year, at least 2 years, at least 3 years, at least 4 years, at least 5 years, at least 6 years, at least 7 years, at least 8 years, at least 9 years, at least 10 years, at least 11 years, at least 12 years, at least 13 years, at least 14 years, at least 15 years, at least 16 years, at least 17 years, at least 18 years, at least 19 years, or at least 20 years. In various embodiments, the "future risk of cancer" is a binary value (e.g., 0 or 1, where 0 indicates unlikely to develop cancer in the period of time and 1 indicates likely to develop cancer in the period of time). In various embodiments, the "future risk of cancer" is a continuous value (e.g., between 0 and 1, where a value closer to 1 indicates higher likelihood of developing cancer in the period of time).

The terms "treating," "treatment," or "therapy" of lung cancer shall mean slowing, stopping or reversing a cancer's progression by administration of treatment. In some embodiments, treating lung cancer means reversing the cancer's progression, ideally to the point of eliminating the cancer itself. In various embodiments, "treating," "treatment," or "therapy" of lung cancer includes administering a therapeutic agent or pharmaceutical composition to the subject. Additionally, as used herein, "treating," "treatment," or "therapy" of lung cancer further includes administering a therapeutic agent or pharmaceutical composition for prophylactic purposes. Prophylaxis of a cancer refers to the administration of a composition or therapeutic agent to prevent the occurrence, development, onset, progression, or recurrence of cancer or some or all of the symptoms of lung cancer or to lessen the likelihood of the onset of lung cancer.

It must be noted that, as used in the specification, the singular forms "a," "an" and "the" include plural referents unless the context clearly dictates otherwise.

II. System Environment Overview

FIG. 1A depicts a system environment overview for determining a cancer prediction for a subject, in accordance with an embodiment. The system environment 100 provides context in order to introduce a subject 110, an imaging device 120, and a cancer prediction system 130 for determining a cancer prediction 140 for the subject 110. Although FIG. 1A depicts one subject 110 for whom a cancer prediction 140 is generated, in various embodiments, the system environment 100 includes two or more subjects such that that cancer prediction system 130 generates cancer predictions 140 for the two or more subjects (e.g., a cancer prediction for each subject).

In various embodiments, the subject 110 is healthy. For example, the subject is not previously diagnosed with cancer or is not suspected of having cancer. Thus, the methods for risk prediction of cancer described herein can be beneficial for early detection of cancer in the healthy subject. In particular embodiments, the type of cancer in the subject is a lung cancer. Thus, the methods described herein can be beneficial for early detection of lung cancer. In various embodiments, the subject was previously diagnosed with a cancer. In such embodiments, the subject can be in remission and therefore, the methods for risk prediction of cancer can be beneficial for determining whether the subject is likely to experience a recurrence of cancer within a time period.

In various embodiments, subjects predicted to develop cancer or experience a cancer recurrence within a time period can be administered treatments, such as prophylactic treatments that slow or prevent the onset or recurrence of the cancer. In various embodiments, subjects predicted to develop cancer or experience a cancer recurrence within a time period are selected to be enrolled in a clinical trial.

Referring to FIG. 1A, the imaging device 120 captures an image from the subject 110. In various embodiments, the imaging device 120 captures an image from a test sample obtained from the subject 110. In various embodiments, the image and/or the sample can be obtained by a third party, e.g., a medical professional. Examples of medical professionals include physicians, emergency medical technicians, nurses, first responders, psychologists, phlebotomist, medical physics personnel, nurse practitioners, surgeons, dentists, and any other obvious medical professional as would be known to one skilled in the art. In various embodiments, the image and/or the sample can be obtained in a hospital setting or a medical clinic. In various embodiments, the image and/or the sample can be captured using an imaging device, such as a mobile imaging device.

In some embodiments, the imaging device 120 captures an image of an anatomical location of the subject 110. Example anatomical locations of a subject can include lungs, thoracic cavity, kidney, liver, pancreas, brain, stomach, intestines, hip, knees, legs, arms, and face. In various embodiments, the imaging device 120 captures an image of the thoracic cavity of the subject 110. In various embodiments, the imaging device 120 captures an image of the subject's lungs. In various embodiments, the imaging device 120 captures an image of the subject's chest (e.g., chest wall including the pectoralis muscle). In various embodiments, the imaging device 120 captures an image of the thoracic cavity including the subject's lungs. In various embodiments, the imaging device 120 captures an image of the thoracic cavity including the subject's chest (e.g., chest wall including the pectoralis muscle). In various embodiments, the imaging device 120 captures an image of the thoracic cavity including both the subject's lungs and the subject's chest (e.g., chest wall including the pectoralis muscle).

In various embodiments, the imaging device 120 is one of a computed tomography (CT) scanner, magnetic resonance imaging (MRI) scanner, positron emission tomography (PET) scanner, x-ray scanner, or an ultrasound imaging device. In particular embodiments, the imaging device 120 is a CT scanner that captures one or more images of the subject 110. In various embodiments, the imaging device 120 is a CT scanner that captures one or more CT images of at least the lung of the subject. In various embodiments, the imaging device 120 is a CT scanner that captures one or more CT images of at least the chest of the subject. In particular embodiments, the imaging device 120 is a CT scanner that captures one or more CT images of the thoracic cavity including both the subject's lungs and the subject's chest (e.g., chest wall including the pectoralis muscle). In various embodiments, the imaging device 120 is a CT scanner that captures one or more whole body CT images of the subject. In particular embodiments, the imaging device 120 is an X-ray scanner that captures one or more X-ray images of the chest including both the subject's lungs and the subject's chest (e.g., chest wall including the pectoralis muscle).

In various embodiments, the imaging device 120 is employed to capture images from a subject at two or more timepoints. In particular embodiments, the imaging device 120 is employed to capture images from a subject at two timepoints. In various embodiments, the imaging device 120 is employed to capture images from a subject at three or more, four or more, five or more, six or more, seven or more, eight or more, nine or more, or ten or more timepoints. For example, the imaging device 120 may be employed to capture a first image at time=t0 from the subject. At a subsequent time=t1, the imaging device 120 may be employed again to capture a second image from the same subject. Thus, the first image and second image captured at two different time points can be analyzed to generate longitudinal features. Longitudinal features are described in further detail herein.

Generally, the cancer prediction system 130 analyzes one or more images captured from the subject 110 (e.g., images captured by the imaging device 120) and generates the cancer prediction 140 for the subject 110. In various embodiments, the cancer prediction 140 determined by the cancer prediction system 130 is a predicted risk of cancer for the subject 110. For example, the cancer prediction 140 is a value indicating whether the subject 110 is predicted to develop cancer within a time period (e.g., including but not limited to within 1 year, within 3 years, or within 5 years) from a date that the images were captured from the subject 110.

In various embodiments, to generate the cancer prediction 140, the cancer prediction system 130 extracts features from the one or more images and applies one or more trained risk prediction models to analyze the features of the one or more images. A trained risk prediction model predicts a risk of cancer for the subject 110 within a time period. For example, the cancer prediction system 130 can apply a risk prediction model that is trained to predict a future risk of cancer within 3 years. In various embodiments, the cancer prediction system 130 determines multiple risks of cancer across different time periods for the subject 110 by applying multiple trained risk prediction models. For example, in addition to applying a risk prediction model that is trained to predict a future risk of cancer within 3 years, the cancer prediction system 130 further applies a second risk prediction model that is trained to predict a future risk of cancer within 5 years. The cancer prediction system 130 can apply more trained risk prediction models that are trained for additional time periods (e.g., 1 year, 10 years, 15 years, 20 years, etc). Generally, risk prediction models are trained independently and not additive (e.g., cannot subtract cancers predicted in 1 year from cancers predicted in 3 years to obtain cancers predicted to develop 1 year but before 3 years).

In various embodiments, the cancer prediction 140 is an indication derived from the predicted risk of cancer for the subject, the indication identifying whether the subject 110 is to be included or excluded from a patient cohort for enrollment in a clinical trial. The indication is useful for clinical trial enrichment purposes. For example, if the subject 110 is predicted to develop cancer within a time period (e.g., within 1 year, within 2 years, within 3 years, within 4 years, within 5 years, within 6 years, within 7 years, within 8 years, within 9 years, within 10 years, within 11 years, within 12 years, within 13 years, within 14 years, within 15 years, within 16 years, within 17 years, within 18 years, within 19 years, and/or within 20 years), the indication identifies that the subject 110 is to be included in a patient cohort for enrollment in a clinical trial. As another example, if the subject 110 is not predicted to develop cancer within a time period, the indication identifies that the subject 110 is to be excluded from the patient cohort for enrollment in a clinical trial.

In various embodiments, the cancer prediction 140 can include a recommended intervention for the subject 110 based on the predicted risk of cancer. For example, if the cancer prediction system 130 determines that the subject 110 is likely to develop cancer within 1 year, the cancer prediction 140 can include a recommended intervention to delay or prevent the rapid onset of the cancer over the next year.

The cancer prediction system 130 can include one or more computers, embodied as a computer system 500 as discussed below with respect to FIG. 5. Therefore, in various embodiments, the steps described in reference to the cancer prediction system 130 are performed in silico.

In various embodiments, the imaging device 120 and the cancer prediction system 130 are employed by different parties. For example, a first party operates the imaging device 120 to capture one or more images from the subject 110 and then provides the captured one or more images to a second party which implements the cancer prediction system 130 to determine a cancer prediction 140. In some embodiments, the imaging device 120 and the cancer prediction system 130 are employed by the same party.

Reference is now made to FIG. 1B which depicts a block diagram illustrating the computer logic components of the cancer prediction system 130, in accordance with an embodiment. Here, the cancer prediction system 130 includes a feature extraction module 145, a candidate subject module 150, a risk training module 155, a risk deployment module 160, an enrichment module 165, and a training data store 170. In various embodiments, the cancer prediction system 130 can be configured differently with additional or fewer modules. For example, a cancer prediction system 130 need not include the candidate subject module 150. As another example, the cancer prediction system 130 need not include the risk training module 155 or the training data store 170 (as indicated by their dotted lines in FIG. 1B), and instead, the risk training module 155 and training data store 170 are employed by a different system and/or party.

Generally, the feature extraction module 145 extracts features from images captured from subjects or training images captured from training individuals. In various embodiments, the feature extraction module 145 extracts non-nodule specific features from images or training images. In various embodiments, the feature extraction module 145 extracts longitudinal non-nodule specific features and/or longitudinal nodule specific features from images or training images. Here, the feature extraction module 145 extracts features from two or more images obtained from a subject at different timepoints and determines longitudinal non-nodule specific features and/or longitudinal nodule specific features from the extracted features from the two or more images. As an example, to generate longitudinal nodule specific features, the feature extraction module 145 extracts nodule specific features from a first image obtained at a first timepoint and further extracts nodule specific features from a second image obtained at a second timepoint. The feature extraction module 145 combines the nodule specific features extracted from the first image with the nodule specific features extracted from the second image. In various embodiments, the feature extraction module 145 determines the difference in the nodule specific features extracted from the first image with the nodule specific features extracted from the second image. Thus, the longitudinal nodule specific features represents the change in the nodule specific features between the first and second timepoints. As another example, to generate longitudinal non-nodule specific features, the feature extraction module 145 extracts non-nodule specific features from a first image obtained at a first timepoint and further extracts non-nodule specific features from a second image obtained at a second timepoint. The feature extraction module 145 combines the non-nodule specific features extracted from the first image with the non-nodule specific features extracted from the second image. In various embodiments, the feature extraction module 145 determines the difference in the non-nodule specific features extracted from the first image with the non-nodule specific features extracted from the second image. Thus, the longitudinal non-nodule specific features represents the change in the non-nodule specific features between the first and second timepoints.

In various embodiments, to combine the features extracted from a first image with features extracted from a second image, the feature extraction module 145 performs an image recognition to identify characteristics of the first image and second image. For example, the feature extraction module 145 may perform an image recognition on the first image to identify a nodule present in the first image, and further performs an image recognition on the second image to identify the same nodule in the second image. Thus, the feature extraction module 145 can combine the nodule-specific features extracted from the nodule in the first image with nodule-specific features extracted from the nodule in the second image.

In various embodiments, the feature extraction module 145 extracts nodule specific features from images or training images. In various embodiments, the feature extraction module 145 extracts nodule specific features and non-nodule specific features from images or training images. The feature extraction module 145 provides features extracted from training images to the risk training module 155 for training risk prediction models. In various embodiments, the feature extraction module 145 provides features extracted from images captured from subjects to the risk to the candidate subject module 150 for identifying candidate subjects. In various embodiments, the feature extraction module 145 provides features extracted from images captured from subjects to the risk deployment module 160 for deploying one or more trained risk prediction models.

The candidate subject module 150 analyzes features extracted from one or more images captured from a subject and determines whether the subject is a candidate subject for undergoing risk prediction. This is useful for identifying a subset of patients who are to undergo risk prediction. For example, it may be preferable to predict risk of cancer for low risk cancer patients (e.g., patients who currently do not have cancer and/or do not currently have a lung nodule indicative of cancer). Therefore, the candidate subject module 150 can identify a subset of low risk cancer patients for subsequent risk prediction. In various embodiments, the candidate subject module 150 analyzes both nodule specific features and non-nodule specific features to determine whether a subject is a candidate subject. In various embodiments, the candidate subject module 150 only analyzes nodule specific features to determine whether a subject is a candidate subject. In various embodiments, the candidate subject module 150 need not be implemented by the cancer staging system 140. For example, in a scenario where all subjects are to be analyzed for risk of cancer, then all subjects are candidate subjects who are to undergo risk prediction.

The risk training module 155 trains risk prediction models using training data derived from training individuals. For example, the training data includes extracted features from one or more training images captured from the training individuals. In various embodiments, the risk training module 155 trains a risk prediction model comprising both nodule specific features and non-nodule specific features. In such embodiments, the risk deployment module 160 implements a risk prediction model to analyze both nodule specific features and non-nodule specific features extracted from images obtained from a subject (e.g., subject 110 in FIG. 1A) to determine a risk of cancer. In various embodiments, the risk training module 155 trains a risk prediction model comprising only non-nodule specific features. In such embodiments, the risk deployment module 160 implements a risk prediction model to analyze only non-nodule specific features extracted from images obtained from a subject (e.g., subject 110 in FIG. 1A) to determine a risk of cancer.

The risk deployment module 160 implements risk prediction models to analyze features extracted from images obtained from a subject (e.g., subject 110 in FIG. 1A) to determine a cancer prediction, such as a prediction of risk of cancer, for the subject 110. Training risk prediction models and deploying risk prediction models are described in further detail below.

The enrichment module 165 selects for subjects for inclusion in a patient cohort. In various embodiments, the patient cohort is generated for enrollment in a clinical trial. For example, the enrichment module 165 generates a patient cohort (e.g., an enriched patient cohort) including a higher percentage of patients who will develop cancer within a period of time. This enriched patient cohort enables the enrolling of fewer patients in clinical trials, and/or identifies people that may benefit from therapies that intercept and prevent lung cancer.

The components of the cancer prediction system 130 are hereafter described in reference to two phases: 1) a training phase and 2) a deployment phase. More specifically, the training phase refers to the building and training of one or more risk prediction models by the risk training module 155 based on training data, such as training images captured from training individuals (e.g., individuals who are known to develop or not develop cancer within a period of time). Therefore, the models are trained using the training data such that during the deployment phase, implementation of the models by the risk deployment module 160 enables the prediction of a risk of cancer for a subject (e.g., subject 110 in FIG. 1A).

In some embodiments, the components of the cancer prediction system 130 are applied during one of the training phase and the deployment phase. For example, the risk training module 155 and training data store 170 are applied during the training phase to train a risk model. Additionally, the risk deployment module 160 is applied during the deployment phase. In various embodiments, the components of the cancer prediction system 130 can be performed by different parties depending on whether the components are applied during the training phase or the deployment phase. In such scenarios, the training and deployment of the prediction model are performed by different parties. For example, the risk training module 155 and training data store 170 applied during the training phase can be employed by a first party (e.g., to train a risk prediction model) and the risk deployment module 160 applied during the deployment phase can be performed by a second party (e.g., to deploy the risk prediction model).

III. Methods for Predicting Risk of Cancer

Figure 2A:
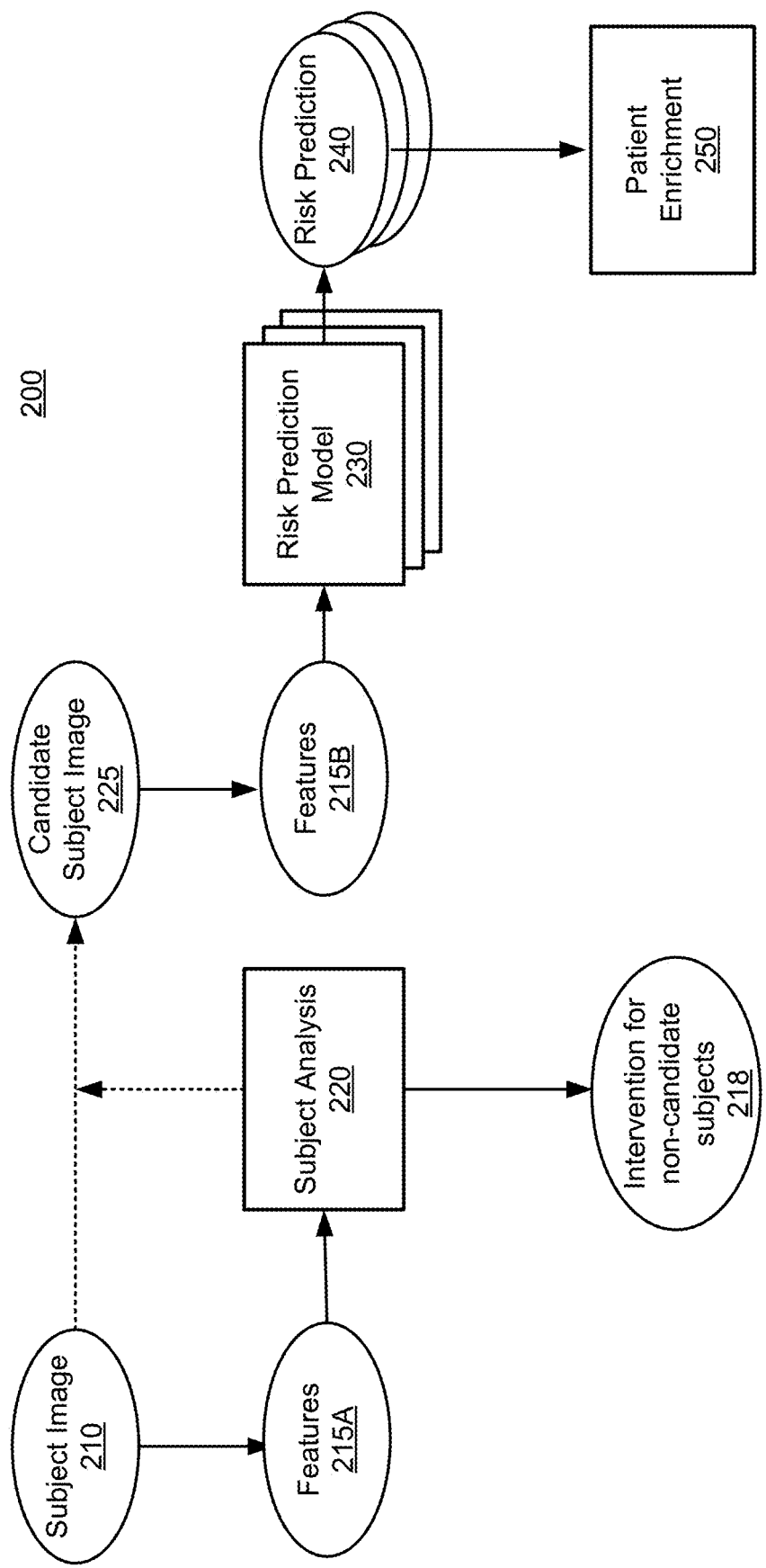
FIG. 2A depicts an example flow diagram for determining a risk of cancer for a subject for uses such as patient enrichment, in accordance with a first embodiment.

Embodiments described herein include methods for determining a risk of cancer for a subject by applying one or more trained risk prediction models. Such methods can be performed by the cancer prediction system 130 described in FIG. 1B. Reference will further be made to FIG. 2A, which depicts an example flow diagram 200 for determining a risk of cancer for a subject for uses such as patient enrichment, in accordance with an embodiment.

As shown in FIG. 2A, a subject image 210 captured from a subject (e.g., subject 110 in FIG. 1A) is obtained. In various embodiments, the subject image 210 is a CT image captured by performing a CT scan of the subject. In various embodiments, the subject image 210 is an X-ray image captured by performing an X-ray scan of the subject. In various embodiments, more than one subject image 210 is captured from the subject.

In various embodiments, the feature extract module 145 extracts features 215A of a subject. In various embodiments, features 215A of the subject include clinical data corresponding to the subject such as age, sex, ethnicity, smoking history, geographical location, pollution exposure, and/or family history of lung cancer. In various embodiments, the feature extraction module 145 (FIG. 1B) extracts features 215A from the subject image 210. In various embodiments, the feature extraction module 145 implements an image analysis algorithm to extract features 215A from the subject image 210. In various embodiments, the feature extraction module 145 implements an image analysis algorithm including a machine learning model that is trained to analyze and extract features from an image. Methods for extraction radiomic features are further described in Radiomics of Lung Nodules: A multi-institutional study of robustness and agreement of quantitative imaging features. Tomography. 2016; 2(4):430-437 and Radiomics: extracting more information from medical images using advanced feature analysis. Eur J Cancer 2012; 48(4):441-446, each of which is hereby incorporated by reference in its entirety.

In various embodiments, the feature extraction module 145 extracts at least 2 features from subject image 210. In various embodiments, the feature extraction module 145 extracts at least 3, at least 4, at least 5, at least 6, at least 7, at least 8, at least 9, or at least 10 features from subject image 210. In various embodiments, the feature extraction module 145 extracts at least 15, at least 20, at least 25, at least 30, at least 35, at least 40, or at least 45 features from subject image 210. In various embodiments, the feature extraction module 145 extracts at least 50 features from subject image 210. In various embodiments, the feature extraction module 145 extracts at least 100 features, at least 150 features, at least 200 features, at least 250 features, at least 300 features, at least 350 features, at least 400 features, at least 450 features, at least 500 features, at least 550 features, at least 600 features, at least 650 features, at least 700 features, at least 750 features, at least 800 features, at least 850 features, at least 900 features, at least 950 features, or at least 1000 features from a subject image 210. In various embodiments, the feature extraction module 145 extracts between 100 features and 1000 features. In various embodiments, the feature extraction module 145 extracts between 300 features and 900 features. In various embodiments, the feature extraction module 145 extracts between 500 features and 1000 features.

In various embodiments, the feature extraction module 145 extracts features 215A including nodule specific features. Nodule specific features refer to features of a lung nodule (e.g., a lung nodule that is present or absent in the subject image 210), the edge of the lung nodule, and/or the boundary/peri-nodule area. Example nodule specific features include nodule specific attenuation, nodule margin description, nodule size, nodule shape, nodule texture (e.g., smooth, spiculated, etc.), nodule diameter, and Lung-RADS score. In various embodiments, nodule specific features can be radiomic features that are extracted using an image processing algorithm, such as PyRadiomics. Example radiomic features can include first order statistics, 3D shape based features, 2D shape based features, Gray level co-occurrence matrix, gray level run length matrix, gray level size zone matrix, neighboring gray tone difference matrix, and gray level dependence matrix. In various embodiments, radiomic features are extracted from an image that has been transformed by applying a filter, such as a wavelet filter or a gaussian filter. Thus, any of first order statistics, 3D shape based features, 2D shape based features, gray level co-occurrence matrix, gray level run length matrix, gray level size zone matrix, neighboring gray tone difference matrix, and gray level dependence matrix can be extracted from a wavelet transformed image or a gaussian transformed image. In various embodiments, the feature extraction module 145 extracts longitudinal features including any of a change in a nodule specific feature between two or more timepoints. For example, given a first timepoint t0 and a second timepoint t1, a longitudinal feature of a lung nodule can be a change in a feature of lung nodule between timepoint t0 and timepoint t1. In particular embodiments, longitudinal features of a lung nodule include a change in nodule specific attenuation, change in nodule margin description, change in nodule size, change in nodule shape, change in nodule texture (e.g., smooth, spiculated, etc.), change in nodule diameter, change in Lung-RADS score, and change in radiomic features.

In particular embodiments, the feature extraction module 145 analyzes the subject image 210 and assigns a Lung-RADS score to the subject image 210 based on one or more of the extracted nodule-specific features. For example, based on one or more extracted nodule specific features (e.g., such as radiomics features), the feature extraction module 145 determines that the subject image 210 does not include a lung nodule. In such scenarios, the feature extraction module 145 can assign the subject image 210 a Lung-RADS score of 1. As another example, the feature extraction module 145 analyzes the subject image 210 and determines that the subject image 210 includes a nodule based on one or more of the extracted nodule-specific features. Then, based on the nodule-specific features, the feature extraction module 145 can assign a corresponding Lung-RADS score (e.g., Lung-RADS 2, Lung-RADS 3, Lung-RADS 4A, Lung-RADS 4B, or Lung-RADS 4×) according to Lung-RADS criteria, such as current Lung-RADS criteria shown in Table 1 or future Lung-RADS criteria.

In various embodiments, the feature extraction module 145 extracts features 215A including non-nodule specific features. Non-nodule specific features refer to any of lung parenchyma features (e.g., densitometric measures of the lung parenchyma and measures of interstitial changes in the lung parenchyma) and body composition measures of the musculature/chest wall. Densitometric measures of the lung parenchyma may include, for example, the percentage of the lung occupied by (i) low attenuation area (LAA), which is defined as the area/volume having an attenuation less than −950 Hounsfield Units (HU) and (ii) high attenuation area (HAA), which is defined as the area/volume of lung having attenuation between −600 HU and −250 HU, and the ratio between LAA in the upper lung zone to that in the lower lung zone. Measures of interstitial changes in the lung parenchyma include local histogram measures of the lung parenchyma, the percentage of lung occupied by, for example, normal tissue, centrilobular emphysema, centrilobular nodule, ground glass, honeycombing, linear scar, nodular, reticular, subpleural line, other emphysema and/or cyst. Body composition measures of the musculature/chest wall may include, for example, pectoralis major cross-sectional area, pectoralis minor cross-sectional area, pectoralis major lean cross-sectional area, pectoralis minor lean cross-sectional area, aggregate cross-sectional area of the left or right pectoralis major or minor muscles, and subcutaneous fat cross-sectional area.

In various embodiments, the feature extraction module 145 extracts longitudinal non-nodule specific features, which refer to longitudinal features of any of the aforementioned lung parenchyma features or aforementioned body composition features. For example, longitudinal features of the lung parenchyma can be a change in features of the lung parenchyma between two or more timepoints. Additionally, longitudinal features of the body composition can be a change in features of the body composition between two or more timepoints. For example, given a first timepoint t0 and a second timepoint t1, a longitudinal feature of the lung parenchyma or body composition can be a change in a feature of the lung parenchyma or body composition between timepoint t0 and timepoint t1. In particular embodiments, longitudinal features of the lung parenchyma include a change in the percentage of the lung occupied by (i) low attenuation area (LAA), which is defined as the area/volume having an attenuation less than −950 Hounsfield Units (HU) or a change in percentage of the lung occupied by (ii) high attenuation area (HAA), which is defined as the area/volume of lung having attenuation between −600 HU and −250 HU, or a change in the ratio between LAA in the upper lung zone to that in the lower lung zone (Ratio LAA). Longitudinal features of the lung parenchyma can further include changes in measures of interstitial changes in the lung parenchyma such as a change in local histogram measures of the lung parenchyma or a change in the percentage of lung occupied by, for example, normal tissue, centrilobular emphysema, centrilobular nodule, ground glass, honeycombing, linear scar, nodular, reticular, subpleural line, other emphysema and/or cyst. In particular embodiments, longitudinal features of the body composition include a change in pectoralis major cross-sectional area, change in pectoralis minor cross-sectional area, change in pectoralis major lean cross-sectional area, change in pectoralis minor lean cross-sectional area, change in aggregate cross-sectional area of the left or right pectoralis major or minor muscles, and change in subcutaneous fat cross-sectional area.

In various embodiments, the feature extraction module 145 extracts features 215A that include nodule specific features and non-nodule specific features. In various embodiments, the feature extraction module 145 extracts features 215A that include only non-nodule specific features. In particular embodiments, the feature extraction module 145 extracts features 215A that include only nodule specific features. In various embodiments, the feature extraction module 145 obtains nodule specific features that are determined by a third party. For example, the nodule specific features may have been determined by a trained professional (e.g., a radiologist) that analyzes the subject image 210. In various embodiments, the feature extraction module 145 extracts nodule specific features from a report generated by a third party. For example, the feature extraction module 145 extracts nodule specific features from a report generated by a trained professional (e.g., a radiologist) that analyzes the subject image 210.

The candidate subject module 150 (FIG. 1B) performs subject analysis 220 (shown in FIG. 2A) by analyzing the features 215A of the subject image 210. Based on the analysis, the candidate subject module 150 determines whether the subject is a candidate subject who is to undergo a risk prediction. Put another way, the subject analysis 220 is a screening process to identify candidate subjects who are eligible for a risk of cancer prediction. For example, subjects undergoing lung cancer screening that are determined not to have prevalent lung cancer are subsequently evaluated for their risk of developing future incident lung cancer. In various embodiments, a screening process is not performed and subject analysis 220 is omitted. Therefore, all subjects are taken as candidate subjects who undergo a subsequent risk prediction.

As one example, the candidate subject module 150 determines that a subject is a candidate subject for undergoing risk prediction if the subject's features 215A, such as clinical data of the subject, meets one or more criterion. For example, if the subject's features 215A indicate that the subject smokes above a threshold amount, the subject is deemed a candidate subject for undergoing risk prediction. As another example, the candidate subject module 150 determines that a subject is a candidate subject for undergoing risk prediction if the subject is a low risk cancer patient (e.g., a patient who does not currently have lung cancer, does not currently have a lung nodule indicative of cancer, or has less than a 15% chance (or other threshold depending on goal of predictive value) of currently having cancer). In various embodiments, the candidate subject module 150 determines that a subject is a non-candidate subject for undergoing risk prediction if the subject is a high risk cancer patient (e.g., a patient currently with lung cancer, a patient with a lung nodule that indicates high risk of developing lung cancer, or has greater than a 15% chance (or other threshold depending on goal of predictive value) of currently having cancer). As shown in FIG. 2A, if the subject analysis 220 determines that the subject is a candidate subject, then the subject image 210 is taken as the candidate subject image 225 (shown by the dotted lines) for subsequent risk prediction analysis. Alternatively, if the subject analysis 220 determines that the subject is a non-candidate subject, the patient does not further undergo risk prediction analysis or may return to the current standard of care (e.g., annual CT scans for cancer screening). As an example, an intervention for non-candidate subjects 218 can be provided to the subject. For example, a non-candidate subject may be a subject already with lung cancer or with a lung nodule that indicates that the subject has advanced lung cancer. Thus, the non-candidate subject need not undergo a risk of cancer prediction and instead, can be provided an intervention for non-candidate subjects 218 can include a cancer biopsy and/or administration of a therapeutic agent (e.g., chemotherapy, radiation) to treat the non-candidate subject's lung cancer. As another example, a non-candidate subject may be a subject who falls outside of certain risk criteria (e.g., subject does not meet age and/or smoking criteria) and therefore, is at low risk of developing cancer. Thus, the non-candidate subject need not undergo a risk of cancer prediction and can be provided guidance (e.g., continued healthy lifestyle or recommendation of lifestyle changes).

In various embodiments, the candidate subject module 150 determines that a subject is a candidate subject based on features 215A that include nodule specific features. As an example, the nodule-specific features can include a Lung-RADS score, such as Lung-RADS 0, Lung-RADS 1, Lung-RADS 2, Lung-RADS 3, Lung-RADS 4A, Lung-RADS 4B, or Lung-RADS 4x. A summary of Lung-RADS score classifications and corresponding characteristics of lung nodules is described in Table 1. In various embodiments, the candidate subject module 150 determines a Lung-RADS score for the subject based on the features 215A, such as nodule specific features. For example, the nodule specific features can include one or more of nodule specific attenuation, nodule margin description, nodule size, nodule shape, nodule texture (e.g., smooth, spiculated, etc.), nodule diameter, Lung-RADS score, and/or radiomic features such as first order statistics, 3D shape based features, 2D shape based features, gray level co-occurrence matrix, gray level run length matrix, gray level size zone matrix, neighboring gray tone difference matrix, and gray level dependence matrix. Thus, if the nodule attenuation feature indicates that the lung nodule is a solid nodule and the nodule margin and/or nodule diameter features indicate that the lung nodule is 5 mm, the candidate subject module 150 can assign a Lung-RADS score of 2 based on criteria specified in Table 1.

In various embodiments, the candidate subject module 150 determines that a subject is a candidate subject if the subject is assigned a Lung-RADS score of 0. In various embodiments, the candidate subject module 150 determines that a subject is a candidate subject if the subject is assigned a Lung-RADS score of 1. In various embodiments, the candidate subject module 150 determines that a subject is a candidate subject if the subject is assigned a Lung-RADS score of 2. In various embodiments, the candidate subject module 150 determines that a subject is a candidate subject if the subject is assigned a Lung-RADS score of 3. In various embodiments, the candidate subject module 150 determines that a subject is a candidate subject if the subject is assigned a Lung-RADS score of 4A. In various embodiments, the candidate subject module 150 determines that a subject is a candidate subject if the subject is assigned a Lung-RADS score of 0. In various embodiments, the candidate subject module 150 determines that a subject is a candidate subject if the subject is assigned a Lung-RADS score of 1. In various embodiments, the candidate subject module 150 determines that a subject is a candidate subject if the subject is assigned a Lung-RADS score of 2. In various embodiments, the candidate subject module 150 determines that a subject is a candidate subject if the subject is assigned a Lung-RADS score of 3. In various embodiments, the candidate subject module 150 determines that a subject is a candidate subject if the subject is assigned a Lung-RADS score of 4A. In various embodiments, the candidate subject module 150 determines that a subject is a candidate subject if the subject is assigned a Lung-RADS score of 4B. In various embodiments, the candidate subject module 150 determines that a subject is a candidate subject if the subject is assigned a Lung-RADS score of 4X. In various embodiments, the candidate subject module 150 determines that a subject is a candidate subject if the subject is assigned a Lung-RADS score of 0 or 1. In various embodiments, the candidate subject module 150 determines that a subject is a candidate subject if the subject is assigned a Lung-RADS score of 0, 1, or 2. In various embodiments, the candidate subject module 150 determines that a subject is a candidate subject if the subject is assigned a Lung-RADS score of 0, 1, 2, or 3. In various embodiments, the candidate subject module 150 determines that a subject is a candidate subject if the subject is assigned a Lung-RADS score of 1, 2, or 3. In various embodiments, the candidate subject module 150 determines that a subject is a candidate subject if the subject is assigned a Lung-RADS score of 4A-4X. In various embodiments, the candidate subject module 150 determines that a subject is a candidate subject if the subject is assigned a Lung-RADS score of 4A-4B. In various embodiments, the candidate subject module 150 determines that a subject is a candidate subject if the subject is assigned a Lung-RADS score of 3-4A. In various embodiments, the candidate subject module 150 determines that a subject is a candidate subject if the subject is assigned a Lung-RADS score of 2-4A. In various embodiments, the candidate subject module 150 determines that a subject is a candidate subject if the subject is assigned a Lung-RADS score of 2-3.

In various embodiments, the candidate subject module 150 determines that a subject is a non-candidate subject if the subject is assigned a Lung-RADS score of 3. In various embodiments, the candidate subject module 150 determines that a subject is a non-candidate subject if the subject is assigned a Lung-RADS score of 4A. In various embodiments, the candidate subject module 150 determines that a subject is a non-candidate subject if the subject is assigned a Lung-RADS score of 4B. In various embodiments, the candidate subject module 150 determines that a subject is a non-candidate subject if the subject is assigned a Lung-RADS score of 4A or 4B. In various embodiments, the candidate subject module 150 determines that a subject is a non-candidate subject if the subject is assigned a Lung-RADS score of 4A, 4B or 4X. In various embodiments, the candidate subject module 150 determines that a subject is a non-candidate subject if the subject is assigned a Lung-RADS score of 3, 4A, or 4B. In various embodiments, the candidate subject module 150 determines that a subject is a non-candidate subject if the subject is assigned a Lung-RADS score of 3, 4A, 4B, or 4X. In various embodiments, the candidate subject module 150 determines that a subject is a non-candidate subject if the subject is assigned a Lung-RADS score of 0.

In various embodiments, the candidate subject module 150 determines that a subject is a candidate subject if the nodule specific features indicate that the subject does not have a lung nodule. For example, the nodule specific features can include one or more of nodule attenuation, nodule margin description, or nodule diameter. Thus, if the nodule specific features indicates that the subject image 210 does not include a nodule (e.g., lack of attenuation, lack of margins, or near-zero or zero diameter), then the candidate subject module 150 determines that the subject is a candidate subject. Thereafter, a prediction can be generated for the candidate subject (e.g., prediction generated based on at least non-nodule features of the candidate subject).

In various embodiments, the candidate subject module 150 determines that a subject is a candidate subject even if the subject has a lung nodule. For example, if the nodule specific features indicate that the subject has a lung nodule, the candidate subject module 150 can further analyze the nodule specific features to classify the nodule as a higher risk nodule or a lower risk nodule. In various embodiments, the candidate subject module 150 can classify a nodule based on whether the nodule is a solid nodule, a semi-solid nodule, or a non-solid nodule. For example, the candidate subject module 150 can classify a nodule as a higher risk nodule if it is a solid nodule or a semi-solid nodule and can classify a nodule as a lower risk nodule if it is a non-solid nodule. In various embodiments, the candidate subject module 150 determines that a subject is a candidate subject if the subject has a lower risk nodule. The candidate subject module 150 can determine that a subject is a non-candidate subject if the subject has a higher risk nodule.

Returning to FIG. 2A, following subject analysis 220, a subject image 210 from a candidate subject is now deemed a candidate subject image 225. The feature extraction module 145 extracts features 215B from the candidate subject image 225. In various embodiments, the feature extraction module 145 extracts features 215B including one or both of nodule specific features and non-nodule specific features from the candidate subject image 225. In various embodiments, the feature extraction module 145 extracts features 215A that include only non-nodule specific features. In various embodiments, the feature extraction module 145 extracts features 215A that include only nodule specific features. In various embodiments, the feature extraction module 145 obtains nodule specific features of candidate subject image 225 that are determined by a third party. For example, the nodule specific features may have been determined by a trained professional (e.g., a radiologist) that analyzes the candidate subject image 225. In various embodiments, the feature extraction module 145 extracts nodule specific features from a report generated by a third party. For example, the feature extraction module 145 extracts nodule specific features from a report generated by a trained professional (e.g., a radiologist) that analyzes the subject image 225.

In various embodiments, one or more of features 215B are the same as one or more of features 215A. Therefore, the same features need not be extracted again and can be reused. For example, nodule specific features that were previously extracted from subject image 210 as features 215A can be the same nodule specific features that are included in features 215B. In various embodiments, all of the features 215B were previously extracted from the subject image 210 and therefore, the previously extracted features can be reused here as features 215B. For example, the feature extraction module 145 may extract features 215A and features 215B prior to subject analysis 220. Thus, features 215B need not be further extracted from candidate subject image 225 and can be reused here.

In various embodiments, features 215B includes additional features that were not included in features 215A. For example, features 215B includes non-nodule specific features that were not previously included in features 215A. Thus, the feature extraction module 145 extracts these additional features that were not previously included in features 215A.

In various embodiments, the feature extraction module 145 extracts at least 2 features from candidate subject image 225. In various embodiments, the feature extraction module 145 extracts at least 3, at least 4, at least 5, at least 6, at least 7, at least 8, at least 9, or at least 10 features from candidate subject image 225. In various embodiments, the feature extraction module 145 extracts at least 15, at least 20, at least 25, at least 30, at least 35, at least 40, or at least 45 features from candidate subject image 225. In various embodiments, the feature extraction module 145 extracts at least 50 features from candidate subject image 225. In various embodiments, the feature extraction module 145 extracts at least 100 features, at least 150 features, at least 200 features, at least 250 features, at least 300 features, at least 350 features, at least 400 features, at least 450 features, at least 500 features, at least 550 features, at least 600 features, at least 650 features, at least 700 features, at least 750 features, at least 800 features, at least 850 features, at least 900 features, at least 950 features, or at least 1000 features from candidate subject image 225. In various embodiments, the feature extraction module 145 extracts between 100 features and 1000 features from candidate subject image 225. In various embodiments, the feature extraction module 145 extracts between 300 features and 900 features from candidate subject image 225. In various embodiments, the feature extraction module 145 extracts between 500 features and 1000 features from candidate subject image 225.

The risk deployment module 160 (FIG. 1B) provides the extracted features 215B to trained risk prediction models 230 (shown in FIG. 2A) to generate a risk prediction 240. In various embodiments, as shown in FIG. 2A, the risk deployment module 160 provides the extracted features 215 to multiple trained risk prediction models 230 to generate multiple risk predictions 240. In various embodiments, a risk prediction model is trained to generate a risk of cancer prediction within a time period (e.g., future risk of cancer within 1 year, within 3 years, or within 5 years). In various embodiments, a risk prediction model is trained to generate a risk for currently existing or prevalent cancer. Therefore, to generate a prediction for multiple time periods, the risk deployment module 160 selects and deploys different risk prediction models to analyze the extracted features 215B. For example, the risk deployment module 160 can deploy a first risk prediction model trained to predict risk of cancer within a first time period and can further deploy a second risk prediction model trained to predict risk of cancer within a second time period.

In various embodiments, the risk deployment module 160 deploys 1, 2, 3, 4, 5, 6, 7, 8, 9, 10, 11, 12, 13, 14, 15, 16, 17, 18, 19, or 20 different risk prediction models to generate risk of cancer over 1, 2, 3, 4, 5, 6, 7, 8, 9, 10, 11, 12, 13, 14, 15, 16, 17, 18, 19, or 20 different time periods, respectively. In various embodiments, the risk deployment module 160 deploys 5 different risk prediction models to generate risk of cancer over 5 different time periods. In various embodiments, the risk deployment module 160 deploys 3 different risk prediction models to generate risk of cancer over 3 different time periods. For example, the risk deployment module 160 deploys a 1 year risk prediction model, a 3 year risk prediction model, and a 5 year risk prediction model to generate predictions of risk of cancer within 1 year, 3 years, and 5 years, respectively.

In various embodiments, each of the one or more risk prediction models 230 that are deployed to analyze the features 215B were previously trained on training images that were separated into different regions (e.g., different lung regions). For example, a first risk prediction model 230 may be trained to predict presence of cancer within a first region of the lung, a second risk prediction model 230 may be trained to predict presence of cancer within a second region of the lung, and a third risk prediction model 230 may be trained to predict presence of cancer within a third region of the lung. As an example, different lung regions can include the upper, middle, and lower third of the lungs by volume or separate lobes of the lungs. Thus, the risk predictions 240 generated for the subject may be risk of cancer within particular regions (e.g., lung regions).

In various embodiments, each of the one or more risk prediction models 230 that are deployed to analyze the features 215B were previously trained using a cohort of training individuals that aligns with the cohort of candidate subjects that were determined as a result of the subject analysis 220. Put another way, the risk prediction models 230 were previously trained using training individuals that would qualify as candidate subjects if they were to undergo the subject analysis 220.

In various embodiments, one or more of the training individuals used to train the risk prediction models 230 share at least one feature with the candidate subject. As an example, if the candidate subject is classified as Lung-RADS 1, one or more of the training individuals used to train the risk prediction models 230 were also classified as Lung-RADS 1. In various embodiments, the risk prediction models 230 may be trained using training images captured from training individuals that were classified as Lung-RADS 1 (referred to as a Lung-RADS 1 risk prediction model). In various embodiments, the risk prediction models 230 may be trained using training images captured from training individuals that were classified as Lung-RADS 1 or Lung-RADS 2 (referred to as a Lung-RADS 1-2 risk prediction model). In various embodiments, the risk prediction models 230 may be trained using training images captured from training individuals that were classified as Lung-RADS 1, Lung-RADS 2, or Lung-RADS 3 (referred to as a Lung-RADS 1-3 risk prediction model). In various embodiments, the risk prediction models 230 may be trained using training images captured from training individuals that were classified as Lung-RADS 1, Lung-RADS 2, Lung-RADS 3, or Lung-RADS 4A (referred to as a Lung-RADS 1-4A risk prediction model). In various embodiments, the risk prediction models 230 may be trained using training images captured from training individuals that were classified as Lung-RADS 1, Lung-RADS 2, Lung-RADS 3, Lung-RADS 4A, or Lung-RADS 4B (referred to as a Lung-RADS 1-4B risk prediction model). In various embodiments, the risk prediction models 230 may be trained using training images captured from training individuals that were classified as Lung-RADS 1, Lung-RADS 2, Lung-RADS 3, Lung-RADS 4A, Lung-RADS 4B, or Lung-RADS 4X (referred to as a Lung-RADS 1-4× risk prediction model). In various embodiments, the risk prediction models 230 may be trained using training images captured from training individuals that were classified as Lung-RADS 2, Lung-RADS 3, Lung-RADS 4A, and Lung-RADS 4B (referred to as a Lung-RADS 2-4B risk prediction model).

In a scenario in which a candidate subject is classified as Lung-RADS 1 (e.g., classified either through subject analysis 220 or previously classified by a third party), then the risk deployment module 160 deploys one or more risk prediction models 230 that were trained using training images captured from at least one training individual that was also previously classified as Lung-RADS 1. Thus, the risk deployment module 160 can deploy one or more risk prediction models 230 that each are any of a Lung-RADS 1 prediction model, Lung-RADS 1-2 prediction model, Lung-RADS 1-3 prediction model, Lung-RADS 1-4A prediction model, Lung-RADS 1-4B prediction model, or Lung-RADS 1-4× prediction model. In particular embodiments, the risk deployment module 160 deploys a Lung-RADS 1 prediction model for a Lung-RADS 1 candidate subject. In particular embodiments, the risk deployment module 160 deploys a Lung-RADS 1-2 prediction model for a Lung-RADS 1 candidate subject. In particular embodiments, the risk deployment module 160 deploys a Lung-RADS 1-3 prediction model for a Lung-RADS 1 candidate subject.

In a scenario in which a candidate subject is classified as Lung-RADS 2 (e.g., classified either through subject analysis 220 or previously classified by a third party), then the risk deployment module 160 deploys one or more risk prediction models 230 that were trained using training images captured from at least one training individual that was also previously classified as Lung-RADS 2. Thus, the risk deployment module 160 can deploy one or more risk prediction models 230 that each are any of Lung-RADS 1-2 prediction model, Lung-RADS 1-3 prediction model, Lung-RADS 1-4A prediction model, Lung-RADS 1-4B prediction model, or Lung-RADS 1-4× prediction model. In particular embodiments, the risk deployment module 160 deploys a Lung-RADS 1-2 prediction model for a Lung-RADS 2 candidate subject. In particular embodiments, the risk deployment module 160 deploys a Lung-RADS 1-3 prediction model for a Lung-RADS 2 candidate subject.

In a scenario in which a candidate subject is classified as Lung-RADS 3 (e.g., classified either through subject analysis 220 or previously classified by a third party), then the risk deployment module 160 deploys one or more risk prediction models 230 that were trained using training images captured from at least one training individual that was also previously classified as Lung-RADS 3. Thus, the risk deployment module 160 can deploy one or more risk prediction models 230 that each are any of a Lung-RADS 1-3 prediction model, Lung-RADS 1-4A prediction model, Lung-RADS 1-4B prediction model, or Lung-RADS 1-4x prediction model.

In a scenario in which a candidate subject is classified as Lung-RADS 4A (e.g., classified either through subject analysis 220 or previously classified by a third party), then the risk deployment module 160 deploys one or more risk prediction models 230 that were trained using training images captured from at least one training individual that was also previously classified as Lung-RADS 4A. Thus, the risk deployment module 160 can deploy one or more risk prediction models 230 that each are any of a Lung-RADS 1-4A prediction model, Lung-RADS 1-4B prediction model, or Lung-RADS 1-4x prediction model.

In a scenario in which a candidate subject is classified as Lung-RADS 4B (e.g., classified either through subject analysis 220 or previously classified by a third party), then the risk deployment module 160 deploys one or more risk prediction models 230 that were trained using training images captured from at least one training individual that was also previously classified as Lung-RADS 4B. Thus, the risk deployment module 160 can deploy one or more risk prediction models 230 that each are any of a Lung-RADS 1-4B prediction model, or Lung-RADS 1-4x prediction model.

In a scenario in which a candidate subject is classified as Lung-RADS 4X (e.g., classified either through subject analysis 220 or previously classified by a third party), then the risk deployment module 160 deploys one or more risk prediction models 230 that were trained using training images captured from at least one training individual that was also previously classified as Lung-RADS 4X. Thus, the risk deployment module 160 can deploy one or more risk prediction models 230 that each are a Lung-RADS 1-4x prediction model.

In various embodiments, risk prediction models are 1) trained using a cohort of training individuals that aligns with the cohort of candidate subjects that were determined as a result of the subject analysis 220 and 2) trained to generate a risk of cancer prediction within a time period (e.g., existing or prevalent cancer, or future risk of cancer within 1 year, within 3 years, or within 5 years). For example, to generate risk predictions 240 for a candidate subject, the risk deployment module 160 applies one or more risk prediction models 230 that 1) are trained using one or more training individuals that share at least one feature with the candidate subject and 2) are trained to predict risk of cancer within different time periods.

In a scenario in which a candidate subject is classified as Lung-RADS "Z" (e.g., classified either through subject analysis 220 or previously classified by a third party), the risk deployment module 160 deploys one or more risk prediction models 230 that 1) were trained using training images captured from at least one training individual that was also previously classified as Lung-RADS "Z" and 2) predicts risk of cancer within different time periods. As used herein, these risk prediction models are referred to as a "M year, Lung-RADS X-Y prediction model" where "M" refers to the time period and "X-Y" refer to the range of Lung-RADS scores of the training individuals. For example, a 1 year, Lung-RADS 1-3 prediction model refers to a risk prediction model trained using training individuals previously classified in Lung-RADS 1-3, and trained to predict a risk of cancer within 1 year.

In various embodiments, for a candidate subject classified as Lung-RADS 1, the risk deployment module 160 deploys one or more M year, Lung-RADS X-Y prediction models where the "M" is variable, but the "X" and "Y" are fixed. For example, for a candidate subject classified as Lung-RADS 1, "M" can range from 1-5 years, whereas X=1 and Y=any value from 1 to 4B. As one example, Y=3 and therefore, the risk deployment module 160 can deploy a 1 year, Lung-RADS 1-3 prediction model, a 2 year, Lung-RADS 1-3 prediction model, a 3 year, Lung-RADS 1-3 prediction model, a 4 year, Lung-RADS 1-3 prediction model, and a 5 year, Lung-RADS 1-3 prediction model. In other embodiments, the risk deployment module 160 can deploy additional risk prediction models than described here (e.g., range of M is 1-10, 1-15, or 1-20 years e.g., X and Y are differently selected to provide different ranges of Lung-RADS scores).

In particular embodiments where a candidate subject is classified as Lung-RADS 1, the risk deployment module 160 deploys 1) a first risk prediction model 230 that predicts a future risk of cancer within 1 year (e.g., a 1 year, Lung-RADS 1-3 prediction model), 2) a second risk prediction model 230 that predicts a future of cancer within 3 years (e.g., a 3 year, Lung-RADS 1-3 prediction model), and 3) a third risk prediction model 230 that predicts a future of cancer within 5 years (e.g., a 5 year, Lung-RADS 1-3 prediction model).

In particular embodiments where a candidate subject is classified as Lung-RADS 2, the risk deployment module 160 deploys 1) a first risk prediction model 230 that predicts a future risk of cancer within 1 year (e.g., a 1 year, Lung-RADS 1-3 prediction model), 2) a second risk prediction model 230 that predicts a future of cancer within 3 years (e.g., a 3 year, Lung-RADS 1-3 prediction model), and 3) a third risk prediction model 230 that predicts a future of cancer within 5 years (e.g., a 5 year, Lung-RADS 1-3 prediction model).

In particular embodiments where a candidate subject is classified as Lung-RADS 3, the risk deployment module 160 deploys 1) a first risk prediction model 230 that predicts a future risk of cancer within 1 year (e.g., a 1 year, Lung-RADS 1-3 prediction model), 2) a second risk prediction model 230 that predicts a future of cancer within 3 years (e.g., a 3 year, Lung-RADS 1-3 prediction model), and 3) a third risk prediction model 230 that predicts a future of cancer within 5 years (e.g., a 5 year, Lung-RADS 1-3 prediction model).

In particular embodiments where a candidate subject is classified as Lung-RADS 4A, the risk deployment module 160 deploys 1) a first risk prediction model 230 that predicts a future risk of cancer within 1 year (e.g., a 1 year, Lung-RADS 1-4A prediction model), 2) a second risk prediction model 230 that predicts a future of cancer within 3 years (e.g., a 3 year, Lung-RADS 1-4A prediction model), and 3) a third risk prediction model 230 that predicts a future of cancer within 5 years (e.g., a 5 year, Lung-RADS 1-4A prediction model).

In particular embodiments where a candidate subject is classified as Lung-RADS 4B, the risk deployment module 160 deploys 1) a first risk prediction model 230 that predicts a future risk of cancer within 1 year (e.g., a 1 year, Lung-RADS 1-4B prediction model), 2) a second risk prediction model 230 that predicts a future of cancer within 3 years (e.g., a 3 year, Lung-RADS 1-4B prediction model), and 3) a third risk prediction model 230 that predicts a future of cancer within 5 years (e.g., a 5 year, Lung-RADS 1-4B prediction model).

In particular embodiments where a candidate subject is classified as Lung-RADS 4X, the risk deployment module 160 deploys 1) a first risk prediction model 230 that predicts a future risk of cancer within 1 year (e.g., a 1 year, Lung-RADS 1-4× prediction model), 2) a second risk prediction model 230 that predicts a future of cancer within 3 years (e.g., a 3 year, Lung-RADS 1-4× prediction model), and 3) a third risk prediction model 230 that predicts a future of cancer within 5 years (e.g., a 5 year, Lung-RADS 1-4× prediction model).

As shown in FIG. 2A, the risk predictions 240 can be used for patient enrichment 250. For example, the subject can be included in one or more patient cohorts that are to be enrolled in a clinical study. Methods for patient enrichment are described in further detail below.

Figure 2B:
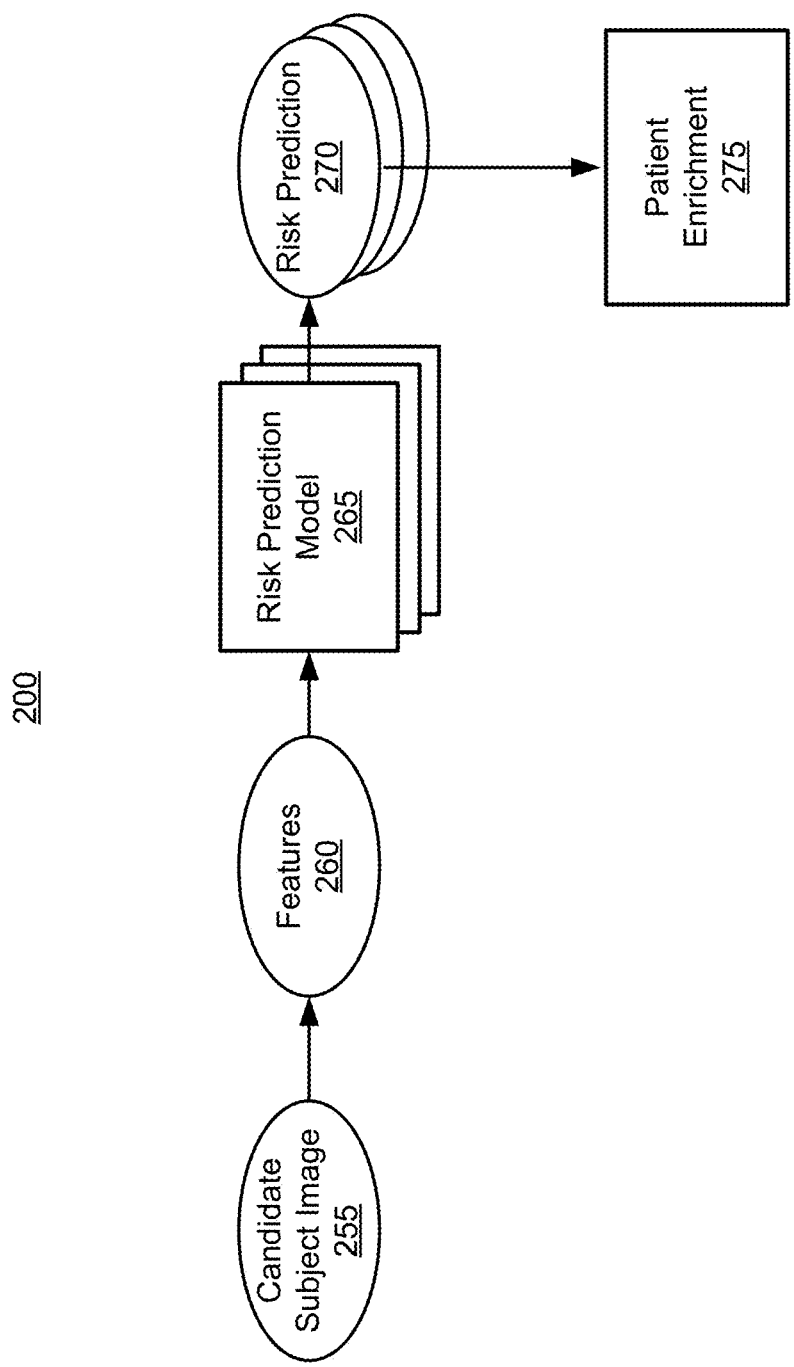
FIG. 2B depicts an example flow diagram for determining a risk of cancer for a subject for uses such as patient enrichment, in accordance with a second embodiment.

Reference is now made to FIG. 2B, which depicts an example flow diagram for determining a risk of cancer for a subject for uses such as patient enrichment, in accordance with a second embodiment. Here, FIG. 2B differs from FIG. 2A in that FIG. 2B does not include a subject analysis step (e.g., step 220 shown in FIG. 2A). Thus, FIG. 2B depicts an embodiment where subjects do not undergo a screening. Instead, all subjects are candidate subjects who subsequently undergo risk prediction. In various embodiments, subjects either have or do not have a lung nodule. In various embodiments, subjects can be previously classified in any one of Lung-RADS 1, Lung-RADS 2, Lung-RADS 3, Lung-RADS 4A, Lung-RADS 4B, or Lung-RADS 4X. Thus, in such embodiments, all subjects, regardless of their lung nodule staging and/or Lung-RADS score, undergo risk prediction.

As shown in FIG. 2B, the candidate subject image 255 undergoes feature extraction to obtain features 260. In various embodiments, features 260 include one or both of nodule specific features and non-nodule specific features of the candidate subject image 225. In various embodiments, features 260 include only non-nodule specific features. In various embodiments, features 260 include only nodule specific features. In various embodiments, the feature extraction module 140 extracts nodule specific features by implementing an image analysis algorithm, such as an image analysis algorithm that involves implementing a trained machine learning model. In various embodiments, the feature extraction module 140 extracts nodule specific features by implementing PyRadiomics. PyRadiomics is described in further detail in "Computational radiomics system to decode the radiographic phenotype." Cancer Research; 77(21): e104-e107, which is hereby incorporated by reference in its entirety.

In various embodiments, nodule specific features of candidate subject image 255 are determined by a third party. For example, the nodule specific features may have been determined by a trained professional (e.g., a radiologist) that analyzes the candidate subject image 255. In various embodiments, the feature extraction module 145 extracts nodule specific features from a report generated by a third party. For example, the feature extraction module 145 extracts nodule specific features from a report generated by a trained professional (e.g., a radiologist) that analyzes the subject image 225.

The risk deployment module 260 applies one or more risk prediction models 265 to analyze the features 260 to generate the risk prediction 270. Thus, the risk prediction 270 can be used for patient enrichment 275. In various embodiments, the deployment of the risk prediction models 265 to generate the risk prediction 270 as shown in FIG. 2B is the same process as deploying risk prediction models 230 to generate risk predictions 240 as shown in FIG. 2A.

Here, the one or more risk prediction models 265 are trained on training images obtained from training individuals that span a partial range or the full range of possible subjects. For example, the risk prediction models 265 are trained using training images captured from training individuals either having a lung nodule or not having a lung nodule. As another example, the risk prediction models 265 are trained using training images captured from training individuals of any of Lung-RADS 1, Lung-RADS 2, Lung-RADS 3, Lung-RADS 4A, Lung-RADS 4B, or Lung-RADS 4X (e.g., Lung-RADS 1-4× risk prediction models).

In various embodiments, the risk deployment module 260 deploys multiple risk models 265 to predict multiple risk predictions 270. For example, the risk deployment module 260 deploys multiple M year, Lung-RADS 1-4× risk prediction models, where "M" refers to the time period in which cancer risk is being evaluated. In various embodiments, "M" is at least 1 year, at least 2 years, at least 3 years, at least 4 years, at least 5 years, at least 6 years, at least 7 years, at least 8 years, at least 9 years, at least 10 years, at least 11 years, at least 12 years, at least 13 years, at least 14 years, at least 15 years, at least 16 years, at least 17 years, at least 18 years, at least 19 years, and/or at least 20 years. In particular embodiments, the risk deployment module 260 deploys 1) a 1 year, Lung-RADS 1-4× risk prediction model, 2) a 3 year, Lung-RADS 1-4× risk prediction model, and 3) a 5 year, Lung-RADS 1-4× risk prediction model, thereby generating risk of cancer predictions for 1 year, 3 year, and 5 year time periods.

In various embodiments, upon being deployed, a risk prediction model analyzes the extracted image features and generates a predicted score that can be indicative of whether the subject is likely to develop cancer within a time period. For example, the risk prediction model can be a regression model (e.g., a logistic regression or linear regression model) that calculates a predicted score by combining a set of trained parameters with values of the extracted image features. As another example, the risk prediction model can be a neural network model that calculates a predicted score by combining a set of trained parameters associated with nodes and layers of the neural network with values of the extracted image features. As another example, the risk prediction model can be a random forest model that calculates a predicted score by combining a set of trained parameters associated with decision tree nodes with values of the extracted image features. As another example, the risk prediction model can be a gradient boosted machine model that calculates a predicted score by combining a set of trained parameters associated with decision tree nodes with values of the extracted image features. As another example, the risk prediction model can be a support vector machine that calculates a predicted score by combining a set of trained parameters with values of the extracted image features.

In various embodiments, the risk prediction model compares the predicted score to one or more reference scores. In various embodiments, the one or more reference scores are threshold cutoff values. For example, a threshold cutoff value can be between 0 and 1, such as 0.1, 0.2, 0.3, 0.4, 0.5, 0.6, 0.7, 0.8, or 0.9. In particular embodiments, a threshold value is 0.1. In particular embodiments, a threshold value is 0.3. Therefore, if the predicted score is above the threshold reference score, the subject is classified into one category (e.g., likely to develop cancer). If the predicted score is below the threshold reference score, the subject is classified into a different category (e.g., unlikely to develop cancer).

In various embodiments, multiple reference threshold scores can be implemented to create multiple classification groups. For example, a first threshold value is 0.1 and a second threshold value is 0.3. Therefore, if the predicted score is below the first threshold value, the subject is classified into a first category (e.g., unlikely to develop cancer. If the predicted score is between the first and second threshold values, the subject is classified into a second category (e.g., low risk of developing cancer). If the predicted score is greater than the second threshold value, the subject is classified into a third category (e.g., high risk of developing cancer).

As one example, a reference score corresponds to one or more training individuals. For example, a reference score can correspond to training individuals that were known to develop cancer within the time period. As another example, a reference score can correspond to training individuals that were known to not develop cancer within the time period. Thus, if the predicted score for the subject is not significantly different (e.g., p-value >0.05) in comparison to the reference score corresponding to training individuals that were known to develop cancer within the time period, then the risk prediction model can classify the subject as likely to develop cancer within the time period. If the predicted score for the subject is significantly different (e.g., p-value <0.05) in comparison to the reference score corresponding to training individuals that were known to develop cancer within the time period, then the risk prediction model can classify the subject as not likely to develop cancer within the time period. If the predicted score for the subject is not significantly different (e.g., p-value >0.05) in comparison to the reference score corresponding to training individuals that were known to not develop cancer within the time period, then the risk prediction model can classify the subject as not likely to develop cancer within the time period. If the predicted score for the subject is significantly different (e.g., p-value <0.05) in comparison to the reference score corresponding to training individuals that were known to not develop cancer within the time period, then the risk prediction model can classify the subject as likely to develop cancer within the time period.

In various embodiments, during training, a risk of cancer threshold is defined that demarcates high from low risk subjects. Then, only the high risk subjects are included in any given model. In various embodiments, each risk prediction model has a unique cancer threshold used to demarcate subjects into high or low risk. Once those thresholds are defined for each risk prediction model, the risk prediction model is deployed for a subject to predict a risk of cancer. If that risk is above the threshold defined in training, the subject can be classified as having a high risk of cancer.

As shown in FIG. 2B, the risk predictions 270 can be used for patient enrichment 275. For example, the subject can be included in one or more patient cohorts that are to be enrolled in a clinical. Methods for patient enrichment are described in further detail below.

In various embodiments, the risk predictions 270 for the subject can be displayed to a user e.g., a clinician user. Thus, the clinician user can inform the subject of the risk of cancer that is predicted for the subject. In various embodiments, additional/other information can be displayed to a user e.g., a clinician user. For example, if a risk of cancer prediction for a subject indicates that the subject is likely to develop cancer within a time period, information such as the features that most heavily contributed to the risk of cancer prediction can be displayed to the user e.g., clinician user. For example, a subject predicted to have a risk of cancer can be largely due to a percentage of the subject's lung occupied by centrilobular emphysema. Thus, the identification of the feature and/or the value of the feature (e.g., percentage of the subject's lung occupied by centrilobular emphysema) can be displayed to a user e.g., clinician user. In various embodiments, the top 1, top 2, top 3, top 4, top 5, top 6, top 7, top 8, top 9, top 10, top 11, top 12, top 13, top 14, top 15, top 16, top 17, top 18, top 19, top 20, top 21, top 22, top 23, top 24, top 25, top 30, top 35, top 40, top 45, top 50, top 55, top 60, top 65, top 70, top 75, top 80, top 85, top 90, top 95, or top 100 features that most heavily contributed to the risk of cancer prediction for the subject can be displayed to a user e.g., clinician user. The display of the heavily contributing features can provide context to the clinician user in understanding the features that resulted in the risk of cancer prediction.

IV. Methods of Patient Enrichment

Generally, risk of cancer predictions from the risk prediction models are used for patient enrichment. For example, the risk of cancer predictions provide insight as to whether a subject is likely to develop cancer within time periods (e.g., within 1 year, within 3 years, or within 5 years). Thus, for subjects that are predicted to develop cancer within a particular time period, the subjects can be selected for inclusion in a patient cohort that is to be enrolled in a clinical trial. Given the insight provided by the risk of cancer predictions, this enables the enrollment of fewer subjects in patient cohorts for clinical trials. Thus, fewer resources are needed conducting the clinical trial and tracking the subjects in the patient cohort. Additionally, subjects that are not included in the patient cohort (e.g., subjects that are predicted to not develop cancer within a time period) can be used for other purposes (e.g., enrolled in other clinical trials).

In various embodiments, a subject is selected for inclusion in a patient cohort based on one or more of the multiple risk predictions generated for the patient. For example, the subject may have a first risk prediction indicating that the subject will not develop cancer within 1 year, will not develop cancer within 3 years, but is likely to develop cancer within 5 years. Therefore, the subject is selected for inclusion in a patient cohort for enrollment in a cancer clinical trial involving administration of a prophylactic therapeutic agent.

As another example, the subject may have a first risk prediction indicating that the subject is likely to develop cancer within 1 year and therefore, is also likely to develop cancer within 3 years and 5 years. Thus, the subject is selected for inclusion in a patient cohort for enrollment in a cancer clinical trial involving aggressive cancer treatment (e.g., tumor resection and/or administration of therapeutic agent).

In various embodiments, the patient enrichment process using the risk predictions for a plurality of subjects generates an enriched cohort of patients that are more likely to develop cancer in comparison to a randomly generated patient cohort. In various embodiments, the patient enrichment process generates an enriched cohort of patients that experiences at least a 1.5-fold increase in cumulative cancer incidence in comparison to a randomly generated patient cohort. In various embodiments, the patient enrichment process generates an enriched cohort of patients that experiences at least a 1.6-fold increase, at least a 1.7-fold increase, at least a 1.8-fold increase, at least a 1.9-fold increase, at least a 2-fold increase, at least a 3-fold increase, at least a 4-fold increase, at least a 5-fold increase, at least a 6-fold increase, at least a 7-fold increase, at least a 8-fold increase, at least a 9-fold increase, at least a 10-fold increase, at least a 11-fold increase, at least a 12-fold increase, at least a 13-fold increase, at least a 14-fold increase, at least a 15-fold increase, at least a 16-fold increase, at least a 17-fold increase, at least a 18-fold increase, at least a 19-fold increase, at least a 20-fold increase, at least a 21-fold increase, at least a 22-fold increase, at least a 23-fold increase, at least a 24-fold increase, at least a 25-fold increase, at least a 26-fold increase, at least a 27-fold increase, at least a 28-fold increase, at least a 29-fold increase, or at least a 30-fold increase in cumulative cancer incidence in comparison to a randomly generated patient cohort.

V. Example Risk Prediction Model

Embodiments disclosed herein involve training and deploying risk prediction models for predicting likelihood of cancer for a subject. As described above, risk prediction models are configured to analyze features, such as nodule features or non-nodule features, to generate the predicted likelihood of cancer for the subject. In various embodiments, the nodule features and/or non-nodule features are extracted from single time point images (e.g., t0 image, t1 image, or t2 image). In various embodiments, the nodule features and/or non-nodule features are extracted from images from two or more time points and therefore, include longitudinal features that demonstrate changes in features across the two or more time points. In various embodiments, the nodules features and/or non-nodule features include both features extracted from a single time point images and longitudinal features extracted from images from two or more time points.

In various embodiments, a risk prediction model includes at least 5 features (e.g., nodule features and/or non-nodule features). In various embodiments, a risk prediction model includes at least 10 features (e.g., nodule features and/or non-nodule features). In various embodiments, a risk prediction model includes at least 15 features (e.g., nodule features and/or non-nodule features). In various embodiments, a risk prediction model includes at least 20 features (e.g., nodule features and/or non-nodule features). In various embodiments, a risk prediction model includes at least 25 features (e.g., nodule features and/or non-nodule features). In various embodiments, a risk prediction model includes at least 30 features (e.g., nodule features and/or non-nodule features). In various embodiments, a risk prediction model includes at least 35 features (e.g., nodule features and/or non-nodule features). In various embodiments, a risk prediction model includes at least 40 features (e.g., nodule features and/or non-nodule features). In various embodiments, a risk prediction model includes at least 45 features (e.g., nodule features and/or non-nodule features). In various embodiments, a risk prediction model includes at least 50 features (e.g., nodule features and/or non-nodule features). In various embodiments, a risk prediction model includes at least 60 features (e.g., nodule features and/or non-nodule features). In various embodiments, a risk prediction model includes at least 70 features (e.g., nodule features and/or non-nodule features). In various embodiments, a risk prediction model includes at least 80 features (e.g., nodule features and/or non-nodule features). In various embodiments, a risk prediction model includes at least 90 features (e.g., nodule features and/or non-nodule features). In various embodiments, a risk prediction model includes at least 100 features (e.g., nodule features and/or non-nodule features).

In various embodiments, a risk prediction model is structured such that nodule features and non-nodule features are separately analyzed to generate separate predictions. Then, the risk prediction model aggregates at least the separate predictions to generate the predicted likelihood of cancer for the subject. For example, the risk prediction model can be structured to include a nodule model that analyzes the nodule features and can further include a non-nodule model that analyzes the non-nodule features. Here, the non-nodule model and the nodule model represent first and second submodels of the risk prediction model.

Generally, the nodule model outputs a prediction that is indicative of the likelihood of cancer based on nodule features (e.g., features of a lung nodule, the edge of the lung nodule, and the boundary/peri-nodule area) derived from the subject. The non-nodule model outputs a prediction that is indicative of the likelihood of cancer based solely on non-nodule features derived from the subject. In various embodiments, the predicted outputs of each of the nodule model and the non-nodule model can be used to generate the predicted likelihood of cancer for the subject. For example, each of the nodule model and the non-nodule model can output a score. Thus, the two scores can be combined to generate the predicted likelihood of cancer for the subject.

In various embodiments, prior to analysis of the nodule features, the nodule model may perform an analysis that filters the nodule features to a reduced set of nodule features. For example, if a CT image for a subject includes more than one nodule, the nodule model may perform an analysis that differentiates between nodules that are associated with high risk of cancer and nodules that are associated with low risk of cancer. In various embodiments, the nodule model filters the nodule features such that the reduced set of nodule features includes features corresponding to a single nodule. For example, the single nodule can be the nodule associated with the highest risk of cancer. In various embodiments, the nodule model filters the nodule features such that the final set of nodule features includes features corresponding to the top X nodules that are associated with the highest risk of cancer. In particular embodiments, X is one nodule. In various embodiments, X is two nodules. In various embodiments, X is three nodules, four nodules, five nodules, six nodules, seven nodules, eight nodules, nine nodules, ten nodules, eleven nodules, twelve nodules, thirteen nodules, fourteen nodules, fifteen nodules, sixteen nodules, seventeen nodules, eighteen nodules, nineteen nodules, or twenty nodules. Thus, the nodule model may analyze the reduced set of nodule features corresponding to the top X nodules and determines a predicted output indicative of likelihood of cancer for the subject based on the reduced set of nodule features.

In various embodiments, the outputs of each of the nodule model and the non-nodule model are provided as input to a third submodel, hereafter referred to as an aggregate model. Thus, the aggregate model can predict the likelihood of cancer based on at least the outputs from the nodule model and the non-nodule model. In various embodiments, the aggregate model can further receive, as input, additional information pertaining to the subject to predict the likelihood of cancer for the subject. This additional information can be further informative for determining whether the subject is likely to develop cancer within a time horizon. Examples of additional information pertaining to the subject include proteomics data derived from the subject, environmental factors that the subject may have been exposed to, genetics of the subject, and/or clinical information of the subject (e.g., age, gender, weight, prior medical history, etc.)

In various embodiments, a risk prediction model is structured to analyze both nodule features and non-nodule features together to generate the predicted likelihood of cancer. Thus, in such embodiments, nodule features and non-nodule features are not separately analyzed. Therefore, nodule features and non-nodule features need not be separated from each other when analyzed by the risk prediction model.

Figure 3A:
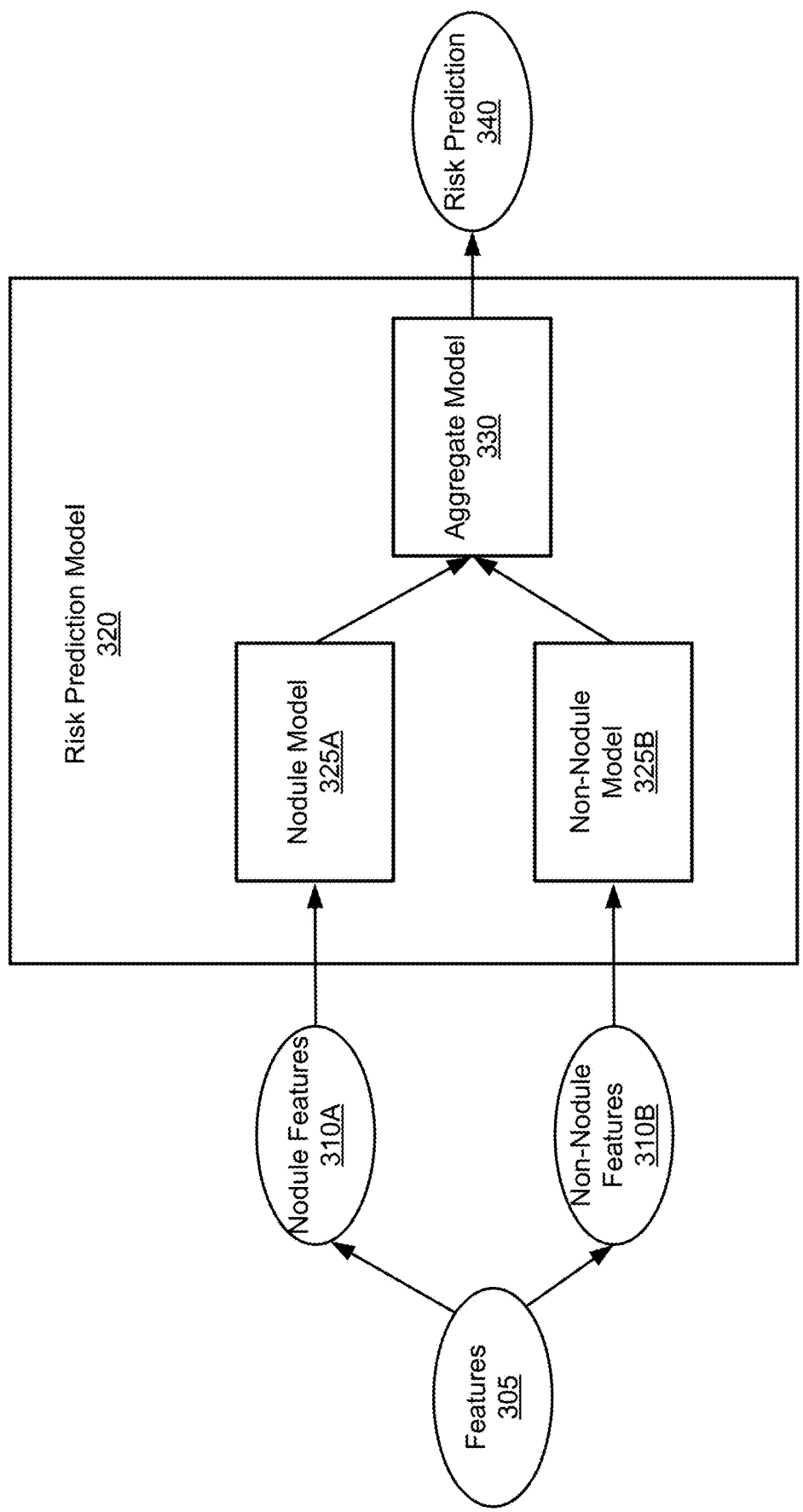
FIG. 3A is an example flow diagram of the implementation of the risk prediction model, in accordance with a first embodiment.

FIG. 3A is an example flow diagram of the implementation of the risk prediction model, in accordance with a first embodiment. As shown in FIG. 3A, the features 305 include nodule features 310A and non-nodule features 310B. In various embodiments, the nodule features 310A are selectively partitioned from the non-nodule features 310B prior to input to the risk prediction model 320. The risk prediction model 320 includes a nodule model 325A and a non-nodule model 325B. Here, the nodule model 325A receives the nodule features 310A as input. The non-nodule model 325B receives the non-nodule features 310B as input. The outputs of each of the nodule model 325A and the non-nodule model 325B are provided as input to the aggregate model 330. The aggregate model 330 generates a risk prediction 340, such as a likelihood of cancer within a time horizon, for the subject.

Figure 3B:
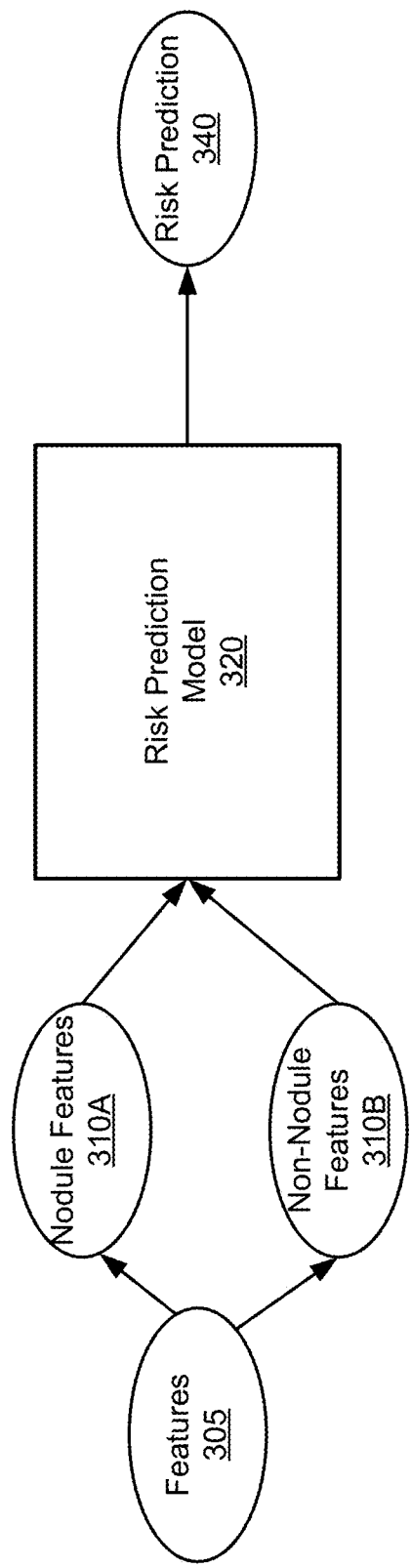
FIG. 3B is an example flow diagram of the implementation of the risk prediction model, in accordance with a second embodiment

FIG. 3B is an example flow diagram of the implementation of the risk prediction model, in accordance with a second embodiment. The features 305 include nodule features 310A and non-nodule features 310B. Here, although FIG. 3B separately shows the nodule features 310A and non-nodule features 310B, in various embodiments, the features 305 themselves are provided as input to the risk prediction model 320. The risk prediction model 320 analyzes the nodule features 310A and the non-nodules features 310B together to generate the risk prediction 340.

VI. Training a Risk Prediction Model

Generally, a risk prediction model is structured such that it analyzes features extracted from an image, such as non-nodule specific features and/or nodule specific features, and predicts a cancer risk for the subject based on the extracted features. In various embodiments, the risk prediction model is any one of a regression model (e.g., linear regression, logistic regression, or polynomial regression), decision tree, random forest, gradient boosted machine learning model, categorical boosted machine learning model, support vector machine, Naïve Bayes model, k-means cluster, or neural network (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, deep bi-directional recurrent networks), or any combination thereof. In particular embodiments, the risk prediction model is a logistic regression model. In particular embodiments, the risk prediction model is a random forest classifier. In particular embodiments, the risk prediction model is a gradient boosting model. In various embodiments, the risk prediction model includes two or more submodels. For example, the risk prediction model can include three submodels, a first submodel that analyzes non-nodule specific features, a second submodel that analyzes nodule specific features, and a third submodel that predicts a risk of cancer by analyzing predictions outputted by the first submodel and the second submodel. In various embodiments, the first submodel, the second submodel, and the third submodel can be, independent of one another, any one of a regression model (e.g., linear regression, logistic regression, or polynomial regression), decision tree, random forest, gradient boosted machine learning model, categorical boosted machine learning model, support vector machine, Naïve Bayes model, k-means cluster, or neural network (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, deep bi-directional recurrent networks), or any combination thereof.

The risk prediction model can be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, and dimensionality reduction techniques such as manifold learning, principal component analysis, factor analysis, autoencoder regularization, and independent component analysis, or combinations thereof. In particular embodiments, the machine learning implemented method is a logistic regression algorithm. In particular embodiments, the machine learning implemented method is a random forest algorithm. In particular embodiments, the machine learning implemented method is a gradient boosting algorithm, such as XGboost. In various embodiments, the risk prediction model is trained using supervised learning algorithms, unsupervised learning algorithms, semi-supervised learning algorithms (e.g., partial supervision), weak supervision, transfer, multi-task learning, or any combination thereof.

In various embodiments, the risk prediction model has one or more parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, node values in a decision tree, and coefficients in a regression model. The model parameters of the risk prediction model are trained (e.g., adjusted) using the training data to improve the predictive capacity of the risk prediction model.

The risk training module 155 trains the risk prediction model using training data. The training data can be stored and/or retrieved from training data store 170. In various embodiments, the training data includes extracted features from training images obtained from training individuals (e.g., individuals that are known to develop or not develop cancer within a period of time). In various embodiments, the training data can be obtained from a split of a dataset. For example, the dataset can undergo a 50:50 training:testing dataset split. In some embodiments, the dataset can undergo a 60:40 training:testing dataset split. In some embodiments, the dataset can undergo a 80:20 training:testing dataset split.

In various embodiments, the training data used for training the imputation model includes reference ground truths that indicate that a training individual developed cancer within a time period (hereafter also referred to as "positive" or "+") or whether the training individual did not develop cancer within the time period (hereafter also referred to as "negative" or "−"). In various embodiments, the reference ground truths in the training data are binary values, such as "1" or "0." For example, a training individual that developed cancer within a time period can be identified in the training data with a value of "1" whereas a training individual that did not develop cancer within the time period can be identified in the training data with a value of "0." In various embodiments, the risk training module 155 trains the risk prediction model using the training data to minimize a loss function such that the risk prediction model can better predict the outcome (e.g., presence or absence of cancer within a time period) based on the input (e.g., extracted features of the training image). In various embodiments, the loss function is constructed for any of a least absolute shrinkage and selection operator (LASSO) regression, Ridge regression, or ElasticNet regression. In various embodiments, the risk prediction model is a random forest model, and is trained to minimize one of Gini impurity or Entropy metrics for feature splitting, thereby enabling the risk prediction model to more accurately predict cancer risk.

In various embodiments, the training data can be obtained and/or derived from a publicly available database. For example, the training data can be obtained and/or derived from the National Lung Screening Trial (NLST). In some embodiments, the training data can be obtained and collected independent of publicly available databases e.g., by capturing images from a plurality of training individuals. Such training data can be a custom dataset.

In various embodiments, a risk prediction model is trained using a specific cohort of training individuals. In various embodiments, the risk prediction model is trained using a cohort of training individuals that do not have lung nodules. In various embodiments, the risk prediction model is trained using a cohort of training individuals that have lung nodules. In various embodiments, the risk prediction model is a Lung-RADS 1 prediction model that is trained using a cohort of training individuals that are previously classified in Lung-RADS 1. In various embodiments, the risk prediction model is a Lung-RADS 2 prediction model that is trained using a cohort of training individuals that are previously classified in any one of Lung-RADS 1-2. In various embodiments, the risk prediction model is a Lung-RADS 1-3 prediction model that is trained using a cohort of training individuals that are previously classified in any one of Lung-RADS 1-3. In various embodiments, the risk prediction model is a Lung-RADS 1-4A prediction model that is trained using a cohort of training individuals that are previously classified in any one of Lung-RADS 1-4A. In various embodiments, the risk prediction model is a Lung-RADS 1-4B prediction model that is trained using a cohort of training individuals that are previously classified in any one of Lung-RADS 1-4B. In various embodiments, the risk prediction model is a Lung-RADS 1-4X prediction model that is trained using a cohort of training individuals that are previously classified in any one of Lung-RADS 1-4X. In various embodiments, the risk prediction model is a Lung-RADS 2-4X prediction model that is trained using a cohort of training individuals that are previously classified in any one of Lung-RADS 2-4X. In various embodiments, the risk prediction model is a Lung-RADS 2-4B prediction model that is trained using a cohort of training individuals that are previously classified in any one of Lung-RADS 2-4B. In various embodiments, the risk prediction model is a Lung-RADS 3-4X prediction model that is trained using a cohort of training individuals that are previously classified in any one of Lung-RADS 3-4X. In various embodiments, the risk prediction model is a Lung-RADS 3-4B prediction model that is trained using a cohort of training individuals that are previously classified in any one of Lung-RADS 3-4B.

In various embodiments, for each of any of the Lung-RADS 1 prediction model, Lung-RADS 1-2 prediction model, Lung-RADS 1-3 prediction model, Lung-RADS 1-4A prediction model, Lung-RADS 1-4B prediction model, or Lung-RADS 1-4X prediction model, the risk prediction model is trained using a training cohort of training individuals, where a majority (e.g., greater than 50%) of training individuals in the training cohort were previously classified as Lung-RADS 1. In various embodiments, for each of any of the Lung-RADS 1 prediction model, Lung-RADS 1-2 prediction model, Lung-RADS 1-3 prediction model, Lung-RADS 1-4A prediction model, Lung-RADS 1-4B prediction model, or Lung-RADS 1-4X prediction model, the risk prediction model is trained using a training cohort of training individuals, where a majority (e.g., greater than 50%) of training individuals in the training cohort were previously classified as Lung-RADS 2. In various embodiments, for each of any of the Lung-RADS 1 prediction model, Lung-RADS 1-2 prediction model, Lung-RADS 1-3 prediction model, Lung-RADS 1-4A prediction model, Lung-RADS 1-4B prediction model, or Lung-RADS 1-4X prediction model, the risk prediction model is trained using a training cohort of training individuals, where a majority (e.g., greater than 50%) of training individuals in the training cohort were previously classified as Lung-RADS 1 or Lung-RADS 2. As shown in Table 1, —90% of individuals likely fall in Lung-RADS 1 or Lung-RADS 2. Therefore, such individuals can be used to train any of the risk prediction models.

In various embodiments, a risk prediction model is a "M" prediction model trained to predict a risk of cancer within an "M" amount of time, such as within at least 0 months, 1 month, 2 months, 3 months, 4 months, 5 months, 6 months, 7 months, 8 months, 9 months, 10 months, 11 months, 1 year, at least 2 years, at least 3 years, at least 4 years, at least 5 years, at least 6 years, at least 7 years, at least 8 years, at least 9 years, at least 10 years, at least 11 years, at least 12 years, at least 13 years, at least 14 years, at least 15 years, at least 16 years, at least 17 years, at least 18 years, at least 19 years, or at least 20 years. Thus, the training data used for training the imputation model includes reference ground truths that indicate that a training individual developed cancer within "M" years.

In various embodiments, a risk prediction model 1) is trained using a specific cohort of training individuals and 2) is trained to predict a risk of cancer within "M" amount of time. As described above, the cohort of training individuals may be previously classified within a range of Lung-RADS scores (e.g., Lung-RADS X-Y). Thus, a risk prediction model may be a M year, Lung-RADS X-Y prediction model that 1) is trained using a cohort of training individuals classified in Lung-RADS X-Y and 2) is trained to predict a risk of cancer with "M" years.

In various embodiments, a risk prediction model includes both non-nodule specific features and nodule specific features. Therefore, in training the risk prediction model, the risk prediction model analyzes both non-nodule specific features and nodule specific features extracted from a training image and attempts to generate a prediction that minimizes a loss function. Generally, features of the risk prediction model have importance values that reflect how heavily each feature influences the prediction generated by the risk prediction model. For example, a higher importance value for a feature indicates that the feature more heavily influences the prediction generated by the risk prediction model in comparison to a different feature with a lower importance value.

In various embodiments, the nodule specific features of the risk prediction model more heavily influence the prediction of risk of cancer in comparison to the non-nodule specific features. For example, the nodule specific features of the risk prediction model have higher feature importance values than the non-nodule specific features of the risk prediction model. Generally, nodule specific features have higher importance values for risk prediction models that are trained to predict risk of cancer within shorter time periods (e.g., 1 year as opposed to 3 years or 5 years). Additionally, nodule specific features have higher importance values for risk prediction models that are trained using higher risk lung cancer patients (e.g., patients that are classified as Lung-RADS 4A or Lung-RADS 4B).

In various embodiments, the feature with the highest importance value of the risk prediction model is a nodule specific feature. In various embodiments, the top 2 features with the highest importance value of the risk prediction model are nodule specific features. In various embodiments, the top 3 features with the highest importance value of the risk prediction model are nodule specific features. In various embodiments, the top 4 features with the highest importance value of the risk prediction model are nodule specific features. In various embodiments, the top 5, 6, 7, 8, 9, or 10 features with the highest importance value of the risk prediction model are nodule specific features.

In various embodiments, the non-nodule specific features of the risk prediction model more heavily influence the prediction of risk of cancer in comparison to the nodule specific features. For example, the non-nodule specific features of the risk prediction model have higher feature importance values than the nodule specific features of the risk prediction model. Generally, non-nodule specific features have higher importance values for risk prediction models that are trained to predict risk of cancer within longer time periods (e.g., 3 or 5 years as opposed to 1 year). Additionally, non-nodule specific features have higher importance values for risk prediction models that are trained using patients that are at lower risk of lung cancer (e.g., patients that are classified as Lung-RADS 2 or 3) or patients that do not yet have a nodule (e.g., Lung-RADS 1).

In various embodiments, the feature with the highest importance value of the risk prediction model is a non-nodule specific feature. In various embodiments, the top 2 features with the highest importance value of the risk prediction model are non-nodule specific features. In various embodiments, the top 3 features with the highest importance value of the risk prediction model are non-nodule specific features. In various embodiments, the top 4 features with the highest importance value of the risk prediction model are non-nodule specific features. In various embodiments, the top 5, 6, 7, 8, 9, or 10 features with the highest importance value of the risk prediction model are non-nodule specific features.

In various embodiments, the risk prediction model includes different submodels that separately analyze different features. For example, as described above in reference to FIG. 3A, a risk prediction model can include a first submodel (e.g., non-nodule model) that analyzes the non-nodule specific features and/or longitudinal non-nodule specific features. The risk prediction model can include a second submodel (e.g., nodule model) that analyzes the nodule specific features and/or longitudinal nodule specific features. Referring first to the first submodel (e.g., non-nodule model), in various embodiments, one or more of the top 10 features with the highest feature importance values are longitudinal non-nodule specific features. In various embodiments, two or more of the top 10 features with the highest feature importance values are longitudinal non-nodule specific features. In various embodiments, three or more, four or more, five or more, six or more, seven or more, eight or more, nine or more features of the top 10 features with the highest feature importance values are longitudinal non-nodule specific features. In particular embodiments, four features of the top 10 features with the highest feature importance values are longitudinal non-nodule specific features. In particular embodiments, five features of the top 10 features with the highest feature importance values are longitudinal non-nodule specific features.

In various embodiments, one or more of the top 10 features with the highest feature importance values are non-nodule specific features. In various embodiments, two or more of the top 10 features with the highest feature importance values are non-nodule specific features. In various embodiments, three or more, four or more, five or more, six or more, seven or more, eight or more, nine or more features of the top 10 features with the highest feature importance values are non-nodule specific features. In particular embodiments, four features of the top 10 features with the highest feature importance values are non-nodule specific features. In particular embodiments, five features of the top 10 features with the highest feature importance values are non-nodule specific features. In particular embodiments, six features of the top 10 features with the highest feature importance values are non-nodule specific features.

Referring next to the second submodel (e.g., nodule model), in various embodiments, one or more of the top 10 features with the highest feature importance values are longitudinal nodule specific features. In various embodiments, two or more of the top 10 features with the highest feature importance values are longitudinal nodule specific features. In various embodiments, three or more, four or more, five or more, six or more, seven or more, eight or more, nine or more features of the top 10 features with the highest feature importance values are longitudinal nodule specific features. In particular embodiments, four features of the top 10 features with the highest feature importance values are longitudinal nodule specific features. In particular embodiments, five features of the top 10 features with the highest feature importance values are longitudinal nodule specific features.

In various embodiments, one or more of the top 10 features with the highest feature importance values are nodule specific features. In various embodiments, two or more of the top 10 features with the highest feature importance values are nodule specific features. In various embodiments, three or more, four or more, five or more, six or more, seven or more, eight or more, nine or more features of the top 10 features with the highest feature importance values are nodule specific features. In particular embodiments, four features of the top 10 features with the highest feature importance values are nodule specific features. In particular embodiments, five features of the top 10 features with the highest feature importance values are nodule specific features. In particular embodiments, six features of the top 10 features with the highest feature importance values are nodule specific features.

In various embodiments, a risk prediction model including non-nodule specific features that more heavily influence the prediction of future risk of cancer in comparison to the nodule specific features is a M year risk prediction model (e.g., predicts risk of developing cancer within M years), where M is not equal to 1 year. In various embodiments, M is greater than or equal to 2 years. For example, M can be 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. As a specific example, the risk prediction model is a 3 year risk prediction model that predicts risk of developing cancer within 3 years. As another specific example, the risk prediction model is a 5 year risk prediction model that predicts risk of developing cancer within 5 years.

In various embodiments, a risk prediction model including non-nodule specific features that more heavily influence the prediction of risk of cancer in comparison to the nodule specific features is a risk prediction model trained on training images that do not include lung nodules. In various embodiments, such a risk prediction model can be trained on training images derived from individuals classified in Lung-RADS 1. In various embodiments, such a risk prediction model can be trained on training images derived from individuals classified in Lung-RADS 2. In various embodiments, such a risk prediction model can be trained on training images derived from individuals classified in Lung-RADS 3. In various embodiments, such a risk prediction model can be trained on training images derived from individuals classified in Lung-RADS 1, Lung-RADS 2, Lung-RADS 3, or any combination thereof. In various embodiments, such a risk prediction model is a Lung-RADS 1 prediction model, a Lung-RADS 1-2 prediction model, or a Lung-RADS 1-3 prediction model.

In particular embodiments, such a risk prediction model (e.g., a risk prediction model where non-nodule specific features of the risk prediction model have higher feature importance values than the nodule specific features of the risk prediction model) is a 1 year, Lung-RADS 1-4B prediction model. In particular embodiments, such a risk prediction model (e.g., a risk prediction model where non-nodule specific features of the risk prediction model have higher feature importance values than the nodule specific features of the risk prediction model) is a 3 year, Lung-RADS 1-4B prediction model. In particular embodiments, such a risk prediction model (e.g., a risk prediction model where non-nodule specific features of the risk prediction model have higher feature importance values than the nodule specific features of the risk prediction model) is a 5 year, Lung-RADS 1-4B prediction model.

In particular embodiments, such a risk prediction model (e.g., a risk prediction model where non-nodule specific features of the risk prediction model have higher feature importance values than the nodule specific features of the risk prediction model) is a 5 year, Lung-RADS 1-4A prediction model. In particular embodiments, such a risk prediction model (e.g., a risk prediction model where non-nodule specific features of the risk prediction model have higher feature importance values than the nodule specific features of the risk prediction model) is a 1 year, Lung-RADS 1-3 prediction model. In particular embodiments, such a risk prediction model (e.g., a risk prediction model where non-nodule specific features of the risk prediction model have higher feature importance values than the nodule specific features of the risk prediction model) is a 3 year, Lung-RADS 1-3 prediction model. In particular embodiments, such a risk prediction model (e.g., a risk prediction model where non-nodule specific features of the risk prediction model have higher feature importance values than the nodule specific features of the risk prediction model) is a 5 year, Lung-RADS 1-3 prediction model.

In particular embodiments, such a risk prediction model (e.g., a risk prediction model where non-nodule specific features of the risk prediction model have higher feature importance values than the nodule specific features of the risk prediction model) is a 1 year, Lung-RADS 1-2 prediction model. In particular embodiments, such a risk prediction model (e.g., a risk prediction model where non-nodule specific features of the risk prediction model have higher feature importance values than the nodule specific features of the risk prediction model) is a 3 year, Lung-RADS 1-2 prediction model. In particular embodiments, such a risk prediction model (e.g., a risk prediction model where non-nodule specific features of the risk prediction model have higher feature importance values than the nodule specific features of the risk prediction model) is a 5 year, Lung-RADS 1-2 prediction model.

In particular embodiments, such a risk prediction model (e.g., a risk prediction model where non-nodule specific features of the risk prediction model have higher feature importance values than the nodule specific features of the risk prediction model) is a 1 year, Lung-RADS 1 prediction model. In particular embodiments, such a risk prediction model (e.g., a risk prediction model where non-nodule specific features of the risk prediction model have higher feature importance values than the nodule specific features of the risk prediction model) is a 3 year, Lung-RADS 1 prediction model. In particular embodiments, such a risk prediction model (e.g., a risk prediction model where non-nodule specific features of the risk prediction model have higher feature importance values than the nodule specific features of the risk prediction model) is a 5 year, Lung-RADS 1 prediction model.

In various embodiments, the trained risk prediction model includes a set of trained parameters such that when the risk prediction model is deployed, the set of trained parameters are used to modify values of non-nodule specific features and nodule specific features of an image to generate a prediction of risk of cancer for a subject. Thus, the set of trained parameters of the trained risk prediction model are set during the training phase. For example, the set of trained parameters are set such that the non-nodule specific features more heavily influence the risk prediction than the nodule specific features. As another example, the set of trained parameters are set such that the nodule specific features more heavily influence the risk prediction than the non-nodule specific features.

For example, if the risk prediction model is a neural network, one or more nodes of the neural network that correspond to non-nodule specific features are assigned greater weights (e.g., parameters) than one or more nodes of the neural network that correspond to nodule specific features. As another example, if the risk prediction model is a random forest model that weighs non-nodule specific features more heavily than nodule specific features.

In various embodiments, the risk prediction models may also be trained to predict a location of that cancer. In various embodiments, training images are divided into different regions and therefore, the training of the risk predictions models are performed according to the different regions. Example different regions can include the upper, middle, and lower third of the lungs by volume or separate lobes of the lungs. It will be understood by those of skill in the art that the lung may be divided into any number of regions having any number of configurations. Enabling risk prediction models to predict locations of cancers can guide the selection of interventions, such as regional diagnostic evaluations and therapeutic intervention using inhaled and bronchoscopically administered drugs and devices.

In various embodiments, risk prediction models disclosed herein achieve a performance metric. Example performance metrics include an area under the curve (AUC) of a receiver operating curve, a positive predictive value, and/or a negative predictive value. In various embodiments, risk prediction models disclosed herein exhibit an AUC value of at least 0.5. In various embodiments, risk prediction models disclosed herein exhibit an AUC value of at least 0.6. In various embodiments, risk prediction models disclosed herein exhibit an AUC value of at least 0.7. In various embodiments, risk prediction models disclosed herein exhibit an AUC value of at least 0.8. In various embodiments, risk prediction models disclosed herein exhibit an AUC value of at least 0.9. In various embodiments, risk prediction models disclosed herein exhibit an AUC value of at least 0.95. In various embodiments, risk prediction models disclosed herein exhibit an AUC value of at least 0.99. In various embodiments, risk prediction models disclosed herein exhibit an AUC value of at least 0.51, at least 0.52, at least 0.53, at least 0.54, at least 0.55, at least 0.56, at least 0.57, at least 0.58, at least 0.59, at least 0.60, at least 0.61, at least 0.62, at least 0.63, at least 0.64, at least 0.65, at least 0.66, at least 0.67, at least 0.68, at least 0.69, at least 0.70, at least 0.71, at least 0.72, at least 0.73, at least 0.74, at least 0.75, at least 0.76, at least 0.77, at least 0.78, at least 0.79, at least 0.80, at least 0.81, at least 0.82, at least 0.83, at least 0.84, at least 0.85, at least 0.86, at least 0.87, at least 0.88, at least 0.89, at least 0.90, at least 0.91, at least 0.92, at least 0.93, at least 0.94, at least 0.95, at least 0.96, at least 0.97, at least 0.98, or at least 0.99.

VII. Example Method for Predicting Risk of Cancer

Figure 4A:
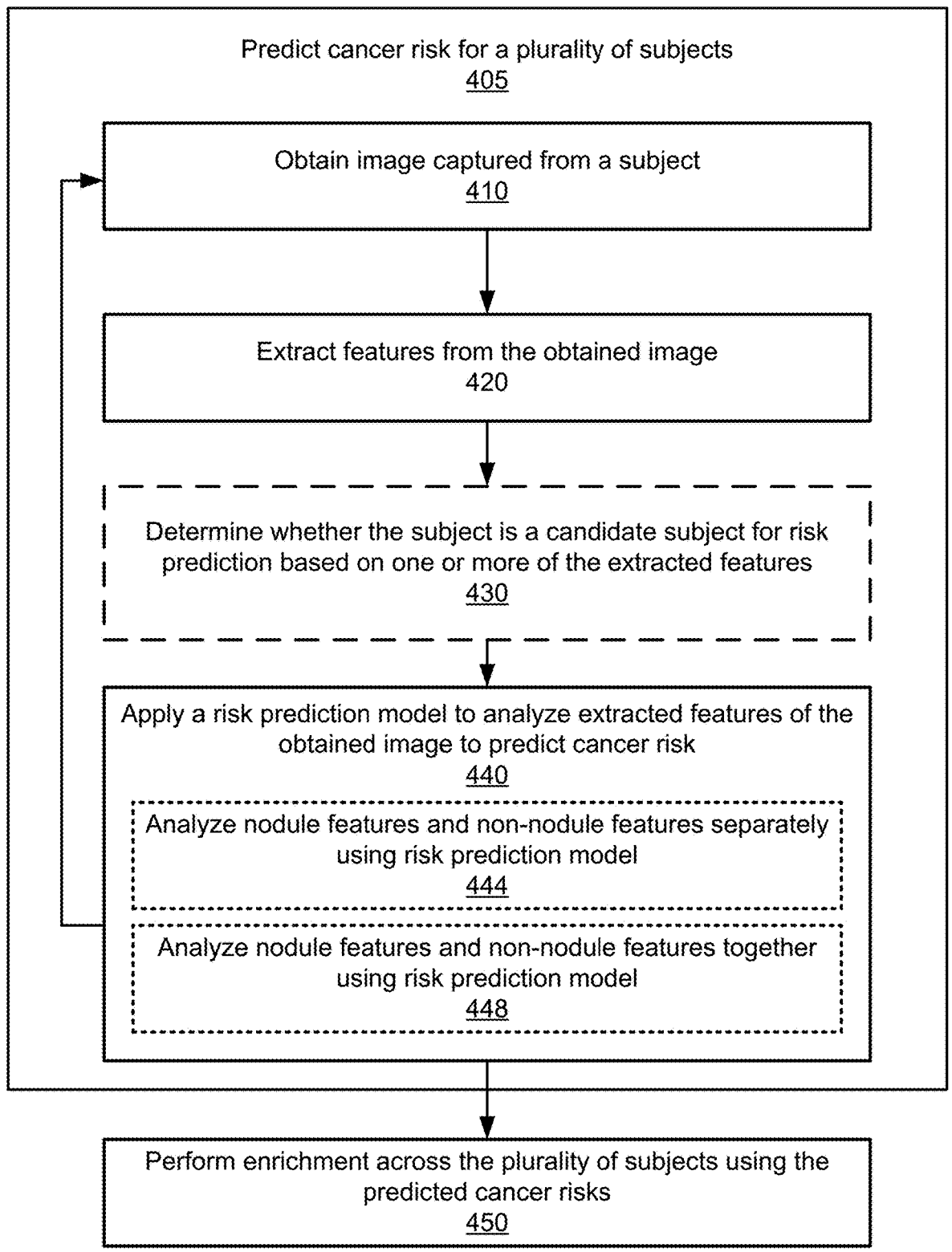
FIG. 4A is an example flow process for determining a risk of cancer (e.g., a future risk of cancer) for a subject for uses such as patient enrichment, in accordance with an embodiment.

FIG. 4A is an example flow process for determining a risk of cancer for a subject for uses such as patient enrichment, in accordance with an embodiment. Step 405 involves predicting lung cancer risk for a plurality of subjects. Step 405 includes steps 410, 420, 430, and 440 which can be repeatedly performed for different subjects in the plurality of subjects.

At step 410, an image is captured from a subject. In various embodiments, the image is a CT scan (e.g., a whole body CT scan, a CT scan including the lung, a chest CT scan, or a lung CT scan) captured from the subject.

At step 420, features are extracted from the image. In various embodiments, the features include one or both of non-nodule specific features and nodule specific features.

Step 430 is an optional step that involves determining whether the subject is a candidate subject for risk prediction based on one or more of the extracted features. In various embodiments, step 430 involves analyzing nodule specific features to determine that the subject is a candidate subject. For example, step 430 can involve analyzing nodule specific features to determine that the subject does not have a lung nodule or does not have lung cancer and therefore, is eligible to undergo risk of cancer analysis.

Step 440 involves applying a risk prediction model to analyze the extracted features of the obtained image to predict cancer risk. In various embodiments, the risk prediction model analyzes both non-nodule specific features and nodule specific features. As shown in FIG. 4A, the risk prediction model can analyze nodule features and non-nodule features in one of two ways. First, as shown in step 444, the risk prediction model can analyze nodule features and non-nodule features separately (e.g., as described above in reference to FIG. 3A). Second, as shown in step 448, the risk prediction model can analyze nodule features and non-nodule features together (e.g., as described above in reference to FIG. 3B).

Step 450 involves performing enrichment across the plurality of subjects using the predicted cancer risks. Here, subjects that are predicted to develop cancer within a period of time, as indicated by their predicted cancer risk, can be included in one or more a patient cohort for enrollment in a clinical trial. Altogether, this enables the enrollment of reduced numbers of individuals in clinical trials.

Figure 4B:
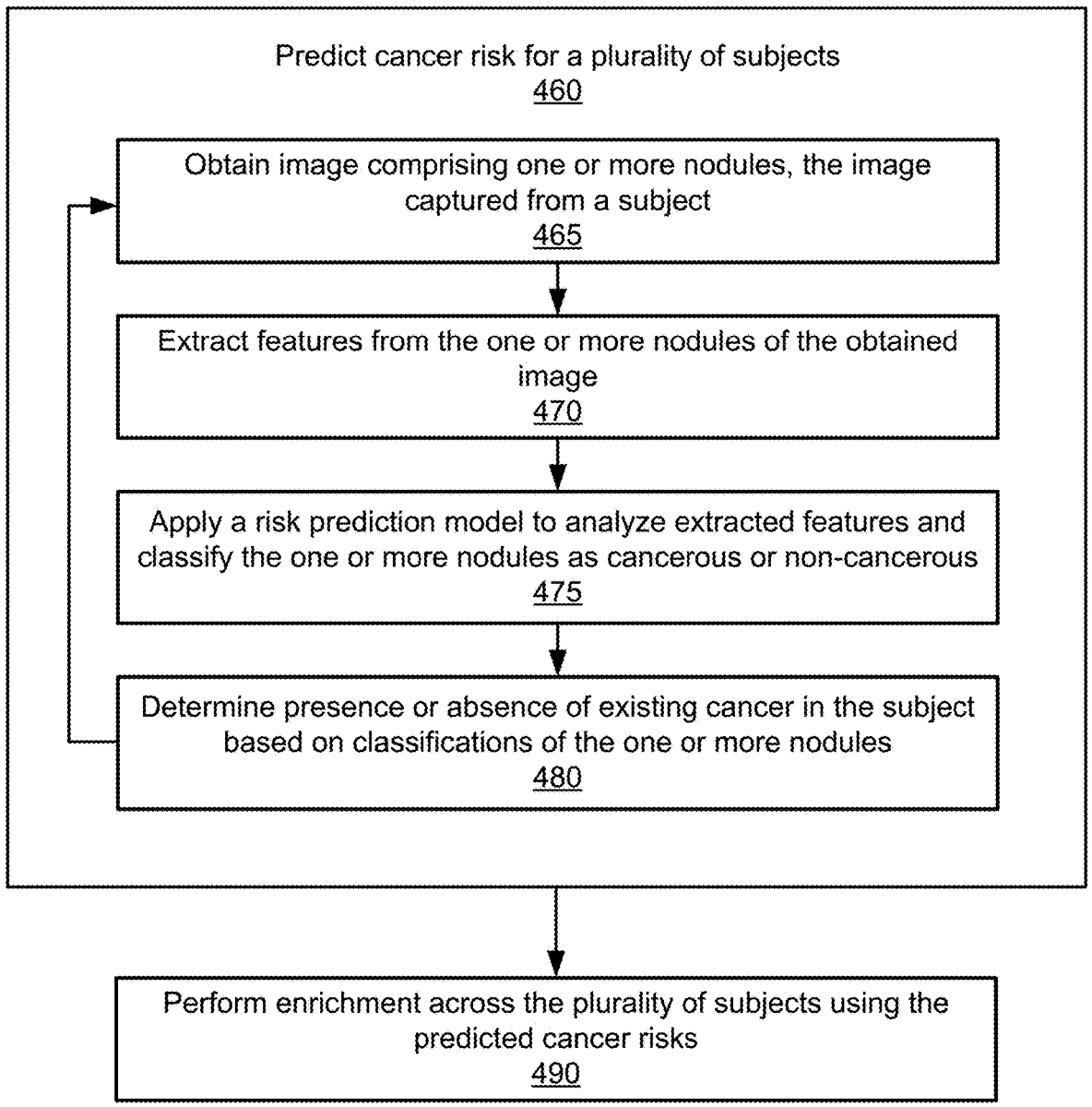
FIG. 4B is an example flow process for determining a risk of cancer (e.g., a risk for existing or prevalent cancer) for a subject, in accordance with a second embodiment.

Reference is now made to FIG. 4B, which is an example flow process for determining a risk of cancer (e.g., a risk for existing or prevalent cancer) for a subject, in accordance with a second embodiment. Step 460 involves predicting cancer risk for a plurality of subjects. Step 460 includes steps 465, 470, 475, and 480 which can be repeatedly performed for different subjects in the plurality of subjects.

Step 465 involves obtaining an image captured from a subject. In various embodiments, the image is a CT scan (e.g., a whole body CT scan, a CT scan including the lung, a chest CT scan, or a lung CT scan) captured from the subject. The image can include one or more nodules present in the subject. Here, the one or more nodules may be suspected of being cancerous nodules, which is indicative of cancer (e.g., lung cancer).

Step 470 involves extracting features from the one or more nodules. As described herein extracted features may include nodule-specific features. Here, individual sets of features may be extracted for each individual nodule.

Step 475 involves applying one or more risk prediction models to analyze the extracted features. The one or more risk prediction models generate predictions that are informative for classifying the one or more nodules as cancerous or non-cancerous.

Step 480 involves determining presence or absence of existing cancer in the subject based on the classifications of the one or more nodules. For example, if at least nodule is classified as cancerous, then step 480 involves determining that the subject has a presence of existing cancer. In various embodiments, step 480 involves determining that the subject has a presence of existing cancer if at least two nodules are classified as cancerous. In various embodiments, step 480 involves determining that the subject has a presence of existing cancer if at least three, at least four, or at least five nodules are classified as cancerous.

In various embodiments, step 480 involves determining that the subject has an absence of existing cancer if less than one nodule is classified as cancerous. In various embodiments, step 480 involves determining that the subject has an absence of existing cancer if zero nodules are classified as cancerous.

Step 490 involves performing enrichment across the plurality of subjects using the predicted cancer risks. For example, subjects that are predicted to have presence of existing cancer can be included in one or more a patient cohort for enrollment in a clinical trial. Altogether, this enables the enrollment of reduced numbers of individuals in clinical trials.

VIII. Cancers

Methods described herein involve implementing risk prediction models for predicting risk of cancer. In various embodiments, the cancer in the subject can include one or more of: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, stomach cancer, thyroid cancer, head and neck carcinoma, large bowel cancer, hematopoietic cancer, testicular cancer, colon and/or rectal cancer, uterine cancer, or prostatic cancer. In some embodiments, the cancer in the subject can be a metastatic cancer, including any one of bladder cancer, breast cancer, colon cancer, kidney cancer, lung cancer, melanoma, ovarian cancer, pancreatic cancer, prostatic cancer, rectal cancer, stomach cancer, thyroid cancer, or uterine cancer. In particular embodiments, the cancer is a lung cancer. In particular embodiments, the cancer is a type of lung cancer, including any one of small cell lung cancer, non-small cell lung cancer, non-small cell carcinoma, adenocarcinoma, squamous cell cancer, large cell carcinoma, small cell carcinoma, combined small cell carcinoma, neuroendocrine tumor, lung sarcoma, lung lymphoma, bronchial carcinoids.

In various embodiments, risk prediction models described herein predict a risk of a presence of cancer, such as a lung cancer. In other words, risk prediction models predict for a risk of a presence or absence of cancer, such as a lung cancer. In various embodiments, risk prediction models described herein predict a risk of a subtype of lung cancer, including any one of small cell lung cancer, non-small cell lung cancer, non-small cell carcinoma, adenocarcinoma, squamous cell cancer, large cell carcinoma, small cell carcinoma, combined small cell carcinoma, neuroendocrine tumor, lung sarcoma, lung lymphoma, bronchial carcinoids. In other words, risk prediction models classify a subject as likely to develop a particular subtype of lung cancer within a time period (e.g., 1, 3, or 5 years). In particular embodiments, risk prediction models predict a risk of non-small cell lung cancer or small cell lung cancer.

IX. Interventions

Embodiments described herein involve the implementing risk prediction models for predicting risk of cancer. In various embodiments, an intervention is provided to a subject based on the risk of cancer prediction. In various embodiments, the intervention can be any one of: application of a diagnostic, application of a prophylactic therapeutic agent, or a subsequent action. Example subsequent actions can include a subsequent testing of the subject to confirm whether the subject develops cancer. Subsequent testing can include any of a subsequent biopsy (e.g., cancer biopsy or lymph node biopsy) or subsequent image scanning (e.g., CT scanning, PET scanning, MRI scanning, ultrasound imaging, or X-ray imaging). In various embodiments, subsequent testing of the subject can during at a next scheduled visit or at a pre-determined amount of time (e.g., 0 months, 1 month, 2 months, 3 months, 4 months, 5 months, 6 months, 7 months, 8 months, 9 months, 10 months, 11 months, 12 months, 18 months, or 24 months) after predicting the risk of cancer. In various embodiments, additional subsequent actions can include subsequent actions to treat a cancer that has developed in the subject, such as tumor resection, bronchoscopic diagnosis, selection and/or administration of therapeutic(s), selection/administration of pharmaceutical composition, or any combination thereof.

In various embodiments, a therapeutic agent can be selected and/or administered to the subject based on the predicted risk of cancer. The selected therapeutic agent is likely to delay or prevent the development of the cancer, such as lung cancer. Exemplary therapeutic agents include chemotherapies, energy therapies (e.g., external beam, microwave, radiofrequency ablation, brachytherapy, electroporation, cryoablation, photothermal ablation, laser therapy, photodynamic therapy, electrocauterization, chemoembolization, high intensity focused ultrasound, low intensity focused ultrasound), antigen-specific monoclonal antibodies, anti-inflammatories, oncolytic viral therapies, or immunotherapies. In various embodiments, the selected therapeutic agent is an energy therapy and the amount (e.g., dose and duration) of the energy applied can be tailored to achieve a desired therapeutic effect. In various embodiments the therapeutic agent is a small molecule or biologic, e.g. a cytokine, antibody, soluble cytokine receptor, anti-sense oligonucleotide, siRNA, etc. Such biologic agents encompass muteins and derivatives of the biological agent, which derivatives can include, for example, fusion proteins, PEGylated derivatives, cholesterol conjugated derivatives, and the like as known in the art. Also included are antagonists of cytokines and cytokine receptors, e.g. traps and monoclonal antagonists. Also included are biosimilar or bioequivalent drugs to the active agents set forth herein.

Therapeutic agents for lung cancer can include chemotherapeutics such as docetaxel, cisplatin, carboplatin, gemcitabine, Nab-paclitaxel, paclitaxel, pemetrexed, gefitinib, erlotinib, brigatinib (Alunbrig®), capmatinib (Tabrecta®), selpercatinib (Retevmo®), entrectinib (Rozlytrek®), lorlatinib (Lorbrena®), larotrectinib (Vitrakvi®), dacomitinib (Vizimpro®), and vinorelbine. Therapeutic agents for lung cancer can include antibody therapies such as durvalumab (Imfinzi®), nivolumab (Opdivo®), pembrolizumab (Keytruda®), atezolizumab (Tecentriq®), canakinumab, and ramucirumab.

In various embodiments, one or more of the therapeutic agents described can be combined as a combination therapy for treating the subject.

In various embodiments, a pharmaceutical composition can be selected and/or administered to the subject based on the subject level risk of metastatic cancer, the selected therapeutic agent likely to exhibit efficacy against the cancer. A pharmaceutical composition administered to an individual includes an active agent such as the therapeutic agent described above. The active ingredient is present in a therapeutically effective amount, i.e., an amount sufficient when administered to treat a disease or medical condition mediated thereby. The compositions can also include various other agents to enhance delivery and efficacy, e.g. to enhance delivery and stability of the active ingredients. Thus, for example, the compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

The pharmaceutical compositions or therapeutic agents described herein can be administered in a variety of different ways. Examples include administering a composition containing a pharmaceutically acceptable carrier via oral, intranasal, intramodular, intralesional, rectal, topical, intraperitoneal, intravenous, intramuscular, subcutaneous, subdermal, transdermal, intrathecal, endobronchial, transthoracic, or intracranial method.

In various embodiments, a clinical response can be provided to the subject based on the predicted risk of cancer generated for the subject by implementing risk prediction models. In various embodiments, a clinical response can include providing counseling to modify a behavior of the subject (e.g., counsel the patient about smoking cessation to reduce risk), initiating of an inhaled/topical, intravenous or enteral (by mouth) therapeutic that could delay/prevent malignant transformation, slow tumor growth or even prevent spread of disease (metastasis), establishing an adaptive screening schedule for risk similar to what is done with colonoscopy for polyps (e.g., individuals predicted to be higher risk for lung cancer should have more frequent follow up and imaging), or performing or scheduling to be performed an additional risk prediction test to confirm the predicted risk of lung cancer (e.g., persons deemed to be higher risk for lung cancer may also then undergo additional testing to either confirm that risk or narrow the cancer type the person is at greatest risk for. In various embodiments, the additional risk prediction test could include blood based biomarkers (to look for non-specific inflammation which is a known risk for lung cancer), metabolomics/proteomics/gene expression/genetic sequencing. The person could also have additional sampling of tissue (nasal epithelium, bronchial epithelium, etc) to look at changes in gene expression in the respiratory tract.)

X. Computer Implementation

The methods, including the methods of implementing risk prediction models for predicting risk of cancer, are, in some embodiments, performed on one or more computers.

For example, the building and deployment of a risk prediction model can be implemented in hardware or software, or a combination of both. In one embodiment, a machine-readable storage medium is provided, the medium comprising a data storage material encoded with machine readable data which, when using a machine programmed with instructions for using said data, is capable of executing the training or deployment of risk prediction models and/or displaying any of the datasets or results (e.g., risk of cancer predictions for subjects) described herein. The invention can be implemented in computer programs executing on programmable computers, comprising a processor, a data storage system (including volatile and non-volatile memory and/or storage elements), a graphics adapter, a pointing device, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high-level procedural or object-oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains a signature pattern information. Databases can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

In some embodiments, the methods, including the methods for predicting a risk of cancer by implementing risk prediction models, are performed on one or more computers in a distributed computing system environment (e.g., in a cloud computing environment). In this description, "cloud computing" is defined as a model for enabling on-demand network access to a shared set of configurable computing resources. Cloud computing can be employed to offer on-demand access to the shared set of configurable computing resources. The shared set of configurable computing resources can be rapidly provisioned via virtualization and released with low management effort or service provider interaction, and then scaled accordingly. A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 5:
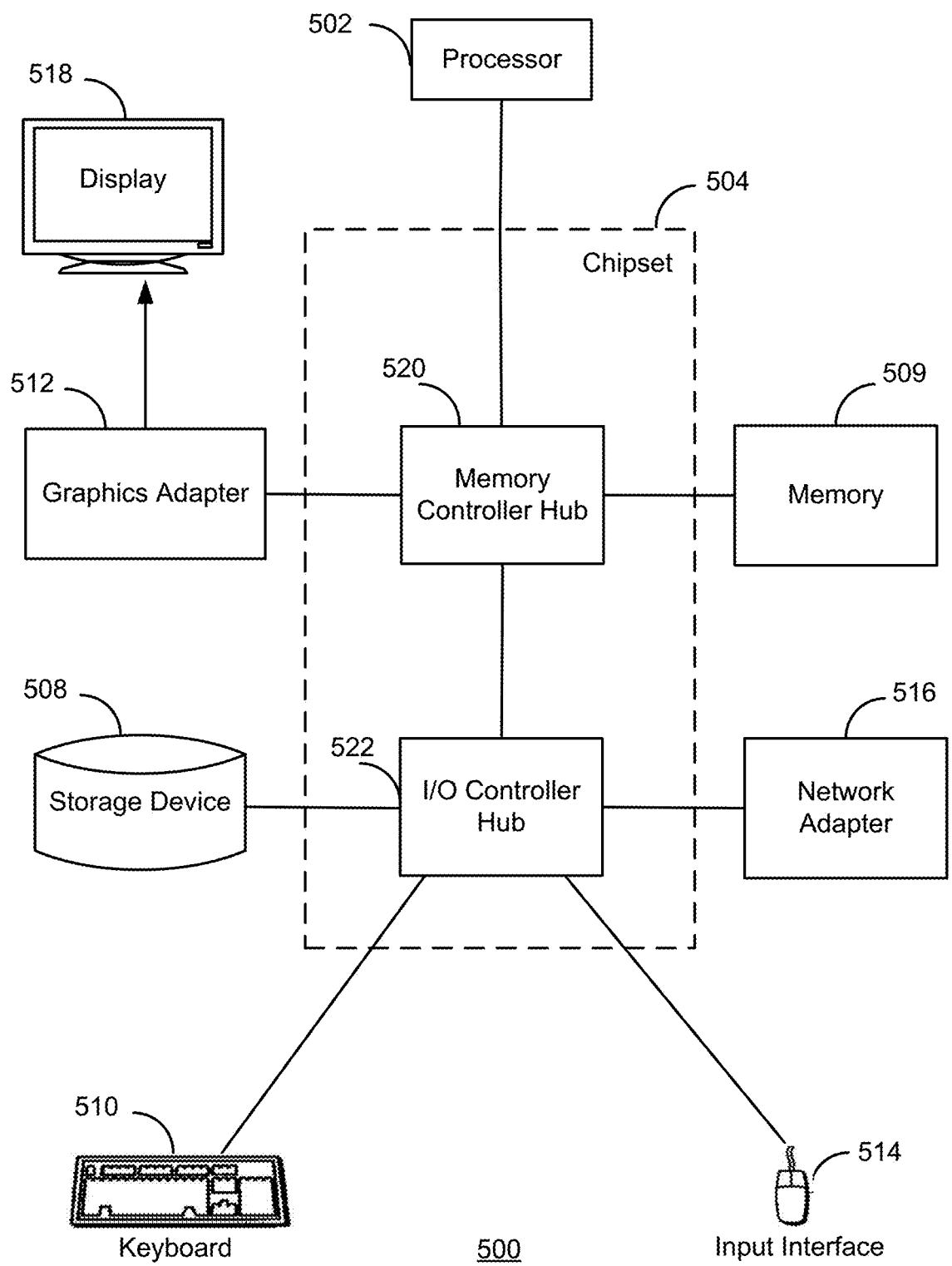
FIG. 5 illustrates an example computer for implementing the entities shown in FIGS. 1A, 1B, 2A, 2B, 3A, 3B, 4A and 4B.

FIG. 5 illustrates an example computer for implementing the entities shown in FIGS. 1A, 1B, 2A, 2B, 3A, 3B, 4A, and 4B. The computer 500 includes at least one processor 502 coupled to a chipset 504. The chipset 504 includes a memory controller hub 520 and an input/output (I/O) controller hub 522. A memory 506 and a graphics adapter 512 are coupled to the memory controller hub 520, and a display 518 is coupled to the graphics adapter 512. A storage device 508, an input device 514, and network adapter 516 are coupled to the I/O controller hub 522. Other embodiments of the computer 500 have different architectures.

The storage device 508 is a non-transitory computer-readable storage medium such as a hard drive, compact disk read-only memory (CD-ROM), DVD, or a solid-state memory device. The memory 506 holds instructions and data used by the processor 502. The input interface 514 is a touch-screen interface, a mouse, track ball, or other type of pointing device, a keyboard, or some combination thereof, and is used to input data into the computer 500. In some embodiments, the computer 500 may be configured to receive input (e.g., commands) from the input interface 514 via gestures from the user. The network adapter 516 couples the computer 500 to one or more computer networks.

The graphics adapter 512 displays images and other information on the display 518. In various embodiments, the display 518 is configured such that the user may (e.g., radiologist, oncologist, pulmonologist) may input user selections on the display 518 to, for example, initiate risk prediction for a patient, order any additional exams or procedures and/or set parameters for the risk prediction models. In one embodiment, the display 518 may include a touch interface. In various embodiments, the display 518 can show one or more risk of cancer predictions for a subject. Thus, a user who accesses the display 518 can inform the subject of the risk of cancer that is predicted for the subject. In various embodiments, the display 518 can show information such as the features that most heavily contributed to the risk of cancer prediction for a subject. For example, a subject predicted to have a risk of cancer can be largely due to a percentage of the subject's lung occupied by centrilobular emphysema. Thus, the identification of the feature and/or the value of the feature (e.g., percentage of the subject's lung occupied by centrilobular emphysema) can be shown on the display 518 to a user e.g., clinician user. In various embodiments, the top 1, top 2, top 3, top 4, top 5, top 6, top 7, top 8, top 9, or top 10 features that most heavily contributed to the risk of cancer prediction for the subject can be shown on the display 518. Displaying the top contributing features can provide context to a user e.g., clinician user in understanding the features that resulted in the risk of cancer prediction. Patient profiles, CT images, generated risk assessments and any other relevant information may be stored to the memory so that patient information/results may be accessible at any given time.

The computer 500 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 508, loaded into the memory 506, and executed by the processor 502.

The types of computers 500 used by the entities of FIG. 1A or 1B can vary depending upon the embodiment and the processing power required by the entity. For example, the cancer prediction system 130 can run in a single computer 500 or multiple computers 500 communicating with each other through a network such as in a server farm. The computers 500 can lack some of the components described above, such as graphics adapters 512, and displays 518.

XI. Systems

Further disclosed herein are systems for implementing risk prediction models for predicting risk of cancer. In various embodiments, such a system can include at least the cancer prediction system 130 described above in FIG. 1A. In various embodiments, the cancer prediction system 130 is embodied as a computer system, such as a computer system with example computer 500 described in FIG. 5.

In various embodiments, the system includes an imaging device, such as imaging device 120 described above in FIG. 1A. In various embodiments, the system includes both the cancer prediction system 130 (e.g., a computer system) and an imaging device. In such embodiments, the cancer prediction system 130 can be communicatively coupled with the imaging device 120 to receive images (e.g., CT scans) captured from a subject. The computer system implements, in silico, risk prediction models to analyze the images and to determine a risk of lung cancer for the subject.

EXAMPLES

Below are examples of specific embodiments for carrying out the present invention. The examples are offered for illustrative purposes only and are not intended to limit the scope of the present invention in any way. Efforts have been made to ensure accuracy with respect to numbers used (e.g., amounts, temperatures, etc.), but some experimental error and deviation should be allowed for.

Example 1: Building Risk Prediction Models and Summary of Analysis

Computed tomography (CT) images from the National Lung Cancer Screening Trial (NLST) cohort were analyzed to predict likelihood of cancer in patients across a 3 year future horizon timepoint. The predicted future risk of cancer was used to identify a population of patients enriched for the development of lung cancer.

The National Lung Screening Trial (NLST) was a randomized controlled trial to determine if annual CT scanning instead of annual chest X-rays could reduce death due to lung cancer. The primary hypothesis that drove this investigation was that CT imaging provides higher resolution in-vivo data that would detect cancer at an earlier stage (or smaller size nodule) which is more amenable to treatment and cure.

The NLST CT images and clinical data are now freely available to the biomedical community and CT scans were obtained. NLST study patients were seen at 3 time points, each 1 year apart. These time points are denoted as t0 (baseline), t1 (1 year follow up) and t2 (2 year follow up). Furthermore, "synthetic" time points, denoted as t3, t4 and t5 were further created. These are time points that were created by randomly sampling participants so that the dataset includes patient baseline data (t0) for some patients, 1 year follow up (t1) data for some patients, and 2 year follow up (t2) data for some patients. For example, the synthetic time point t3 assumes that ⅓ of patients have no prior imaging and thus are sampled at t0, ⅓ have 1 year of prior imaging and thus are sampled at t1, and ⅓ have multiple (in this case 2) years of prior imaging, and thus are sampled at t2. For t4, the sampling is 2:1:1 (t0:t1:t2) and for t5 the sampling is 1:1:2 (t0:t1:t2). This was done to mimic clinical data where some people have never had a CT scan of the chest, some people have had a prior CT scan of the chest and some people have had more than one prior CT scan of the chest.

Image analytic algorithms were applied to CT images to extract features such as emphysema, interstitial change, preserved lung tissue and pectoralis muscle size (area)

where the latter muscle measure is used as a proxy for body composition or fat free mass. The CT scans captured at different timepoints were divided in half to build a dedicated training set of data and testing set of data. Using nodule and non-nodule specific features extracted from the CT images as well as longitudinal features (e.g., longitudinal non-nodule specific features and longitudinal nodule specific features), robust risk prediction models for predicting future lung cancer were created.

Features (e.g., variables) were extracted from the CT images. The features included were chosen based on prior experience and based on likely biologic relevance.

For the risk prediction models described in the Examples below, example non-nodule specific features are listed below. A more comprehensive list of non-nodule specific features are shown in Table 2.

1) Densitometric measures of the lung parenchyma
   a. The percentage of lung occupied by:
      i. Low attenuation area (LAA), which was defined as the area/volume having an attenuation less than −950 Hounsfield units (HU)
      ii. High attenuation area (HAA), which was defined as the area/volume of lung having attenuation between −600 HU and −250 HU.
   b. The ratio between LAA in the upper lung zone to that in the lower lung zone (Ratio LAA)
2) Body composition measures of the musculature/chest wall
   a. Pectoralis major cross-sectional area
   b. Pectoralis minor cross-sectional area
   c. Pectoralis major lean cross-sectional area
   d. Pectoralis minor lean cross-sectional area
   e. Subcutaneous fat cross-sectional area (axial)
3) Local histogram measures of the lung parenchyma
   a. The percentage of lung occupied by:
      i. Normal tissue
      ii. Centrilobular emphysema
      iii. Centrilobular nodule
      iv. Ground glass
      v. Honeycombing
      vi. Linear scar
      vii. Nodular
      viii. Reticular
      ix. Subpleural line
      x. Other emphysema
      xi. Cyst
4) Longitudinal non-nodule specific features (e.g., changes in densitometric measures of the lung parenchyma, changes in body composition measures, and/or changes in local histogram measures of the lung parenchyma) (not included in single timepoint risk prediction models)

Figure 6A:
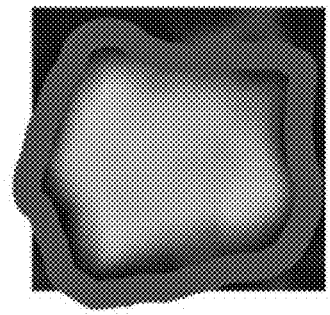
FIG. 6A shows example radiomic shells.
Figure 6A:
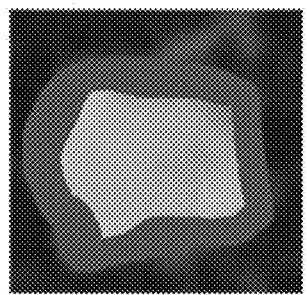
Figure 6A:
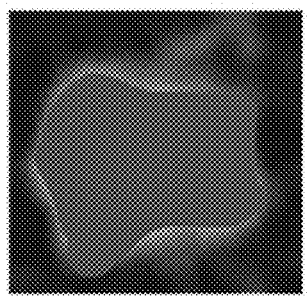

For the risk prediction models described in Examples below, nodule-specific features (e.g., features of the lung nodule, the edge of the lung nodule, and the boundary/peri-nodule area) were analyzed. Nodule-specific features were extracted from three shells of tissue: the interior of the nodule, the edge of the nodule and the boundary region/peri-nodular area. Additionally, radiomic shells were generated for individual nodules in 3 different images (e.g., original CT image, a wavelet transformed CT image, and a Gaussian transformed CT image) as shown in FIG. 6A.

Example nodule specific features are listed below.
1) Attenuation
2) Margin description
3) Diameter
4) Lung CT Screening, Reporting and Data System (Lung-RADS) Score
5) Longitudinal nodule specific features (e.g., change in attenuation, change in margin description, change in diameter, and/or change in Lung-RADS score) (not included in single timepoint risk prediction models)

For the risk prediction models described in the Examples below, the following radiomic features (e.g., nodule-specific features) were extracted from the original CT image, a wavelet transformed CT image, and a Gaussian transformed CT image.
1) First order statistics
2) 3D shape based features
3) 2D shape based features
4) Gray level co-occurrence matrix
5) Gray level run length matrix
6) Gray level size zone matrix
7) Neighboring gray tone difference matrix
8) Gray level dependence matrix.

A more comprehensive list of nodule-specific features are shown in Table 3.

Longitudinal radiomic features were further calculated as the change of any of the radiomic features described above between CT images captured from two or more different timepoints. Note, longitudinal radiomic features were not included in single timepoint risk prediction models.

The features used specifically did not include clinical characteristics, meaning that the clinical characteristics of the overall cohort were the NLST characteristics. The clinical characteristics by lung cancer prediction category are shown below.

Figure 6B:
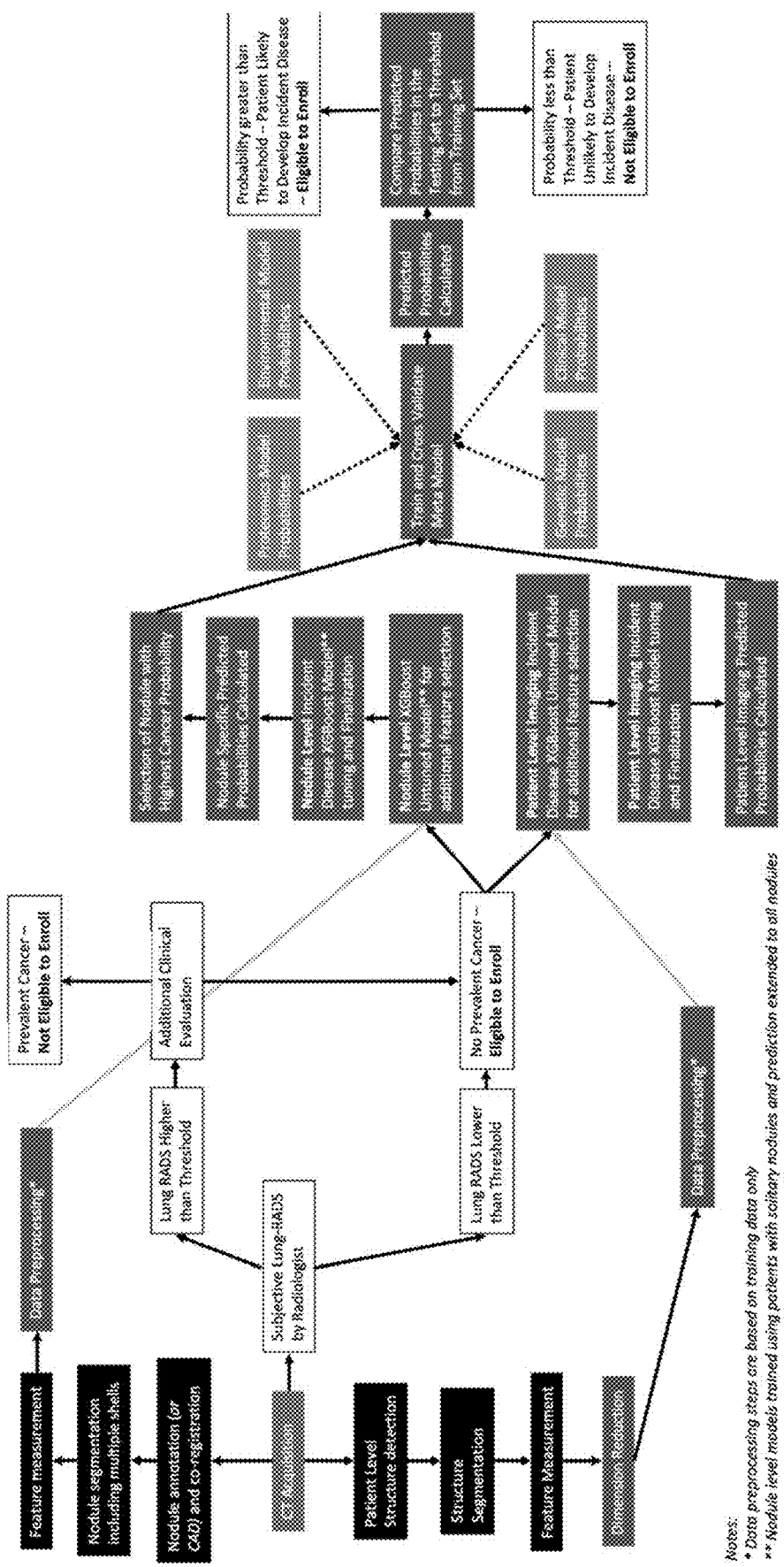
FIG. 6B depicts an example overview of the implementation of a risk prediction model, in accordance with the embodiment shown in FIG. 3A.
Figure 8:
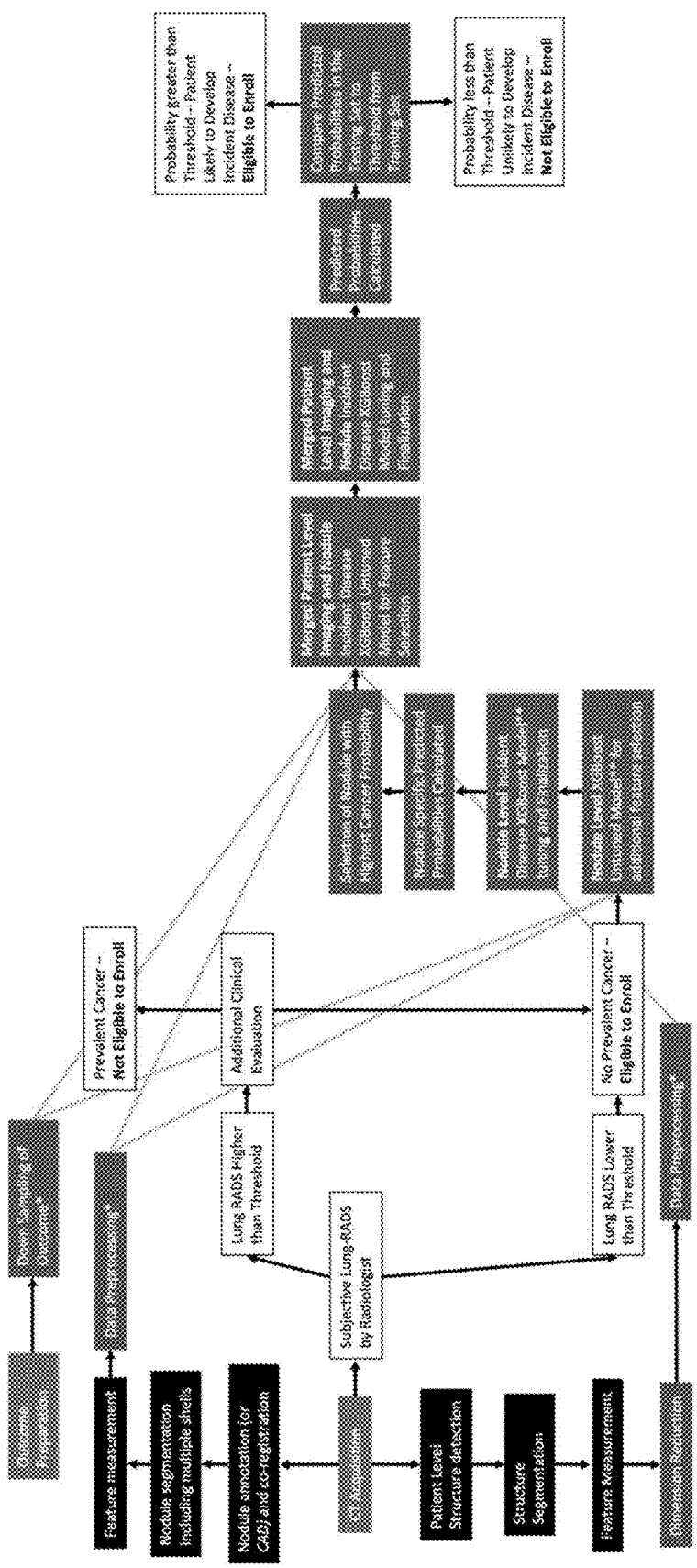
FIG. 8 depicts an example overview of the implementation of a risk prediction model, in accordance with the embodiment shown in FIG. 3B.

FIGS. 6B and 8 depict two overview flow diagrams for implementing risk prediction models. Specifically, FIG. 6B depicts an example overview of the implementation of a risk prediction model, in accordance with the embodiment shown in FIG. 3A. Here, features of the nodule and immediate surround) were analyzed separately from the non-nodule specific features by two separate submodels of the risk prediction model. The outputs of the analyses from the two submodels were provided as input to a third submodel (e.g., identified as "Train and Cross Validate Meta Model") for predicting likelihood of developing cancer. As shown in FIG. 6B, this third submodel further received, as input, other values derived from other features, such as proteomics determined from the patient, environmental conditions experienced by the patient, genetics of the patient, and/or clinical characteristics of the patient. FIG. 8 depicts an example overview of the implementation of a risk prediction model, in accordance with an embodiment shown in FIG. 3B. Here, nodule specific features and non-nodule specific features were merged and analyzed together by a risk prediction model. Thus, the risk prediction model predicts probabilities for predicting likelihood of developing cancer.

Risk prediction models were predicated on a mixture of non-nodule and nodule specific features extracted from the CT image. Features on CT can vary by CT scanner brand, generation and image reconstruction software. Additional geographic variability in the burden of disease between subjects may reflect actual differences to noxious exposure (i.e. some people may be more or less susceptible to injury from exposure and more or less likely to develop emphysema or interstitial changes in the lung tissue). For these reasons, absolute thresholds to determine the presence and severity of CT metrics of disease were not used in this example. Instead, the data in the test sub cohort were each normalized by subtracting the mean and dividing by the standard deviation for each covariable. As additional cohorts are aggregated for model refinement, data normalization will be performed using all existing data (cross cohort) or select subsets of the data including but not limited to those thought to best reflect the patient specific biology, exposure history, ethnicity or type of medical image being processed. Once normalized, the data were used in the XGBoost-based approach to modeling.

Pre-processing of the data was first conducted. This included normalizing values of continuous features (e.g., by centering (subtraction of the mean) and scaling (division by the standard deviation). The normalization of the test set was performed using information from the training set only. That is, the training set mean and standard deviation were used to normalize both the training set and the test set. Additionally, pre-processing included down sampling of the majority class (no cancer) was performed in order to account for imbalanced data, i.e. to account for the fact that cancer diagnosis is relatively uncommon. Alternative approaches such as SMOTE and ROSE were considered but had similar performance as down sampling with higher computational requirements.

To build the risk prediction model, XGBoost was primarily used. The gradient boosted models were independently trained to 3-year risk of future lung cancer in smokers enrolled in the NLST. The model strategy developed and optimized decision trees in the training data to predict a desired outcome. This approach was used rather than selecting a fixed threshold for a certain burden of disease (i.e. >10% emphysema or >10% interstitial change) because there are potentially several combinations of emphysema, interstitial change and sarcopenia that identify a heightened risk of lung cancer. For example, a smoker having 25% of their lung with emphysema may have the same heightened risk for future lung cancer as the smoker with 2% emphysema, 12% interstitial change and decreased pectoralis muscle area. These models were then modified to enable prediction of incident (new) cancer rather than just identify those with prevalent (e.g., already present) cancer on the CT scan. This final step leveraged visual data describing features of any lung nodules in the CT image. Although the exemplary embodiments show and describe gradient boosted models, it will be understood by those of skill in the art that other modeling approaches such as, for example, logistic regression may also be utilized. It will also be understood by those of skill in the art that although the risk prediction models are specifically shown and described as providing 3 year risk predictions, prediction terms may be varied, as desired.

To build the risk prediction model, the cohort was split 50/50 into training and testing groups. Models were trained on the testing group with tuning performed using 10 fold cross validation repeated three times. Dichotomization of predicted probabilities was performed by using information from the training group only. For this example this was performed by selecting the probability threshold that maximized the sensitivity for a given screen to enroll ratio, however it should be understood that other approaches such as maximizing specificity for a given positive predictive value target can also be employed. Stability of the predicted probability threshold was obtained using a bootstrap sample method with 1000 repeats. Outcomes modeled included the diagnosis of cancer at a 3 year horizon. Performance measures and visualization include presentation of ROC curves and enrichment for all time points (as described in the Examples below). The cumulative incidence function based on 3 year cancer prediction were also predicted/shown in the Examples below.

Models were constructed to predict future risk of cancer for either the entire cohort of patients or a subgroup of patients. Subgroups of patients were categorized based on nodules which were at baseline rated/categorized as Lung-RADS <4B, <4A, <3 and <2. Lung-RADS <4B includes patients categorized as Lung-RADS 1-4A. Lung-RADS <4A includes patients categorized as Lung-RADS 1-3. Lung-RADS <3 includes patients categorized as Lung-RADS 1-2. Lung-Rads <2 includes patients categorized as Lung-RADS 1. Table 1 summarizes the characteristics for different Lung-RADS classifications. Demographic information and patient characteristics of the patient cohorts used to build risk prediction models shown in FIGS. 6B and 8 are shown FIG. 7A and FIG. 9A, respectively.

As shown in the Examples below, all results represent the performance/findings based on models developed/trained in the training cohort and then applied to the testing cohort.

When interpreting the cumulative incidence function plots, the raw probabilities on the y axis can be affected significantly by changes in the risk set due to censoring and death. These plots were included primarily to demonstrate the change in their shape by subgroup.

When reviewing the receiver operating characteristic (ROC) curves and the area under the curve (AUC) values, note that these are primarily included for reference given their familiarity and use in the literature. When considering potential eligibility for enrollment, note that based on Lung-RADS criteria, those individuals with 4A and 4B nodules may warrant early evaluation. However, a significant percentage of both, e.g., 4A, will not necessarily be prevalent cancers and therefore may be potentially able to be enrolled in a potential study of future incident cancer.

Example 2: Predicting Future Risk of Cancer Through Separate Analysis of Nodule and Non-Nodule Features Risk prediction models including a nodule model for analyzing nodule features and a non-nodule model for analyzing non-nodule features were constructed in accordance with the overview shown in FIG. 6B. For each risk prediction model, the output of the nodule model and the non-nodule model served as inputs into a third model (e.g., aggregate model shown in FIG. 3A) which generates probabilities that are indicative of whether a patient is likely to develop lung cancer within a time horizon of 3 years. A training set (e.g., 50% of the cohort) was used to train the risk prediction model and a testing set (e.g., other 50% of the cohort) was used to test the risk prediction model.

Both single timepoint risk prediction models (e.g., risk prediction models analyzing features derived from images at a single timepoint) and longitudinal risk prediction models (e.g., risk prediction models analyzing features derived from images at a single timepoint and longitudinal features across images of two or more timepoints) were constructed. FIG. 7A depicts characteristics of the different risk prediction models across patient cohorts of various different time points (e.g., t0, t1, t2, t3, t4, or t5), in accordance with the embodiment shown in FIG. 3A.

The risk prediction model denoted as "1:1:1 Random Sample from t0, t1, t2 (labelled t3)" was trained on a random, non-overlapping, selection of participants at each of t0, t1, and t2 timepoints. That is for this risk prediction model, a third of patients were analyzed using their t0 data, a third using their t1 data and a third using their t2 data. The risk prediction model denoted as "2:1:1 Random Sample from t0, t1, t2 (labelled t4)" was trained on a random, non-overlapping, selection of participants at each of t0, t1, and t2 timepoints. That is for this risk prediction model, 50% of patients were analyzed using their t0 data, 25% using their t1 data and 25% using their t2 data. The risk prediction model denoted as "1:1:2 Random Sample from t0, t1, t2 (labelled t5)" was trained on a random, non-overlapping, selection of participants at each of t0, t1, and t2 timepoints. That is for this risk prediction model, 25% of patients were analyzed using their t0 data, 25% using their t1 data and 50% using their t2 data.

Of note, the risk prediction models shown in HG 7A achieve an odds ratio between 5 and 8 as well as positive predictive values over 8% with a screen to enroll ratio less than 11 to 1. This is indicative of the usefulness of the risk prediction models for screening patients that are unlikely to develop cancer within the 3 year time horizon. Altogether, the results shown in FIG. 7A indicate that the various future risk prediction models trained using cross-sectional and/or longitudinal features can be implemented for enriching patients, thereby reducing the number of patients that need to be enrolled or could be considered for enrollment in clinical trials.

The subsequent results are in reference to the risk prediction model denoted as "1:1:1 Random Sample from t0, t1, t2 (labelled t3)," which was trained on a random, non-overlapping, selection of participants at each of t0, t1, and t2 timepoints. The patient demographics used to evaluate the risk prediction model is shown in FIG. 7B. Here, patients from each of Lung-RADS 1, Lung-RADS 2, Lung-RADS 3, Lung-RADS 4A, and Lung-RADS 4B were included and future cancer was either predicted or not predicted for each patient. Note that over 60% of the patients identified as being high risk for developing lung cancer were considered to be low risk (lung-RADS 1 or 2) for developing lung cancer using standard lung-RADS scoring.

Figure 7C:
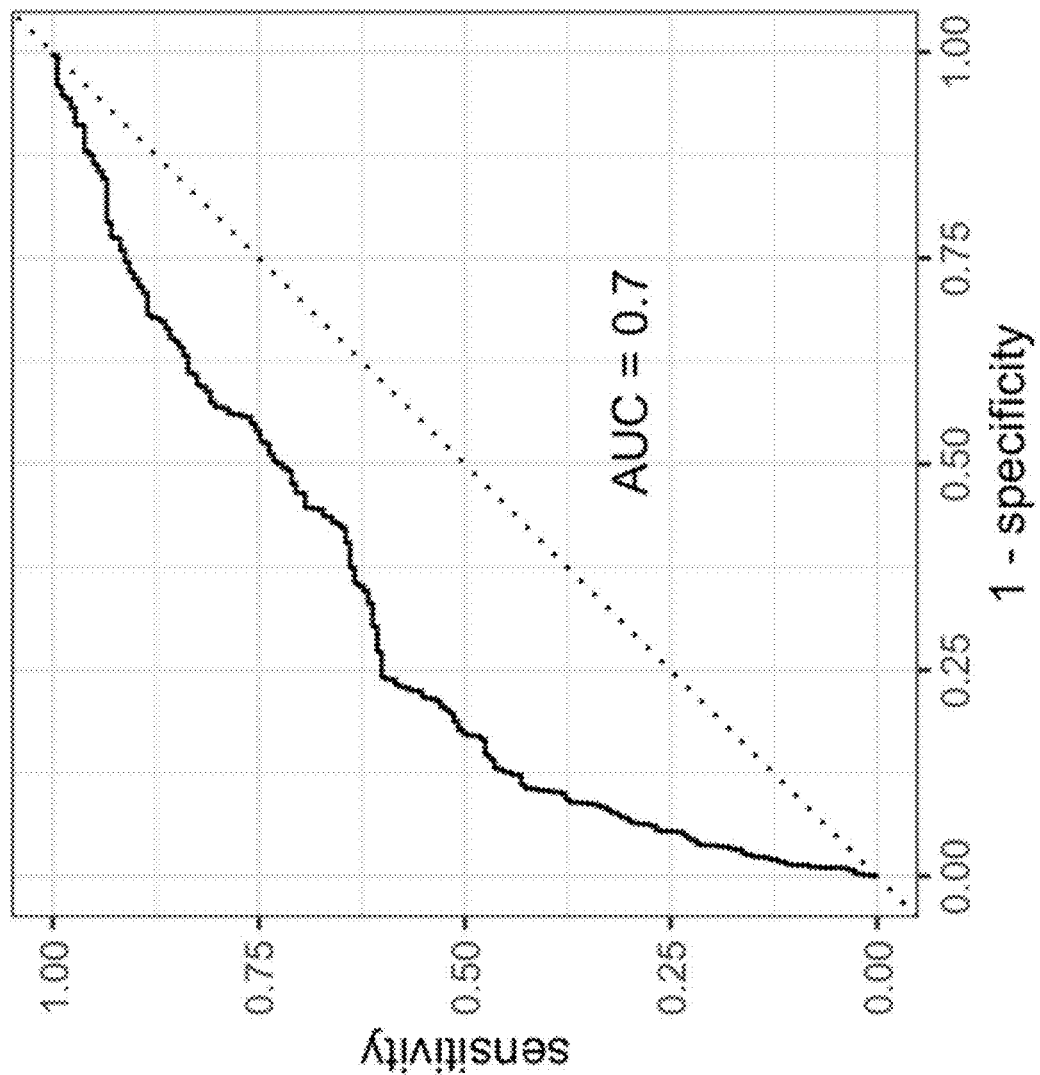
FIG. 7C depicts the performance (as measured by area under the curve (AUC)) of the risk prediction model, in accordance with the embodiment shown in FIG. 3A.
Figure 7D:
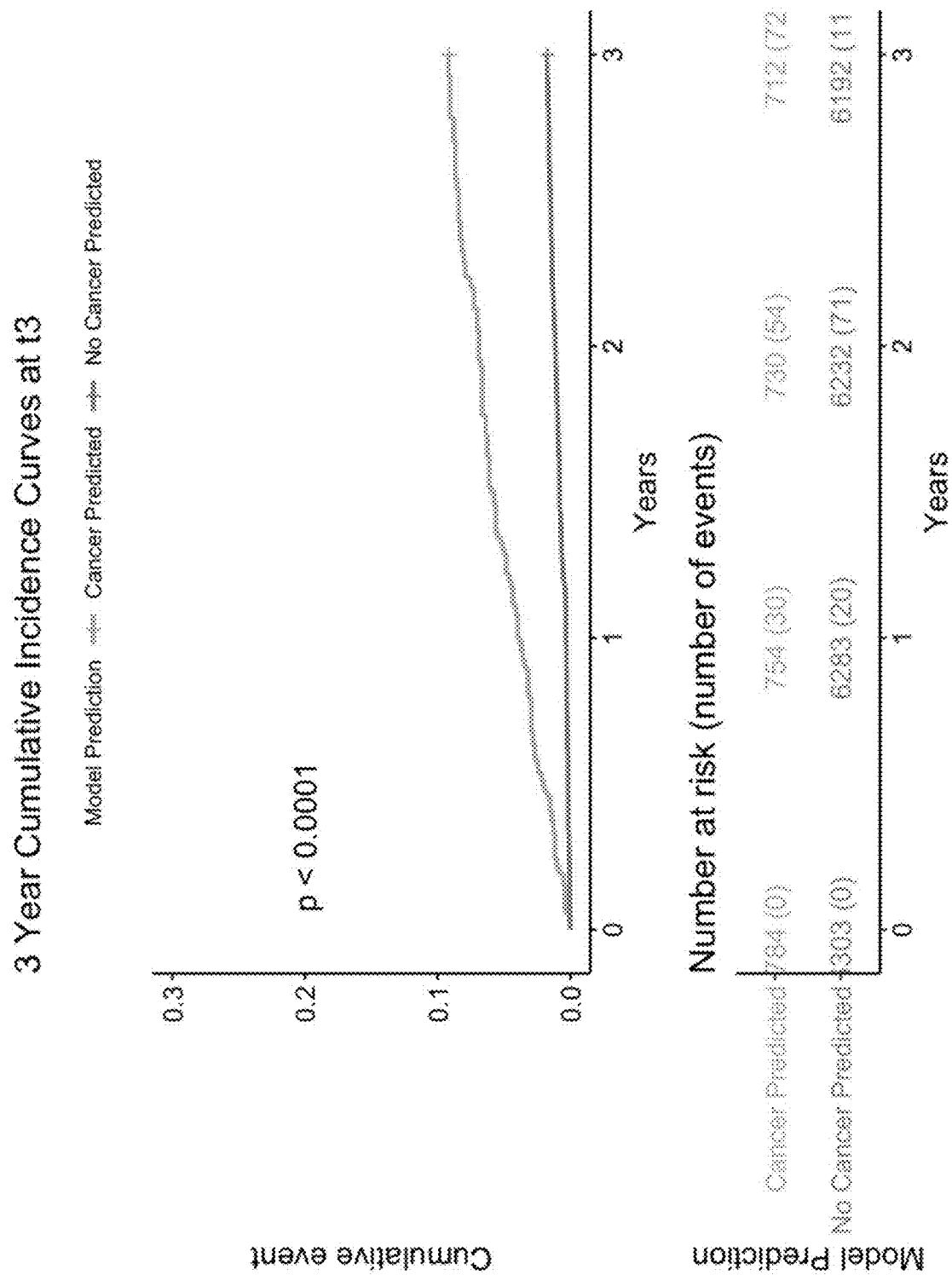
FIG. 7D depicts a 3 year cumulative incidence function as predicted by the risk prediction model, in accordance with the embodiment shown in FIG. 3A.

FIG. 7C depicts the performance (as measured by area under the curve (AUC)) of the risk prediction model. Here, the risk prediction model exhibited an AUC value of 0.70. FIG. 7D depicts a 3 year cumulative incidence function as predicted by the risk prediction model. Here, at 3 years, the risk prediction model predicted cancer for 712 patients and no cancer for the other 6192 patients.

FIG. 7E depicts the top 10 nodule features of the nodule model component of the risk prediction model. Notably, the top 10 features were single timepoint nodule features (e.g., nodule features extracted from an image obtained at a single time point) as opposed to longitudinal nodule features (e.g., change in nodule features across two or more timepoints). This can vary depending on presence and amount of prior imaging data available. FIG. 7F depicts the top 10 non-nodule features of the non-nodule model component of the risk prediction model. Notably, a portion of the top 10 non-nodule features were longitudinal non-nodule features (e.g., "pectoralis major lean Hounsfield units mode change," "pectoralis major lean hounsfield units standard deviation change," "normal parenchyma low attenuation area change," and "pectoralis major Hounsfield units mode change"). Thus, this indicates that longitudinal non-nodule features that capture change in a subject's non-nodule based characteristics (e.g., changes in the lung parenchyma and/or body composition) were informative for predicting likelihood of future cancer.

Example 3: Predicting Future Risk of Cancer Through Merged Analysis of Nodule and Non-Nodule Features Risk prediction models that did not separately analyze nodule and non-nodule features were constructed in accordance with the overview shown in FIG. 8. Each risk prediction model receives, as input, both nodule and non-nodule features and generates probabilities indicative of whether a patient is likely to develop lung cancer within a time horizon of 3 years. A training set (e.g., 50% of the cohort) was used to train the risk prediction model and a testing set (e.g., other 50% of the cohort) was used to test the risk prediction model.

Figure 9A:
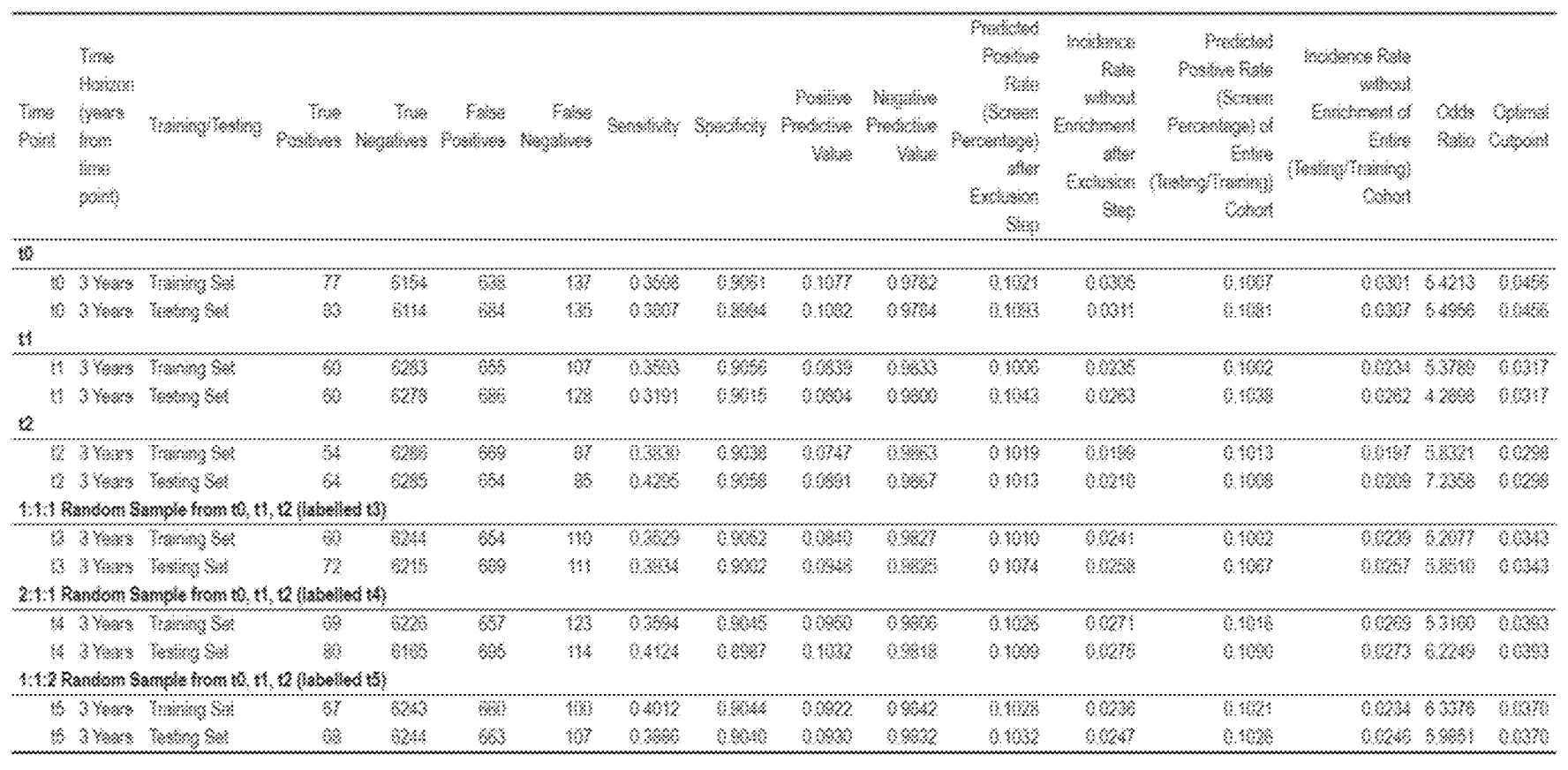

Both single timepoint risk prediction models (e.g., risk prediction models analyzing features derived from images at a single timepoint) and longitudinal risk prediction models (e.g., risk prediction models analyzing features derived from images at a single timepoint and longitudinal features across images of two or more timepoints) were constructed. FIG. 9A depicts characteristics of the different risk prediction models across patient cohorts of various different time points (e.g., t0, t1, t2, t3, t4, or t5), in accordance with the embodiment shown in FIG. 3B.

The risk prediction model denoted as "1:1:1 Random Sample from t0, t1, t2 (labelled t3)" was trained on a random, non-overlapping, selection of participants at each of t0, t1, and t2 timepoints. That is for this risk prediction model, a third of patients were analyzed using their t0 data, a third using their t1 data and a third using their t2 data. The risk prediction model denoted as "2:1:1 Random Sample from t0, t1, t2 (labelled t4)" was trained on a random, non-overlapping, selection of participants at each of t0, t1, and t2 timepoints. That is for this risk prediction model, 50% of patients were analyzed using their t0 data, 25% using their t1 data and 25% using their t2 data. The risk prediction model denoted as "1:1:2 Random Sample from t0, t1, t2 (labelled t5)" was trained on a random, non-overlapping, selection of participants at each of t0, and t2 timepoints. That is for this risk prediction model, 25% of patients were analyzed using their t0 data, 25% using their t1 data and 50% using their t2 data.

Of note, the characteristics of all of the models shown in FIG. 9A includes an odds ratio between 5 and 8 with a positive predictive value greater than 8%. This is indicative of the usefulness of the risk prediction models for screening patients that are unlikely to develop cancer within the 3 year time horizon. Altogether, the results shown in FIG. 9A indicate that the various future risk prediction models trained using cross-sectional and/or longitudinal features can be implemented for enriching patients, thereby reducing the number of patients enrolled in clinical trials or identifying patients who may best benefit from therapeutic strategies (e.g., in one or more clinical trials) that reduce their risk of developing lung cancer.

The subsequent results are in reference to the risk prediction model denoted as "1:1:1 Random Sample from t0, t1, t2 (labelled t3)," which was trained on a random, non-overlapping, selection of participants at each of t0, t1, and t2 timepoints. The patient demographics used to evaluate the risk prediction model are shown in FIG. 9B. Here, patients from each of Lung-RADS 1, Lung-RADS 2, Lung-RADS 3, Lung-RADS 4A, and Lung-RADS 4B were included and future cancer was either predicted or not predicted for each patient.

Figure 9C:
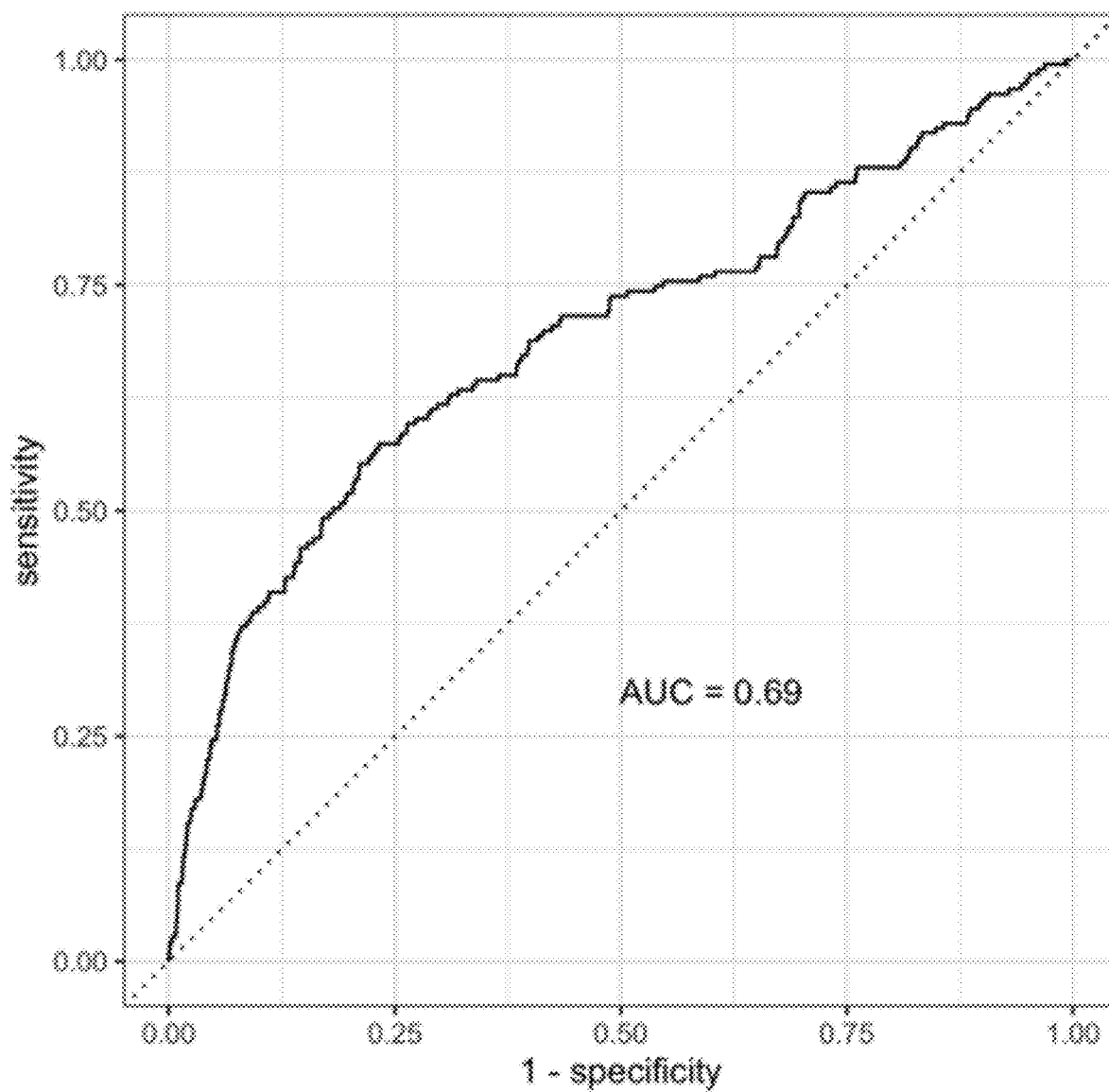
FIG. 9C depicts the performance (as measured by area under the curve (AUC)) of the risk prediction model, in accordance with the embodiment shown in FIG. 3B.
Figure 9D:
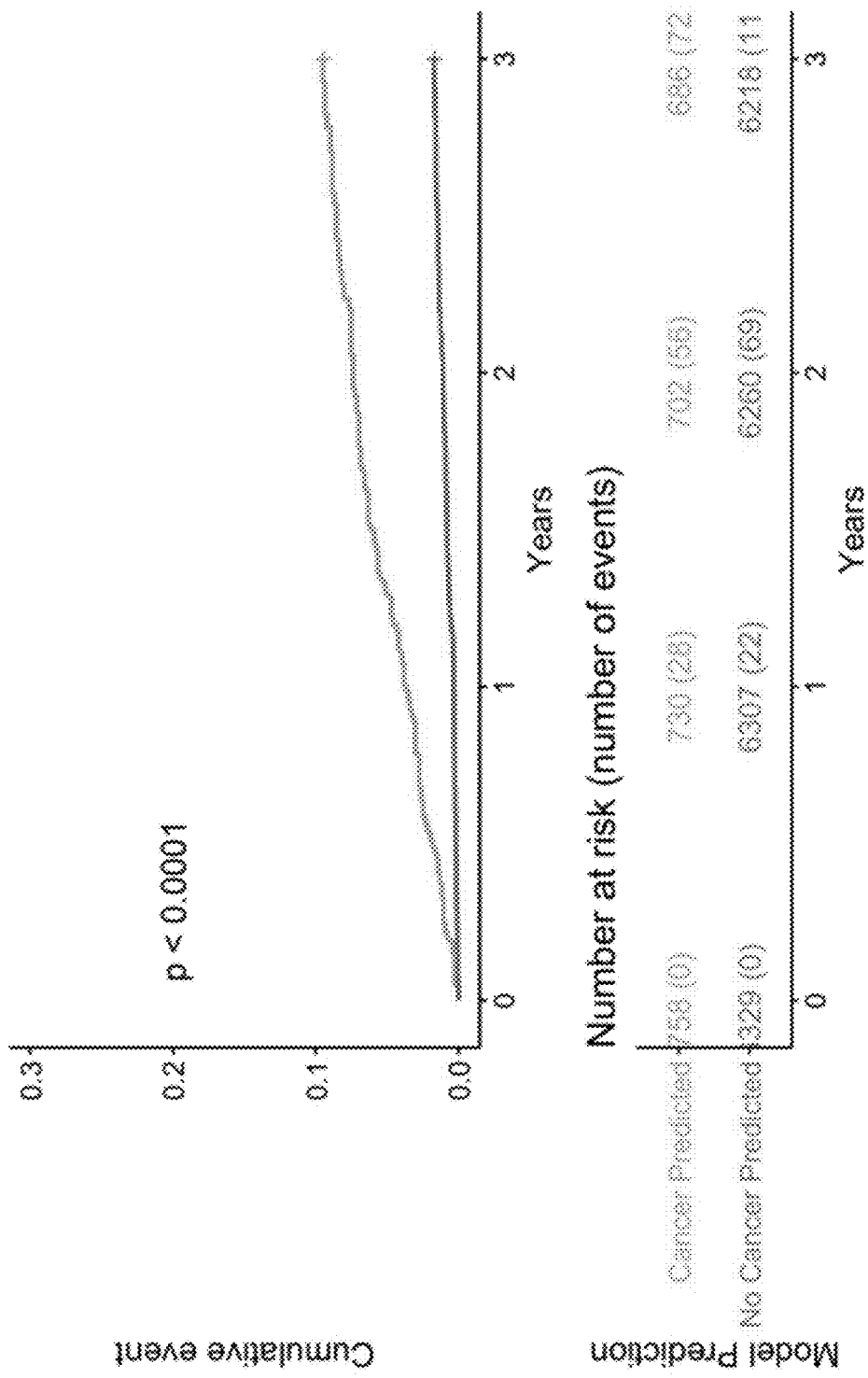
FIG. 9D depicts a 3 year cumulative incidence function as predicted by the risk prediction model, in accordance with the embodiment shown in FIG. 3B.

FIG. 9C depicts the performance (as measured by area under the curve (AUC)) of the risk prediction model. Here, the risk prediction model exhibited an AUC value of 0.69. FIG. 9D depicts a 3 year cumulative incidence function as predicted by the risk prediction model. Here, the risk prediction model predicted cancer for 758 patients and no cancer for the other 6329 patients. FIG. 9E depicts the top 10 features (e.g., nodule and non-nodule features) of the risk prediction model, in accordance with the embodiment shown in FIG. 3B.

Example 4: Predicting Future Risk of Cancer Through Separate Analysis of Nodule and Non-Nodule Features in Lunt-Rads 1-3 Patients where Longitudinal Nodule Features are Informative Risk prediction models including a nodule model for analyzing nodule features and a non-nodule model for analyzing non-nodule features were constructed in accordance with the overview shown in FIG. 6B. For each risk prediction model, the output of the nodule model and the non-nodule model served as inputs into a third model (e.g., aggregate model shown in FIG. 3A) which generates probabilities that are indicative of whether a patient is likely to develop lung cancer within a time horizon of 3 years. A training set (e.g., 50% of the cohort) was used to train the risk prediction model and a testing set (e.g., other 50% of the cohort) was used to test the risk prediction model.

The subsequent results are in reference to the risk prediction model trained on a random, non-overlapping, selection of participants at a t1 timepoint. The patient demographics used to evaluate the risk prediction model is shown in FIG. 10A. Here, patients from each of Lung-RADS 1, Lung-RADS 2, and Lung-RADS 3 were included and future cancer was either predicted or not predicted for each patient. Notably, Lung-RADS 4A and Lung-RADS 4B patients were excluded. Thus, this model is trained to predict future risk of cancer in patients that may typically be deemed lower risk due to lack of a nodule or small size of a nodule.

Figure 10B:
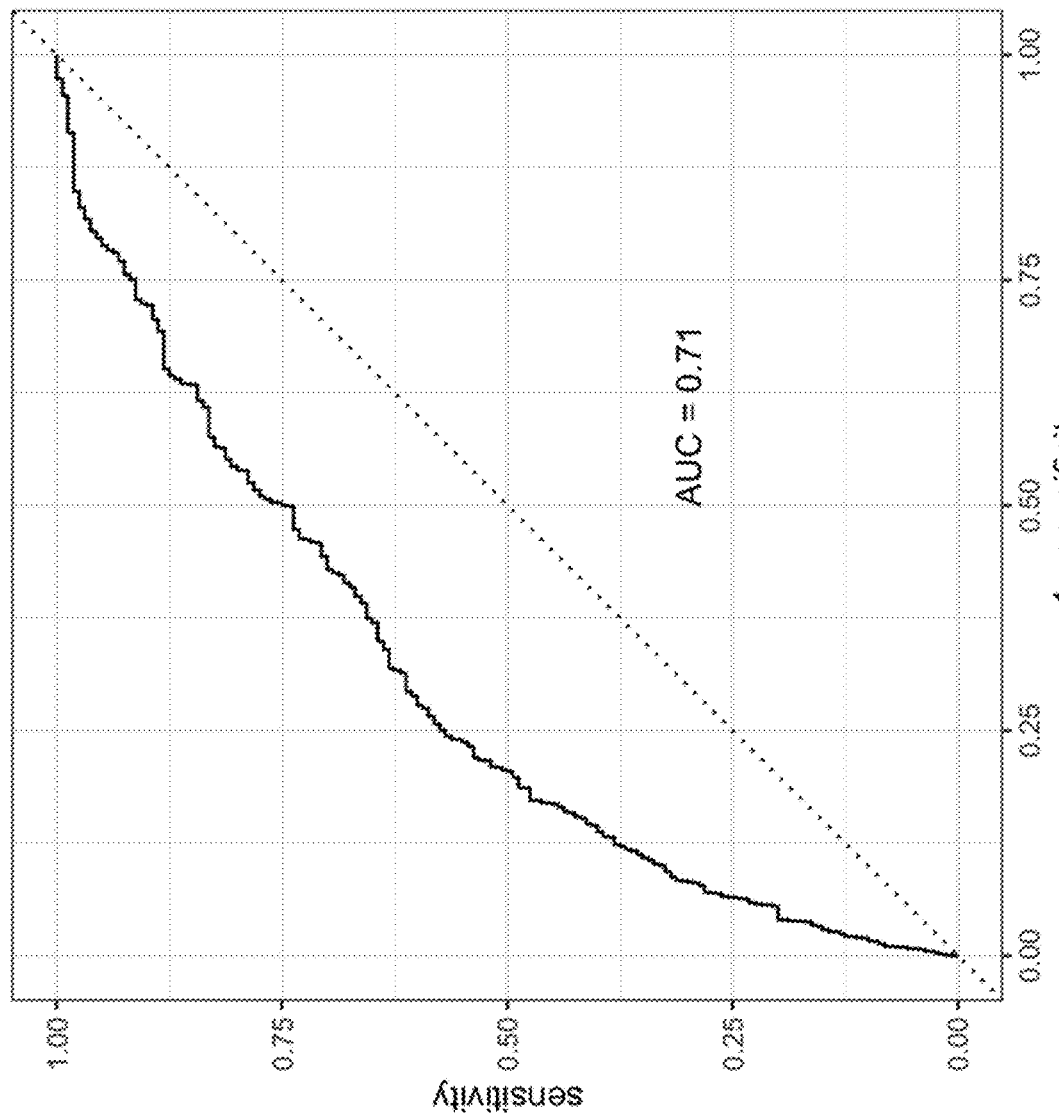
FIG. 10B depicts the performance (as measured by area under the curve (AUC)) of the risk prediction model trained and tested using Lung-RADS 1-3 patients at a t1 timepoint.
Figure 10C:
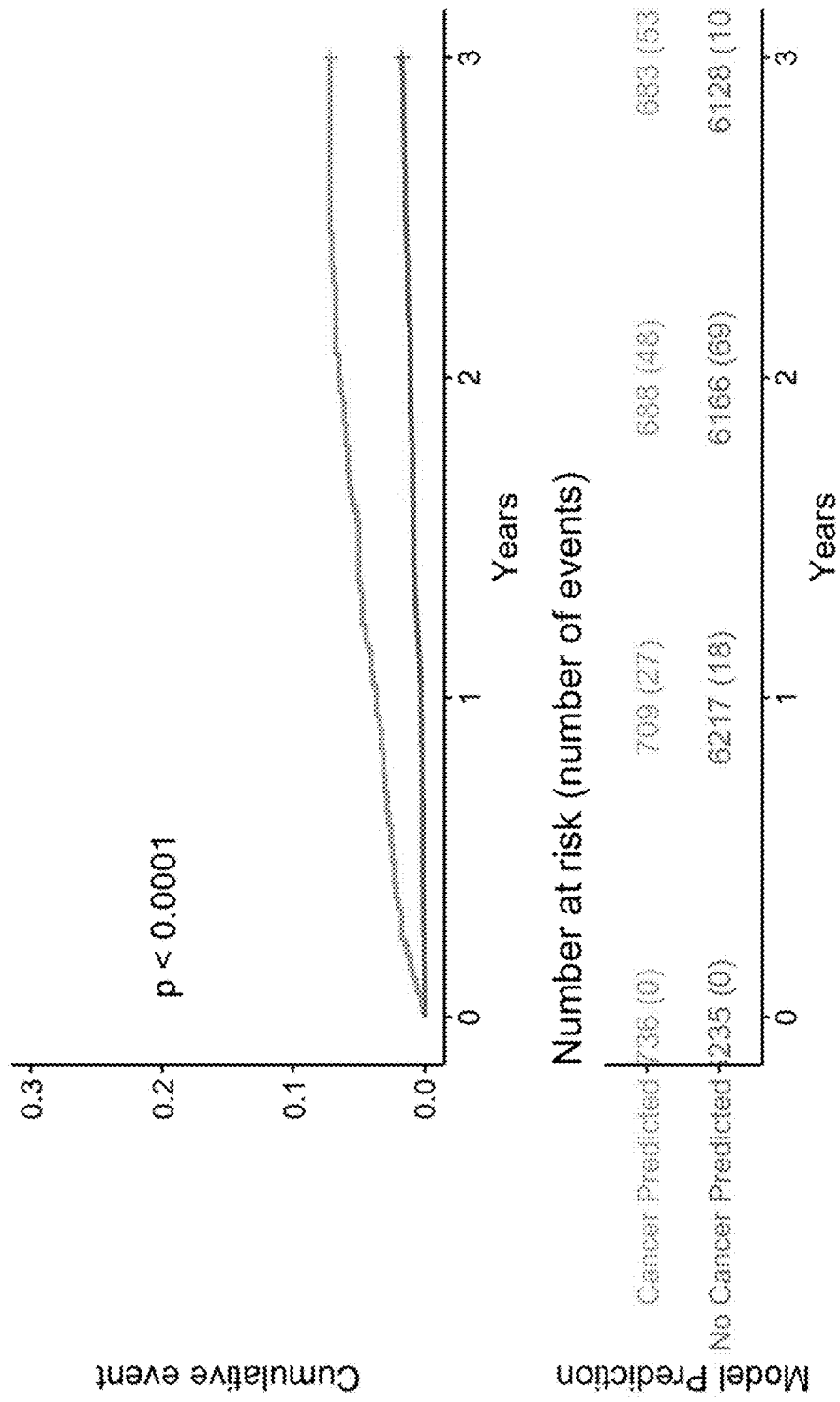
FIG. 10C depicts a 3 year cumulative incidence function as predicted by the risk prediction model using Lung-RADS 1-3 patients at a t1 timepoint.

FIG. 10B depicts the performance (as measured by area under the curve (AUC)) of the risk prediction model. Here, the risk prediction model exhibited an AUC value of 0.71. FIG. 10C depicts a 3 year cumulative incidence function as predicted by the risk prediction model. Here, the risk prediction model predicted cancer for 736 patients and no cancer for the other 6235 patients.

FIG. 10D depicts the top 10 nodule features of the nodule model component of the risk prediction model. Notably, the top 10 features were longitudinal nodule features (e.g., longitudinal nodule features representing difference across two timepoints) as opposed to single timepoint nodule features (e.g., nodule features at a single timepoint). FIG. 10E depicts the top 10 non-nodule features of the non-nodule model component of the risk prediction model. Altogether, the results described in this example indicate a longitudinal risk model that incorporates at least one or more longitudinal features (e.g., longitudinal nodule features that capture change in a subject's nodule based characteristics) is informative for predicting likelihood of future cancer.

Example 5: Predicting Future Risk of Cancer Through Separate Analysis of Nodule and Non-Nodule Features in Lunt-Rads 1-3 Patients where Longitudinal Non-Nodule Features are Informative Risk prediction models including a nodule model for analyzing nodule features and a non-nodule model for analyzing non-nodule features were constructed in accordance with the overview shown in FIG. 6B. For each risk prediction model, the output of the nodule model and the non-nodule model served as inputs into a third model (e.g., aggregate model shown in FIG. 3A) which generates probabilities that are indicative of whether a patient is likely to develop lung cancer within a time horizon of 3 years. A training set (e.g., 50% of the cohort) was used to train the risk prediction model and a testing set (e.g., other 50% of the cohort) was used to test the risk prediction model.

The subsequent results are in reference to the risk prediction model trained on a random, non-overlapping, selection of participants at a t2 timepoint. The patient demographics used to evaluate the risk prediction model is shown in FIG. 11A. Here, patients from each of Lung-RADS 1, Lung-RADS 2, and Lung-RADS 3 were included and future cancer was either predicted or not predicted for each patient. Notably, Lung-RADS 4A and Lung-RADS 4B patients were excluded. Thus, this model is trained to predict future risk of cancer in patients that may typically be deemed lower risk due to lack of a nodule or small size of a nodule.

Figure 11B:
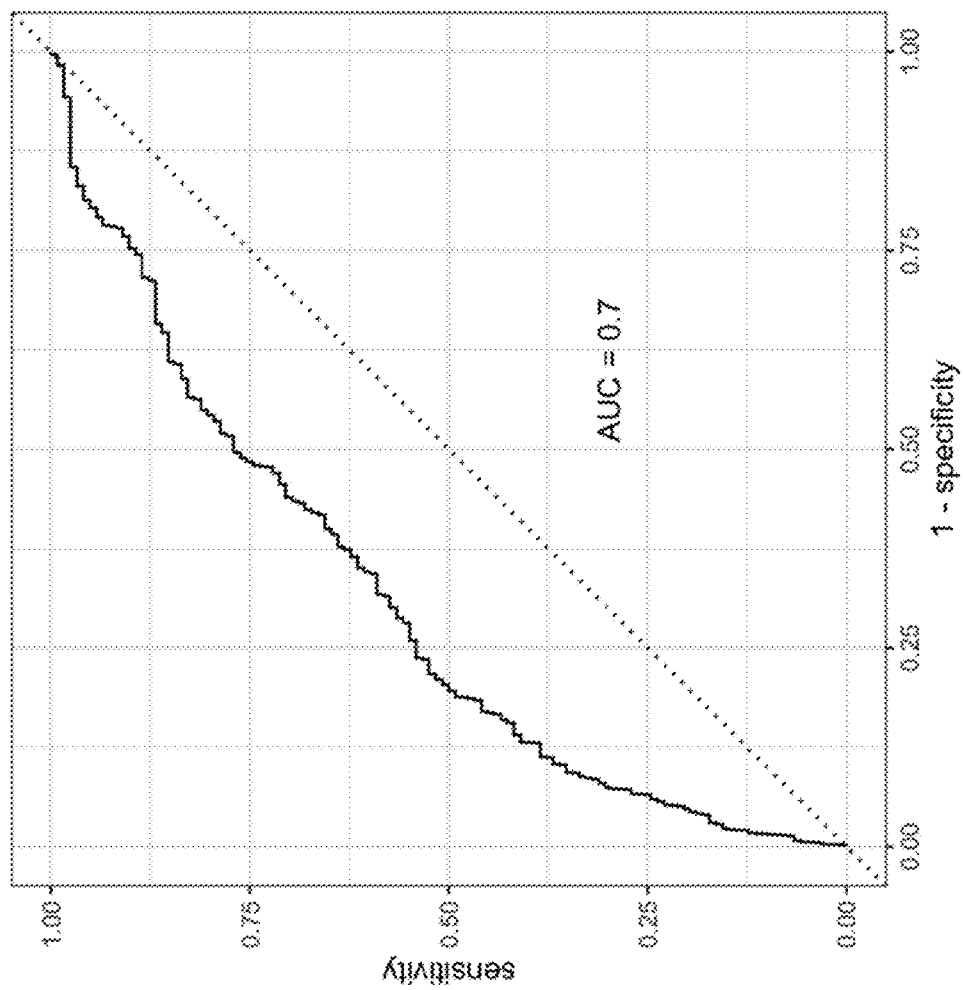
FIG. 11B depicts the performance (as measured by area under the curve (AUC)) of the risk prediction model trained and tested using Lung-RADS 1-3 patients at a t2 timepoint.
Figure 11C:
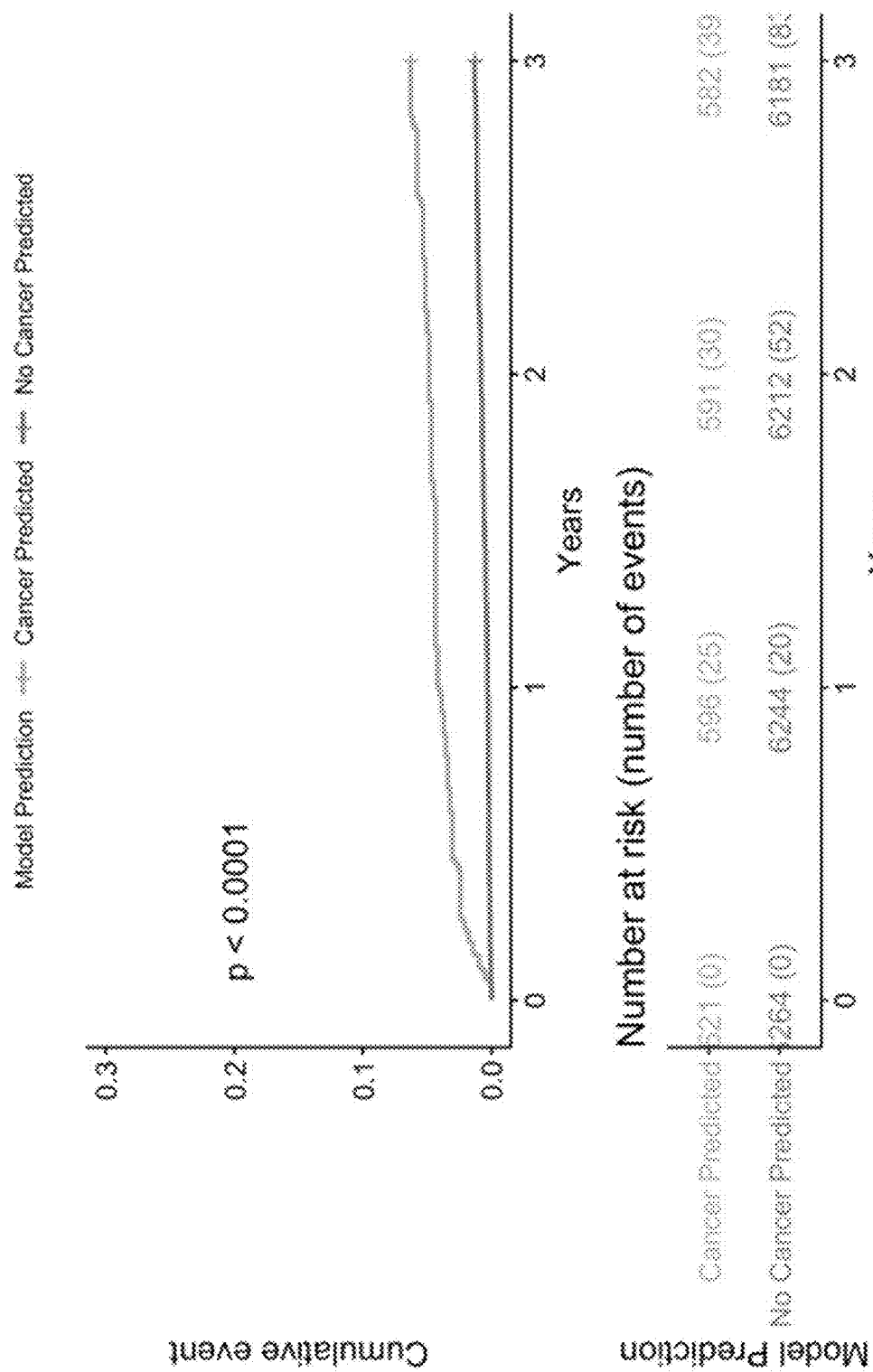
FIG. 11C depicts a 3 year cumulative incidence function as predicted by the risk prediction model using Lung-RADS 1-3 patients at a t2 timepoint.

FIG. 11B depicts the performance (as measured by area under the curve (AUC)) of the risk prediction model. Here, the risk prediction model exhibited an AUC value of 0.70. FIG. 11C depicts a 3 year cumulative incidence function as predicted by the risk prediction model. Here the risk prediction model predicted cancer for 621 patients and no cancer for the other 6264 patients.

FIG. 11D depicts the top 10 nodule features of the nodule model component of the risk prediction model. FIG. 11E depicts the top 10 non-nodule features of the non-nodule model component of the risk prediction model. Notably, a portion of the top 10 non-nodule features were longitudinal non-nodule features. For example, four of the top 10 non-nodule were longitudinal non-nodule features (e.g., "wildcard high attenuation area 250 change," "whole lung high attenuation area 250 change," subcutaneous fat hounsfield units skewness change," and "subcutaneous fat lean hounsfield units mean change"). Thus, this indicates that longitudinal non-nodule features that capture change in a subject's non-nodule based characteristics (e.g., changes in the lung parenchyma and/or body composition) were informative for predicting likelihood of future cancer.

Example 6: Predicting Future Risk of Cancer Through Separate Analysis of Nodule and Non-Nodule Features in Lunt-Rads 1-3 Patients Using a Single Timepoint Risk Prediction Model Risk prediction models including a nodule model for analyzing nodule features and a non-nodule model for analyzing non-nodule features were constructed in accordance with the overview shown in FIG. 6B. For each risk prediction model, the output of the nodule model and the non-nodule model served as inputs into a third model (e.g., aggregate model shown in FIG. 3A) which generates probabilities that are indicative of whether a patient is likely to develop lung cancer within a time horizon of 3 years. A training set (e.g., 50% of the cohort) was used to train the risk prediction model and a testing set (e.g., other 50% of the cohort) was used to test the risk prediction model.

The subsequent results are in reference to a single timepoint risk prediction model trained on a random, non-overlapping, selection of participants at a t0 timepoint. The patient demographics used to evaluate the risk prediction model is shown in FIG. 12A. Here, patients from each of Lung-RADS 1, Lung-RADS 2, and Lung-RADS 3 were included and future cancer was either predicted or not predicted for each patient. Notably, Lung-RADS 4A and Lung-RADS 4B patients were excluded. Thus, this model is trained to predict future risk of cancer in patients that may typically be deemed lower risk due to lack of a nodule or small size of a nodule.

Figure 12B:
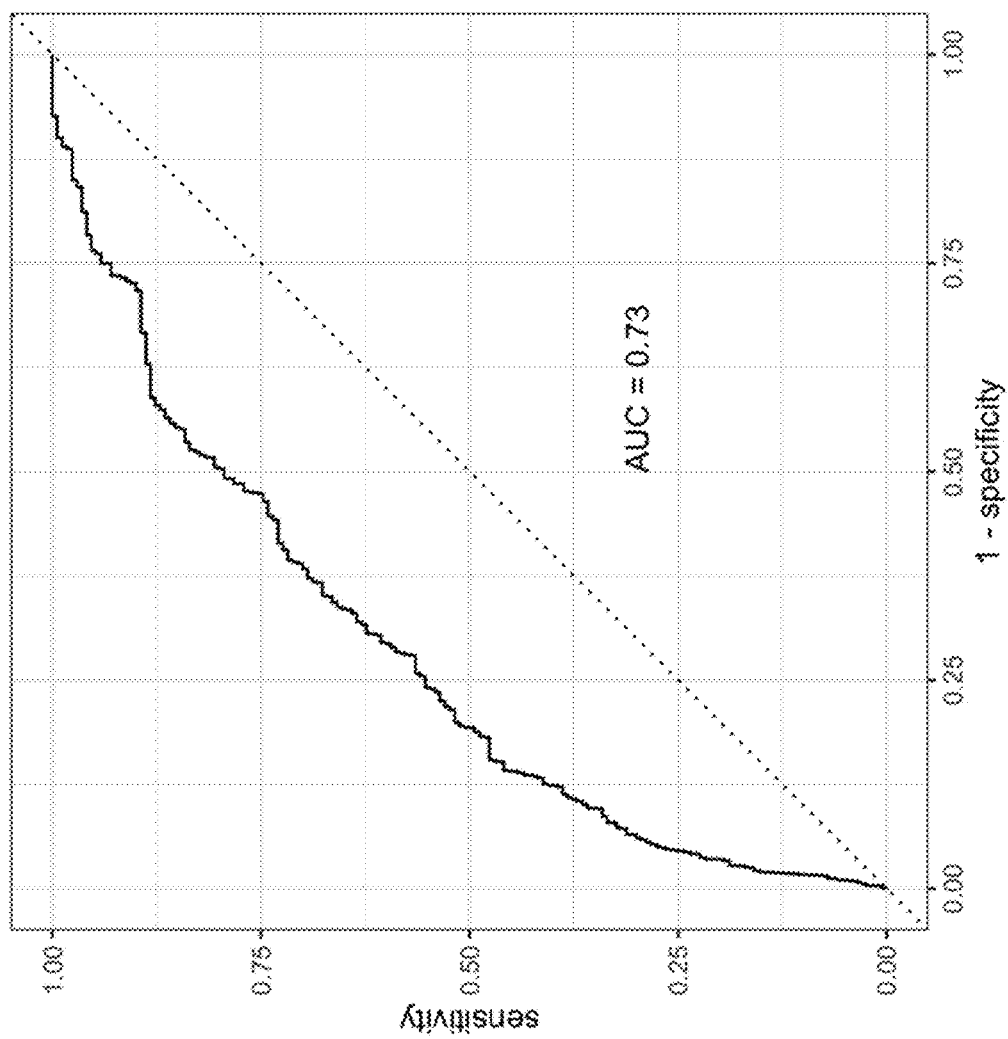
FIG. 12B depicts the performance (as measured by area under the curve (AUC)) of the single-timepoint risk prediction model trained and tested using Lung-RADS 1-3 patients at a t0 timepoint.
Figure 12C:
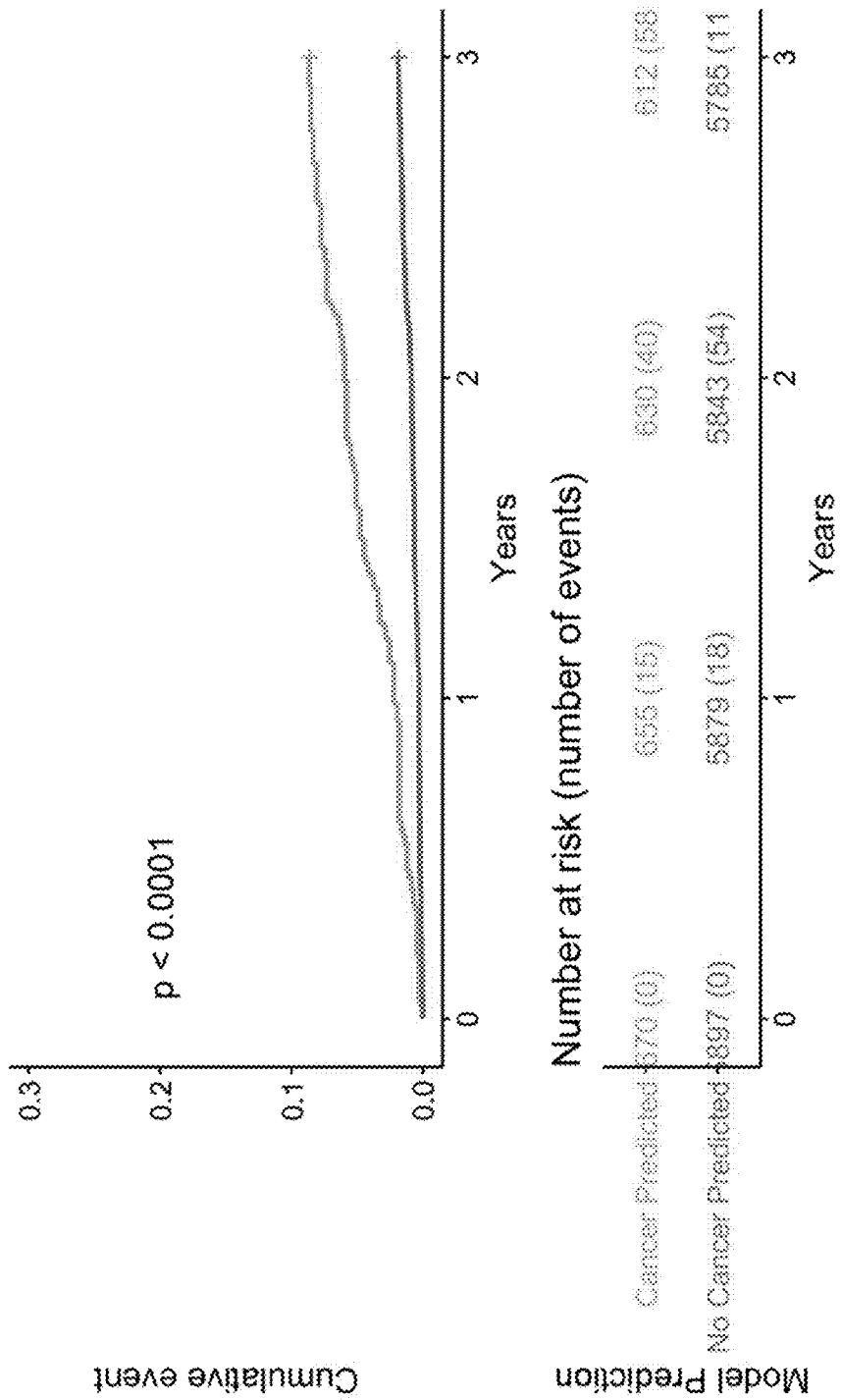
FIG. 12C depicts a 3 year cumulative incidence function as predicted by the single-timepoint risk prediction model using Lung-RADS 1-3 patients at a t0 timepoint.

FIG. 12B depicts the performance (as measured by area under the curve (AUC)) of the risk prediction model. Here, the risk prediction model exhibited an AUC value of 0.73. FIG. 12C depicts a 3 year cumulative incidence function as predicted by the risk prediction model. Here, the risk prediction model predicted cancer for 670 patients and no cancer for the other 5897 patients.

FIG. 12D depicts the top 10 nodule features of the nodule model component of the risk prediction model. FIG. 12E depicts the top 10 non-nodule features of the non-nodule model component of the risk prediction model. Altogether, these results indicate that a single timepoint risk prediction model that includes nodule features and non-nodule features derived from single timepoints were informative for predicting likelihood of future cancer.

Example 7: Predicting Existing or Prevalent Cancer Using a Risk Prediction Model for Lung-Rads 2-4B Patients A risk prediction models for distinguishing nodules based on nodule-specific features were constructed. Here, the risk prediction model was constructed to predict presence or absence of existing or prevalent cancer in a subject. In this example, prevalent cancer refers to cancer diagnosed within 6 months. Lung-RADS 2-4B subjects were specifically chosen for this analysis because these represents subjects with a presence of one or more nodules.

Figure 13A:
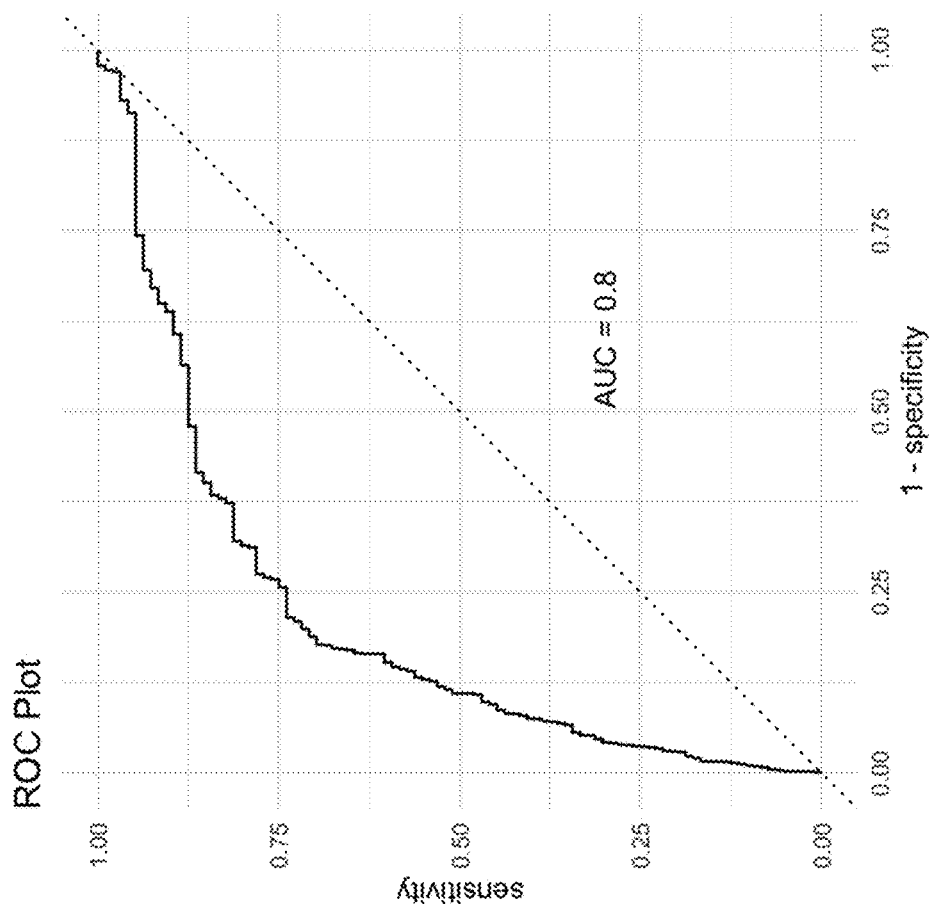
FIG. 13A depicts the performance (as measured by area under the curve (AUC)) of a risk prediction model trained and tested using Lung-RADS 2-4B patients for predicting prevalent or existing cancer.

FIG. 13A depicts the performance (as measured by area under the curve (AUC)) of a risk prediction model trained and tested using Lung-RADS 2-4B patients for predicting prevalent or existing cancer. FIG. 13B shows the patient demographics used for training and testing a risk prediction model using Lung-RADS 2-4B patients for predicting prevalent or existing cancer. FIG. 13C further shows the resulting predictions of a risk prediction model using Lung-RADS 2-4B patients for predicting prevalent or existing cancer.

As shown in FIG. 13A, the risk prediction model achieved an AUC=0.8 for predicting presence or absence of existing or prevalent cancer in Lung RADS 2-4B subjects, based on one or more nodules present in the subjects. In FIG. 13B, a notable result was that the risk prediction model correctly predicted presence of cancer for 13 Stage 1A subjects and 4 Stage 1B subjects. This suggests that the risk prediction model may be able to identify subjects with early stages of cancer.

In FIG. 13C, the notable results include the diagnostic odds ratio, the number needed to screen, and the negative predictive value. Specifically, the diagnostic odds ratio of 8.93 reflects that someone in this group who is predicted to have lung cancer has an 8.9 fold higher odds of currently having lung cancer than someone who is not predicted to have lung cancer. The number needed to screen value of 4.495 in this example suggests that only ~4.5 individuals were needed to be analyzed to identify one case of lung cancer. Finally, the negative predictive value of 98.2 in this example indicates that if a subject is predicted to have an absence of lung cancer, then the subject can be 98.2% confident that they do not have lung cancer.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

TABLE 1

Summary of Lung-RADS classification

| Category Descriptor | Lung-RADS score | Findings | Management | Risk of Malignancy | Estimated Population Prevalence |
|---|---|---|---|---|---|
| Incomplete | 0 | Prior Chest CT examination(s) being located for comparison. Part or all of lungs cannot be evaluated | Additional Lung cancer screening CT images and/or comparison to prior chest CT examinations is needed | N/A | 1% |
| Negative (No nodules and definitely benign nodules) | 1 | No lung nodules or nodules with specific calculations: complete, central, popcorn, concentric rings, and fat containing nodules | Continue annual screening with LDCT in 12 months | <1% | 90% |
| Benign appearance or behavior (Nodules with very low likelihood of becoming a clinically active cancer due to size or lack of growth) | 2 | Solid nodules: <6 mm, new <4 mm Part solid nodules: <6 mm total diameter on baseline screening Non solid nodules (GGN): <30 mm OR ≥30 mm and unchanged or slowly growing Category 3 or 4 nodules unchanged for >3 months | | | |

TABLE 1-continued

Summary of Lung-RADS classification

| Category Descriptor | Lung-RADS score | Findings | Management | Risk of Malignancy | Estimated Population Prevalence |
|---|---|---|---|---|---|
| Probably benign (probably benign findings—short term follow up suggested; includes nodules with a low likelihood of becoming a clinically active cancer) | 3 | Solid nodules: >6 to <8 mm at baseline OR new 4 mm to <6 mm Part solid nodules: >6 mm total diameter with solid component <6 mm OR new <6 mm total diameter Non solid nodules (GGN) ≥30 mm on baseline CT or new | 6 month LDCT | 1-2% | 5% |
| Probably suspicious (findings for which additional diagnostic testing is recommended) | 4A | Solid nodule(s): ≥8 to <15 mm at baseline OR growing <8 mm OR new 6 to <8 mm Part solid nodules: ≥6 mm with solid component ≥6 mm to <8 mm OR with a new or growing <4 mm solid component Endobronchial nodule | 3 month LDCT: PET/CT may be used when there is a ≥ 8 mm solid component | 5-15% | 2% |
| Suspicious (Findings for which additional diagnostic testing and/or tissue sampling is recommended) | 4B | Solid nodule: ≥5 mm OR new or growing and ≥8 mm Part solid nodule(s) with: a solid component ≥8 mm OR a new or growing ≥4 mm solid component | Chest CT with or without contrast, PET/CT and/or tissue sampling depending on the probability of malignancy and comorbidities. PET/CT may be used when there is a ≥8 mm solid component. For new large nodules that develop on an annual repeat screening CT, a 1month LDCT may be recommended to address potentially infectious or inflammatory conditions | >15% | 2% |
|  | 4X | Category 3 or 4 nodules with aditional features or imaging findings that increases the suspicion of malignancy |  |  |  |

TABLE 2

Example Non-nodule-Specific Features

| Feature Type | Feature |
|---|---|
| Body Composition Features | pectoralis minor axial cross sectional area |
| Body Composition Features | pectoralis minor coronal cross sectional area |
| Body Composition Features | pectoralis minor Hounsfield units kurtosis |
| Body Composition Features | pectoralis minor Hounsfield units maximum |
| Body Composition Features | pectoralis minor Hounsfield units mean |
| Body Composition Features | pectoralis minor Hounsfield units median |
| Body Composition Features | pectoralis minor Hounsfield units minimum |
| Body Composition Features | pectoralis minor Hounsfield units mode |
| Body Composition Features | pectoralis minor Hounsfield units skewness |
| Body Composition Features | pectoralis minor Hounsfield units standard deviation |
| Body Composition Features | pectoralis minor sagittal cross sectional area |
| Body Composition Features | pectoralis minor lean axial cross sectional area |
| Body Composition Features | pectoralis minor lean coronal cross sectional area |
| Body Composition Features | pectoralis minor lean Hounsfield units kurtosis |
| Body Composition Features | pectoralis minor lean Hounsfield units mean |
| Body Composition Features | pectoralis minor lean Hounsfield units median |
| Body Composition Features | pectoralis minor lean Hounsfield units minimum |
| Body Composition Features | pectoralis minor lean Hounsfield |
| Body Composition Features | pectoralis minor lean Hounsfield units skewness |
| Body Composition Features | pectoralis minor lean Hounsfield units standard deviation |
| Body Composition Features | pectoralis minor lean sagittal cross sectional area |
| Body Composition Features | pectoralis major axial cross sectional area |
| Body Composition Features | pectoralis major coronal cross sectional area |
| Body Composition Features | pectoralis major Hounsfield units kurtosis |
| Body Composition Features | pectoralis major Hounsfield units maximum |

TABLE 2-continued

Example Non-nodule-Specific Features

| Feature Type | Feature |
|---|---|
| Body Composition Features | pectoralis major Hounsfield units mean |
| Body Composition Features | pectoralis major Hounsfield units median |
| Body Composition Features | pectoralis major Hounsfield units minimum |
| Body Composition Features | pectoralis major Hounsfield units mode |
| Body Composition Features | pectoralis major Hounsfield units skewness |
| Body Composition Features | pectoralis major Hounsfield units standard deviation |
| Body Composition Features | pectoralis major sagittal cross sectional area |
| Body Composition Features | pectoralis major lean axial cross sectional area |
| Body Composition Features | pectoralis major lean coronal cross sectional area |
| Body Composition Features | pectoralis major lean Hounsfield units kurtosis |
| Body Composition Features | pectoralis major lean Hounsfield units mean |
| Body Composition Features | pectoralis major lean Hounsfield units median |
| Body Composition Features | pectoralis major lean Hounsfield units mode |
| Body Composition Features | pectoralis major lean Hounsfield units skewness |
| Body Composition Features | pectoralis major lean Hounsfield units standard deviation |
| Body Composition Features | pectoralis major lean sagittal cross sectional area |
| Body Composition Features | subcutaneous fat axial cross sectional area |
| Body Composition Features | subcutaneous fat coronal cross sectional area |
| Body Composition Features | subcutaneous fat Hounsfield units kurtosis |
| Body Composition Features | subcutaneous fat Hounsfield units maximum |
| Body Composition Features | subcutaneous fat Hounsfield units mean |
| Body Composition Features | subcutaneous fat Hounsfield units median |
| Body Composition Features | subcutaneous fat Hounsfield units minimum |
| Body Composition Features | subcutaneous fat Hounsfield units mode |
| Body Composition Features | subcutaneous fat Hounsfield units skewness |
| Body Composition Features | subcutaneous fat Hounsfield units standard deviation |
| Body Composition Features | subcutaneous fat sagittal cross sectional area |
| Body Composition Features | subcutaneous fat lean axial cross sectional area |
| Body Composition Features | subcutaneous fat lean coronal cross sectional area |
| Body Composition Features | subcutaneous fat lean Hounsfield units kurtosis |
| Body Composition Features | subcutaneous fat lean Hounsfield units maximum |
| Body Composition Features | subcutaneous fat lean Hounsfield units mean |
| Body Composition Features | subcutaneous fat lean Hounsfield units median |
| Body Composition Features | subcutaneous fat lean Hounsfield units mode |
| Body Composition Features | subcutaneous fat lean Hounsfield units skewness |
| Body Composition Features | subcutaneous fat lean Hounsfield units standard deviation |
| Body Composition Features | subcutaneous fat lean sagittal cross sectional area |
| Densitometric Features | high attenuation area 250 |
| Densitometric Features | high attenuation area 500 |
| Densitometric Features | high attenuation area 600 |
| Densitometric Features | high attenuation area 700 |
| Densitometric Features | low attenuation area 856 |
| Densitometric Features | low attenuation area 875 |
| Densitometric Features | low attenuation area 900 |
| Densitometric Features | low attenuation area 905 |
| Densitometric Features | low attenuation area 910 |
| Densitometric Features | low attenuation area 925 |
| Densitometric Features | low attenuation area 950 |
| Densitometric Features | whole lung density |
| Densitometric Features | whole lung mass |
| Densitometric Features | $10^{th}$ percentile of lung density |
| Densitometric Features | $15^{th}$ percentile of lung density |
| Densitometric Features | whole lung volume |
| Densitometric Features | high attenuation area 600 |
| Densitometric Features | upper lower third low attenuation area 950 ratio |
| Lung Parenchyma Features | normal parenchyma low attenuation area 950 |
| Lung Parenchyma Features | centrilobular emphysema low attenuation area 950 |
| Lung Parenchyma Features | reticular low attenuation area 950 |
| Lung Parenchyma Features | normal parenchyma low attenuation area 925 |
| Lung Parenchyma Features | centrilobular emphysema low attenuation area 925 |
| Lung Parenchyma Features | reticular low attenuation area 925 |
| Lung Parenchyma Features | low attenuation area 910 |
| Lung Parenchyma Features | normal parenchyma low attenuation area 910 |
| Lung Parenchyma Features | centrilobular emphysema low attenuation area 910 |
| Lung Parenchyma Features | reticular low attenuation area 910 |
| Lung Parenchyma Features | low attenuation area 905 |
| Lung Parenchyma Features | normal parenchyma low attenuation area 905 |
| Lung Parenchyma Features | centrilobular emphysema low attenuation area 905 |
| Lung Parenchyma Features | reticular low attenuation area 905 |
| Lung Parenchyma Features | low attenuation area 900 |
| Lung Parenchyma Features | normal parenchyma low attenuation area 900 |
| Lung Parenchyma Features | centrilobular emphysema low attenuation area 900 |
| Lung Parenchyma Features | reticular low attenuation area 900 |
| Lung Parenchyma Features | low attenuation area 875 |
| Lung Parenchyma Features | normal parenchyma low attenuation area 875 |
| Lung Parenchyma Features | centrilobular emphysema low attenuation area 875 |

TABLE 2-continued

Example Non-nodule-Specific Features

| Feature Type | Feature |
|---|---|
| Lung Parenchyma Features | reticular low attenuation area 875 |
| Lung Parenchyma Features | low attenuation area 856 |
| Lung Parenchyma Features | normal parenchyma low attenuation area 856 |
| Lung Parenchyma Features | centrilobular emphysema low attenuation area 856 |
| Lung Parenchyma Features | reticular low attenuation area 856 |
| Lung Parenchyma Features | high attenuation area 700 |
| Lung Parenchyma Features | normal parenchyma high attenuation area 700 |
| Lung Parenchyma Features | centrilobular emphysema high attenuation area 700 |
| Lung Parenchyma Features | reticular high attenuation area 700 |
| Lung Parenchyma Features | high attenuation area 600 |
| Lung Parenchyma Features | normal parenchyma high attenuation area 600 |
| Lung Parenchyma Features | centrilobular emphysema high attenuation area 600 |
| Lung Parenchyma Features | reticular high attenuation area 600 |
| Lung Parenchyma Features | high attenuation area 500 |
| Lung Parenchyma Features | normal parenchyma high attenuation area 500 |
| Lung Parenchyma Features | centrilobular emphysema high attenuation area 500 |
| Lung Parenchyma Features | reticular high attenuation area 500 |
| Lung Parenchyma Features | high attenuation area 250 |
| Lung Parenchyma Features | normal parenchyma high attenuation area 250 |
| Lung Parenchyma Features | centrilobular emphysema high attenuation area 250 |
| Lung Parenchyma Features | reticular high attenuation area 250 |
| Lung Parenchyma Features | $10^{th}$ percentile of normal parenchyma lung density |
| Lung Parenchyma Features | $10^{th}$ percentile of centrilobular emphysema lung density |
| Lung Parenchyma Features | $10^{th}$ percentile of reticular lung density |
| Lung Parenchyma Features | $15^{th}$ percentile normal parenchyma lung density |
| Lung Parenchyma Features | $15^{th}$ percentile of normal parenchyma lung density |
| Lung Parenchyma Features | $15^{th}$ percentile of centrilobular emphysema lung density |
| Lung Parenchyma Features | normal parenchyma Hounsfield units mean |
| Lung Parenchyma Features | centrilobular emphysema Hounsfield units mean |
| Lung Parenchyma Features | reticular Hounsfield units mean |
| Lung Parenchyma Features | normal parenchyma Hounsfield units standard deviation |
| Lung Parenchyma Features | centrilobular emphysema Hounsfield units standard deviation |
| Lung Parenchyma Features | reticular Hounsfield units standard deviation |
| Lung Parenchyma Features | normal parenchyma Hounsfield units kurtosis |
| Lung Parenchyma Features | centrilobular emphysema Hounsfield units kurtosis |
| Lung Parenchyma Features | reticular Hounsfield units kurtosis |
| Lung Parenchyma Features | normal parenchyma Hounsfield units skewness |
| Lung Parenchyma Features | centrilobular emphysema Hounsfield units skewness |
| Lung Parenchyma Features | reticular Hounsfield units skewness |
| Lung Parenchyma Features | normal parenchyma Hounsfield units mode |
| Lung Parenchyma Features | centrilobular emphysema Hounsfield units mode |
| Lung Parenchyma Features | reticular Hounsfield units mode |
| Lung Parenchyma Features | normal parenchyma Hounsfield units median |
| Lung Parenchyma Features | centrilobular emphysema Hounsfield units median |
| Lung Parenchyma Features | reticular Hounsfield units median |
| Lung Parenchyma Features | normal parenchyma Hounsfield units minimum |
| Lung Parenchyma Features | centrilobular emphysema Hounsfield units minimum |
| Lung Parenchyma Features | reticular Hounsfield units minimum |
| Lung Parenchyma Features | normal parenchyma Hounsfield units maximum |
| Lung Parenchyma Features | centrilobular emphysema Hounsfield units maximum |
| Lung Parenchyma Features | reticular Hounsfield units maximum |
| Lung Parenchyma Features | normal parenchyma Hounsfield units mean 950 |
| Lung Parenchyma Features | centrilobular emphysema Hounsfield units mean 950 |
| Lung Parenchyma Features | reticular Hounsfield units mean 950 |
| Lung Parenchyma Features | normal parenchyma Hounsfield units standard deviation 950 |
| Lung Parenchyma Features | centrilobular emphysema Hounsfield units standard deviation 950 |
| Lung Parenchyma Features | reticular Hounsfield units standard deviation 950 |
| Lung Parenchyma Features | normal parenchyma Hounsfield units kurtosis 950 |
| Lung Parenchyma Features | centrilobular emphysema Hounsfield units kurtosis 950 |
| Lung Parenchyma Features | reticular Hounsfield units kurtosis 950 |
| Lung Parenchyma Features | normal parenchyma Hounsfield units skewness 950 |
| Lung Parenchyma Features | centrilobular emphysema Hounsfield units skewness 950 |
| Lung Parenchyma Features | reticular Hounsfield units skewness 950 |
| Lung Parenchyma Features | normal parenchyma Hounsfield units mode 950 |
| Lung Parenchyma Features | centrilobular emphysema Hounsfield units mode 950 |
| Lung Parenchyma Features | reticular Hounsfield units mode 950 |
| Lung Parenchyma Features | normal parenchyma Hounsfield units median 950 |
| Lung Parenchyma Features | centrilobular emphysema Hounsfield units median 950 |
| Lung Parenchyma Features | reticular Hounsfield units median 950 |
| Lung Parenchyma Features | normal parenchyma Hounsfield units min 950 |
| Lung Parenchyma Features | centrilobular emphysema Hounsfield units min 950 |
| Lung Parenchyma Features | reticular Hounsfield units min 950 |
| Lung Parenchyma Features | normal parenchyma Hounsfield units mean 500 |

TABLE 2-continued

Example Non-nodule-Specific Features

| Feature Type | Feature |
|---|---|
| Lung Parenchyma Features | centrilobular emphysema Hounsfield units mean 500 |
| Lung Parenchyma Features | reticular Hounsfield units mean 500 |
| Lung Parenchyma Features | normal parenchyma Hounsfield units standard deviation 500 |
| Lung Parenchyma Features | centrilobular emphysema Hounsfield units standard deviation 500 |
| Lung Parenchyma Features | reticular Hounsfield units standard deviation 500 |
| Lung Parenchyma Features | normal parenchyma Hounsfield units kurtosis 500 |
| Lung Parenchyma Features | centrilobular emphysema Hounsfield units kurtosis 500 |
| Lung Parenchyma Features | reticular Hounsfield units kurtosis 500 |
| Lung Parenchyma Features | normal parenchyma Hounsfield units skewness 500 |
| Lung Parenchyma Features | centrilobular emphysema Hounsfield units skewness 500 |
| Lung Parenchyma Features | reticular Hounsfield units skewness 500 |
| Lung Parenchyma Features | normal parenchyma Hounsfield units mode 500 |
| Lung Parenchyma Features | centrilobular emphysema Hounsfield units mode 500 |
| Lung Parenchyma Features | reticular Hounsfield units mode 500 |
| Lung Parenchyma Features | normal parenchyma Hounsfield units median 500 |
| Lung Parenchyma Features | centrilobular emphysema Hounsfield units median 500 |
| Lung Parenchyma Features | reticular Hounsfield units median 500 |
| Lung Parenchyma Features | normal parenchyma Hounsfield units min 500 |
| Lung Parenchyma Features | centrilobular emphysema Hounsfield units min 500 |
| Lung Parenchyma Features | reticular Hounsfield units min 500 |
| Lung Parenchyma Features | centrilobular emphysema Hounsfield units max 500 |
| Lung Parenchyma Features | whole lung volume |
| Lung Parenchyma Features | normal parenchyma volume |
| Lung Parenchyma Features | centrilobular emphysema volume |
| Lung Parenchyma Features | honeycombing volume |
| Lung Parenchyma Features | linear scar volume |
| Lung Parenchyma Features | nodular volume |
| Lung Parenchyma Features | reticular volume |
| Lung Parenchyma Features | subpleural line volume |
| Lung Parenchyma Features | nodular volume |
| Lung Parenchyma Features | whole lung mass |
| Lung Parenchyma Features | normal parenchyma mass |
| Lung Parenchyma Features | centrilobular emphysema mass |
| Lung Parenchyma Features | reticular mass |
| Lung Parenchyma Features | normal parenchyma type fraction |
| Lung Parenchyma Features | centrilobular emphysema type fraction |
| Lung Parenchyma Features | honeycombing type fraction |
| Lung Parenchyma Features | linear scar type fraction |
| Lung Parenchyma Features | nodular type fraction |
| Lung Parenchyma Features | reticular type fraction |
| Lung Parenchyma Features | subpleural line type fraction |
| Lung Parenchyma Features | panlobular emphysema type fraction |
| Lung Parenchyma Features | centrilobular nodule type fraction |
| Lung Parenchyma Features | ground glass type fraction |
| Lung Parenchyma Features | emphysematous type fraction |
| Lung Parenchyma Features | cyst type fraction |
| Longitudinal non-nodule features | Change in any of 1) body composition features, 2) densitometric features, or 3) lung parenchyma features |

TABLE 3

Example Nodule-Specific Features

| Feature Type | Feature |
|---|---|
| First Order Statistics | energy |
| First Order Statistics | total energy |
| First Order Statistics | entropy |
| First Order Statistics | minimum |
| First Order Statistics | $10^{th}$ percentile |
| First Order Statistics | $90^{th}$ percentile |
| First Order Statistics | maximum |
| First Order Statistics | mean |
| First Order Statistics | median |
| First Order Statistics | interquartile range |
| First Order Statistics | range |
| First Order Statistics | mean absolute deviation |
| First Order Statistics | robust mean absolute deviation |
| First Order Statistics | root mean squared |
| First Order Statistics | standard deviation |
| First Order Statistics | skewness |

TABLE 3-continued

Example Nodule-Specific Features

| Feature Type | Feature |
| --- | --- |
| First Order Statistics | kurtosis |
| First Order Statistics | variance |
| First Order Statistics | uniformity |
| Shape based three-dimensional features | mesh volume |
| Shape based three-dimensional features | voxel volume |
| Shape based three-dimensional features | surface area |
| Shape based three-dimensional features | surface area to volume ratio |
| Shape based three-dimensional features | sphericity |
| Shape based three-dimensional features | compactness 1 |
| Shape based three-dimensional features | compactness 2 |
| Shape based three-dimensional features | spherical disproportion |
| Shape based three-dimensional features | maximum 3d diameter |
| Shape based three-dimensional features | maximum 2d diameter (slice) |
| Shape based three-dimensional features | maximum 2d diameter (column) |
| Shape based three-dimensional features | maximum 2df diameter (row) |
| Shape based three-dimensional features | major axis length |
| Shape based three-dimensional features | minor axis length |
| Shape based three-dimensional features | least axis length |
| Shape based three-dimensional features | elongation |
| Shape based three-dimensional features | flatness |
| Shape based two-dimensional features | mesh surface |
| Shape based two-dimensional features | pixel surface |
| Shape based two-dimensional features | perimeter |
| Shape based two-dimensional features | perimeter to surface ratio |
| Shape based two-dimensional features | sphericity |
| Shape based two-dimensional features | spherical disproportion |
| Shape based two-dimensional features | maximum 2d diameter |
| Shape based two-dimensional features | major axis length |
| Shape based two-dimensional features | minor axis length |
| Shape based two-dimensional features | elongation |
| Gray level cooccurance matrix features | autocorrelation |
| Gray level cooccurance matrix features | joint average |
| Gray level cooccurance matrix features | cluster prominence |
| Gray level cooccurance matrix features | cluster shade |
| Gray level cooccurance matrix features | cluster tendency |
| Gray level cooccurance matrix features | contrast |
| Gray level cooccurance matrix features | correlation |
| Gray level cooccurance matrix features | difference average |
| Gray level cooccurance matrix features | difference entropy |
| Gray level cooccurance matrix features | difference variance |
| Gray level cooccurance matrix features | joint energy |
| Gray level cooccurance matrix features | joint entropy |
| Gray level cooccurance matrix features | informational measure of correlation 1 |
| Gray level cooccurance matrix features | informational measure of correlation 2 |
| Gray level cooccurance matrix features | inverse difference moment |
| Gray level cooccurance matrix features | maximal correlation coefficient |
| Gray level cooccurance matrix features | inverse difference moment normalized |
| Gray level cooccurance matrix features | inverse difference |
| Gray level cooccurance matrix features | inverse difference normalized |
| Gray level cooccurance matrix features | inverse variance |
| Gray level cooccurance matrix features | maximum probability |
| Gray level cooccurance matrix features | sum average |
| Gray level cooccurance matrix features | sum entropy |
| Gray level cooccurance matrix features | sum of squares |
| Gray level run length matrix features | small area emphasis |
| Gray level run length matrix features | large area emphasis |
| Gray level run length matrix features | gray level non-uniformity |
| Gray level run length matrix features | gray level non-uniformity normalized |
| Gray level run length matrix features | site zone non uniformity |
| Gray level run length matrix features | site zone non uniformity normalized |
| Gray level run length matrix features | zone percentage |
| Gray level run length matrix features | gray level variance |
| Gray level run length matrix features | zone variance |
| Gray level run length matrix features | zone entropy |
| Gray level run length matrix features | low gray level zone emphasis |
| Gray level run length matrix features | high gray level zone emphasis |
| Gray level run length matrix features | small area low gray level emphasis |
| Gray level run length matrix features | small area high gray level emphasis |
| Gray level run length matrix features | large area low gray level emphasis |
| Gray level run length matrix features | large area high gray level emphasis |
| Gray level size zone matrix features | short run emphasis |
| Gray level size zone matrix features | long run emphasis |
| Gray level size zone matrix features | gray level non-uniformity |
| Gray level size zone matrix features | gray level non-uniformity normalized |
| Gray level size zone matrix features | run length non-uniformity |
| Gray level size zone matrix features | run length non-uniformity normalized |

TABLE 3-continued

Example Nodule-Specific Features

| Feature Type | Feature |
| --- | --- |
| Gray level size zone matrix features | run percentage |
| Gray level size zone matrix features | gray level variance |
| Gray level size zone matrix features | run variance |
| Gray level size zone matrix features | run entropy |
| Gray level size zone matrix features | low gray level run emphasis |
| Gray level size zone matrix features | high gray level run emphasis |
| Gray level size zone matrix features | short run low gray level emphasis |
| Gray level size zone matrix features | short run high gray level emphasis |
| Gray level size zone matrix features | long run low gray level emphasis |
| Gray level size zone matrix features | long run high gray level emphasis |
| Neighboring gray tone difference features | coarseness |
| Neighboring gray tone difference features | contrast |
| Neighboring gray tone difference features | busyness |
| Neighboring gray tone difference features | complexity |
| Neighboring gray tone difference features | strength |
| Gray level dependence features | small dependence emphasis |
| Gray level dependence features | large dependence emphasis |
| Gray level dependence features | gray level non-uniformity |
| Gray level dependence features | dependence non-uniformity |
| Gray level dependence features | dependence non-uniformity normalized |
| Gray level dependence features | gray level variance |
| Gray level dependence features | dependence variance |
| Gray level dependence features | dependence entropy |
| Gray level dependence features | low gray level emphasis |
| Gray level dependence features | high gray level emphasis |
| Gray level dependence features | small dependence low gray level emphasis |
| Gray level dependence features | small dependence high gray level emphasis |
| Gray level dependence features | large dependence low gray level emphasis |
| Gray level dependence features | large dependence high gray level emphasis |
| Longitudinal nodule features | Change in any of<br>1) first order statistics,<br>2) shape based three-dimensional features,<br>3) shape based two-dimensional features,<br>4) Gray level cooccurance matrix features,<br>5) Gray level run length matrix features,<br>6) Gray level size zone matrix features,<br>7) Neighboring gray tone difference features, or<br>8) Gray level dependence features |

The invention claimed is:

1. A method for predicting one or more risks of lung cancer for a subject, the method comprising:
obtaining one or more images captured from the subject;
extracting features from the one or more obtained images, the extracted features including at least one of a longitudinal lung parenchyma feature associated with an absence of nodules or a longitudinal body composition feature associated with an absence of nodules; and
predicting one or more risks of lung cancer for the subject based on a risk prediction model trained to analyze the extracted features from the one or more obtained images and generate a predicted score indicating a likelihood of the subject developing lung cancer.

2. The method of claim 1, wherein predicting the one or more risks of lung cancer for the subject comprises;
predicting a likelihood of the subject developing lung cancer within M years.

3. The method of claim 1, wherein the extracted features include the longitudinal lung parenchyma feature and the longitudinal body composition feature.

4. The method of claim 3, wherein the extracted features further include at least one of a non-longitudinal lung parenchyma feature associated with an absence of nodules or a non-longitudinal body composition feature associated with an absence of nodules.

5. The method of claim 1, wherein the longitudinal lung parenchyma feature comprises at least one of a change in densitometric measures of a lung parenchyma or a change in local histogram measures of the lung parenchyma.

6. The method of claim 5, wherein the longitudinal lung parenchyma feature comprises the change in the densitometric measures of the lung parenchyma, and wherein the densitometric measures of the lung parenchyma include a ratio of a low attenuation or a high attenuation area in an upper lung zone in comparison to a lower lung zone.

7. The method of claim 5, wherein the longitudinal lung parenchyma feature comprises the change in the local histogram measures of the lung parenchyma, and wherein the local histogram measures of the lung parenchyma include a percentage of lung occupied by at least one of normal tissue, centrilobular emphysema, ground glass, honeycombing, a linear scar, reticular patterns, a subpleural line, other emphysema, or one or more cysts.

8. The method of claim 1, wherein the longitudinal body composition feature comprises at least one of a change in a pectoralis cross-sectional area, a change in a pectoralis lean cross-sectional area, or a change in a subcutaneous fat cross-sectional area.

9. The method of claim 1, wherein the one or more risks of lung cancer comprise at least one of a likelihood that the subject has cancer, a likelihood that the subject will develop cancer within N months, or a likelihood that the subject will develop cancer at any time in the future.

10. The method of claim 1, wherein the extracted features further comprise nodule specific features.

11. The method of claim 10, wherein the nodule specific features include longitudinal nodule specific features, and wherein the longitudinal nodule specific features include at least one of a change in nodule specific attenuation, a change in nodule margin description, a change in nodule size, a change in nodule shape, a change in nodule texture, a change in nodule diameter, a change in Lung-RADS score, or a change in radiomic features.

12. The method of claim 11, wherein the longitudinal nodule specific features comprise the change in radiomic features, and wherein the radiomic features include at least one of first order statistics, 3D shape based features, 2D shape based features, a gray level co-occurrence matrix, a gray level run length matrix, a gray level size zone matrix, a neighboring gray tone difference matrix, or a gray level dependence matrix.

13. The method of claim 10, wherein the risk prediction model that includes at least:
- a first submodel configured to analyze features associated with an absence of nodules; and
- a second submodel configured to analyze the nodule specific features.

14. The method of claim 13, wherein the risk prediction model further includes a third submodel configured to analyze predicted outputs of the first submodel and the second submodel, wherein the one or more risks of lung cancer are based at least in part on an output of the third submodel.

15. The method of claim 1, wherein the risk prediction model is trained using images captured from individuals that do not have any lung nodules indicative of cancer.

16. The method of claim 1, wherein the one or more images are computed tomography (CT) images or X-ray images.

17. The method of claim 1, wherein the one or more images include at least a first image captured from the subject at a first timepoint and a second image captured from the subject at a second timepoint different than the first timepoint.

18. The method of claim 17, wherein a duration between the first timepoint and the second timepoint is on the order of weeks, months, or years.

19. The method of claim 1, wherein the risk prediction model is trained on a plurality of training features each having a respective importance value that determines how heavily the training feature influences the predicted score.

20. A non-transitory computer readable medium for predicting one or more future risks of lung cancer for a subject, the non-transitory computer readable medium comprising instructions that, when executed by a processor, cause the processor to:
- obtain one or more images captured from the subject;
- extract features from the one or more obtained images, the extracted features including at least one of a longitudinal lung parenchyma feature associated with an absence of nodules or a longitudinal body composition feature associated with an absence of nodules; and
- predict one or more risks of lung cancer for the subject based on a risk prediction model trained to analyze the extracted features from the one or more obtained images and generate a predicted score indicating a likelihood of the subject developing lung cancer.

* * * * *

UNITED STATES PATENT AND TRADEMARK OFFICE
CERTIFICATE OF CORRECTION

PATENT NO. : 12,293,832 B2
APPLICATION NO. : 17/863978
DATED : May 6, 2025
INVENTOR(S) : George R. Washko, Jr. et al.

Page 1 of 1

It is certified that error appears in the above-identified patent and that said Letters Patent is hereby corrected as shown below:

In the Claims

In Column 77, Line 55, in Claim 2, delete "more risks of lung cancer for the subject comprises;" and insert -- more risks of lung cancer for the subject comprises: --

In Column 79, Line 18, in Claim 13, delete "model that includes at least:" and insert -- model includes at least: --

Signed and Sealed this
Third Day of June, 2025

Coke Morgan Stewart
*Acting Director of the United States Patent and Trademark Office*